US008658398B2

(12) United States Patent
Brevnova et al.

(10) Patent No.: US 8,658,398 B2
(45) Date of Patent: Feb. 25, 2014

(54) HETEROLOGOUS EXPRESSION OF TERMITE CELLULASES YEAST

(75) Inventors: Elena E. Brevnova, Lebanon, NH (US); Vineet Rajgarhia, Lebanon, NH (US); Mark Mellon, Grantham, NH (US); Anne Warner, Lebanon, NH (US); John McBride, Lebanon, NH (US); Chhayal Gandhi, Lebanon, NH (US); Erin Wiswall, Danbury, NH (US)

(73) Assignee: Mascoma Corporation, Lebanon, NH (US)

( * ) Notice: Subject to any disclaimer, the term of this patent is extended or adjusted under 35 U.S.C. 154(b) by 0 days.

(21) Appl. No.: 13/003,200

(22) PCT Filed: Jul. 7, 2009

(86) PCT No.: PCT/US2009/003970
§ 371 (c)(1),
(2), (4) Date: Sep. 6, 2011

(87) PCT Pub. No.: WO2010/005551
PCT Pub. Date: Jan. 14, 2010

(65) Prior Publication Data
US 2012/0003701 A1 Jan. 5, 2012

Related U.S. Application Data

(60) Provisional application No. 61/078,735, filed on Jul. 7, 2008.

(51) Int. Cl.
*C12P 19/14* (2006.01)
(52) U.S. Cl.
USPC .......................................................... 435/99
(58) Field of Classification Search
USPC .......................................................... 435/99
See application file for complete search history.

(56) References Cited

FOREIGN PATENT DOCUMENTS

| CN | 101245343 A | 8/2003 |
|---|---|---|
| JP | 11-46764 A | 2/1999 |
| JP | 2003-70475 A | 3/2003 |
| WO | WO 03/000941 A2 | 1/2003 |
| WO | WO 2010/005551 A2 | 1/2010 |

OTHER PUBLICATIONS

Nakashima et al. [Insect Biochem. Mol. Biol. 32 (7), 777-784 (2002)].*
Brune, A., et al., "Microbiology: Woodworker's digest,"*Nature* 450: 487-488, Nature Publishing Group, England (2007).
Carbone, A., et al., "Codon adaptation index as a measure of dominating codon bias," *Bioinformatics* 19(16):2005-2015, Oxford University Press, England (2003).
Delalibera Jr., I., et al., "Contracts in Cellulolytic Activities of Gut Microorganisms Between the Wood Borer, *Saperda vestita* (Coleptera:Cerambycidae), and the Bark Beetles, *Ips pini* and *Dendroctonus frontailis* (Coleptera: Curculionidae)," *Environ. Entomol.* 34(3):541-547, Entomological Society of America, United States (2005).
Delroisse, J-M., et al., "Expression of synthetic gene encoding a *Tribolium castaneum* carboxylesterase in *Pichia pastoris,*" *Protein. Expr. Purif.* 42(2005):286-294, Elsevier Inc., United States (2005).
Demain, A.L., et al., "Cellulase, Clostridia, and Ethanol," *Microbiol. Mol. Biol. Rev.* 69(1):124-154, American Society for Microbiology, United States (2005).
Hahn-Hägerdal, B. et al., "Metabolic Engineering of *Saccharomyces cerevisiae* for Xylose Utilization," *Adv. Biochem, Eng. Biotechnol.* 73:53-84, Springer-Verlag Berlin Heidelberg, Germany (2001).
Hector, R. et al., "Developing Yeast Strains for Biomass-to-Ethanol Production," *Biomass Magazine*, BBI International Media, United States (Apr. 2008) http://biomassmagazine.com/articles/1533/developing-yeast-strains-for-biomass-to-ethanol-production.
Kotula, L. and Curtis, P.J., "Evaluation of foreign gene codon optimization in yeast: expression of a mouse IG kappa chain," *Biotechnology (N Y)* 9(12):1386-1389, Nature Publishing Company, United States (1991).
Nakamura, Y., et al., "Codon Usage tabulated from international DNA sequence databases: status for the year 2000," *Nucleic Acids Res.* 28(1):292, Oxford University Press, England (2000).
Ni, J., et al., "Heterologous Overexpression of a Mutant Termite Cellulase Gene in *Escherichia coli* by DNA Shuffling of Four Orthologous Parental cDNAs" *Biosci. Biotechnol. Biochem.* 69(9):1711-1720, Japan Society for Bioscience, Biotechnology, and Agrochemistry, Japan (2005).
Odelson, D.A., et al., "Cellulase and Other Polymer-Hydrolyzing Activities of *Trichomitopsis termopsidis*, a Symbiotic Protozoan from Termites," *Appl. Environ. Microbiol.* 49(3):622-626, American Society for Microbiology, United States (1985).
Sasaguri, S., et al., "Codon optimization prevents premature polyadenylation of heterologously-expressed cellulases from termite-gut symbionts in *Aspergillus oryzae,*" *J. Gen. Appl. Microbiol.* 54(6):343-351, Institute of Applied Microbiology University of Tokyo, Japan (Dec. 2008).
Sharp, P.M. and Wen-Hsiung, L., "The codon adaptation indexa measure of directional synonymous codon usage bias, and its potential applications," *Nucleic Acids Res.* 15(3):1281-1295, IRL Press Limited, England (1987).
Singer, E., "Termite Guts Could Boost Ethanol Efficiency: A metagenomic study could suggest ways to make cellulosic ethanol," *Technology Review*, Massachusetts Institute of Technology, United States (2007) http://www.technologyreview.com/energy/19745/.
Sun, Y., and Cheng, J., "Hydrolysis of lignocellulosic materials for ethanol production: a review," *Bioresour. Technol.* 83(1):1-11, Elsevier Science Ltd., England (2002).

(Continued)

*Primary Examiner* — Tekchand Saidha
(74) *Attorney, Agent, or Firm* — Sterne, Kessler, Goldstein & Fox P.L.L.C.

(57) ABSTRACT

The present invention provides for heterologous expression of termite and termite-associated symbiont cellulases. The cellulases can, for example, be codon-optimized and expressed in yeast host cells, such as the yeast *Saccharomyces cerevisiae*. The cellulases can also be co-expressed in host cells with other cellulases. The expression in such host cells of the termite and termite-associated symbiont cellulases, and variants and combinations thereof, result in yeast with improved cellulosic activity. Thus, such genes and expression systems are useful for efficient and cost-effective consolidated bioprocessing systems.

20 Claims, 6 Drawing Sheets

(56) References Cited

OTHER PUBLICATIONS

Figure 1:
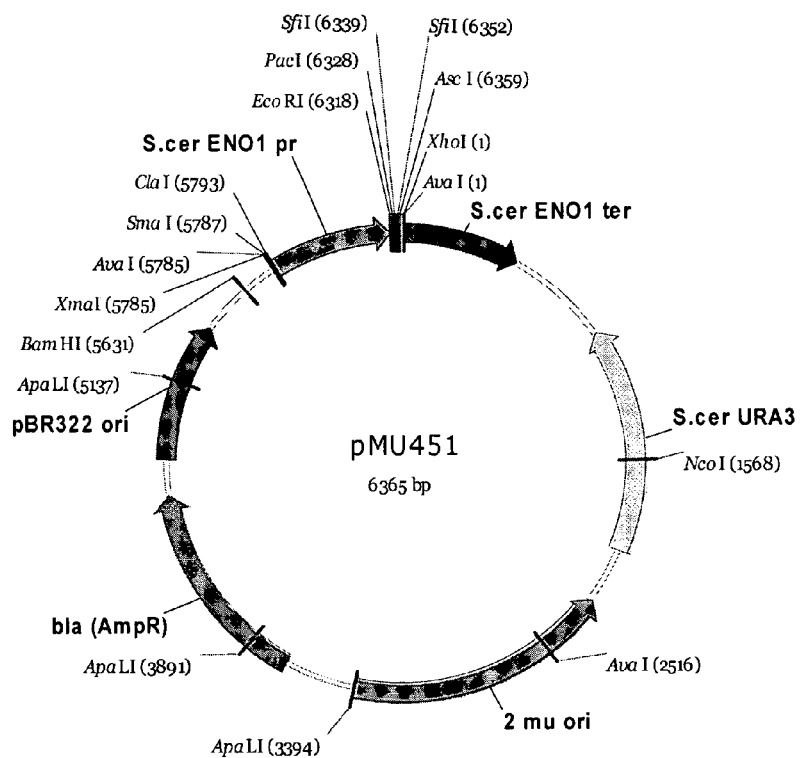

Tokuda, G., et al., "Metazoan cellulase genes from termites: intron/exon structures and sites of expression," *Biochim Biophys Acta* 1447(2-3):146-159, Elsevier Science B.V., Netherlands (1999).

Warnecke, F., et al., "Metagenomic and functional analysis of hindgut microbiota of a wood-feeding higher termite," *Nature* 450(7169):560-565, Nature Publishing Group, England (2007).

Watanabe, H., and Tokuda, G., "Animal cellulases," *CMLS Cell. Mol. Life Sci.* 58(2001):1167-1178, Birkhäuser Verlag, Switzerland (2001).

Watanabe, H., et al., "Symbiotic Archaezoa of the Primitive Termite *Mastotermes darwiniensis* Still Play a Role in Cellulase Production," *Eukaryot. Cell* 5(9):1571-1576, American Society for Mircrobiology, United States (2006).

Watanabe, Y., et al., "Isolation of Actinomycetes from Termites' Guts," *Biosci. Biotechnol. Biochem.* 67(8):1797-1801, Japan Society for Bioscience, Biotechnology, and Agrochemistry, Japan (2003).

"Termite Guts, Brewer's Yeast, and Biofuels: WPI Team Applies Nature's Expertise for Next-Generation Biofuels Development," News & Events—News Releases, Wocester Polytechnic Institute, United States (Apr. 2008) http://www.wpi.edu/news/20078/biofuels.html.

International Search Report for International Application No. PCT/US2009/003970, European Patent Office, Netherlands, mailed on Jan. 25, 2010.

English language abstract for Japanese Patent Publication No. JP 11046464 A, European Patent Office, espacenet database—Worldwide (1999) (listed as document FP1 on the accompanying equivalent from PTO/SB/08A).

English language abstract for Japanese Patent Application No. JP 2003070475 A, European Patent Office, espacenet database—Worldwide (2003) (listed as document FP3 on the accompanying equivalent form PTO/SB/08A).

English language abstract for Chinese Patent Application No. CN 101 245 343 A, European Patent Office, espacenet database—Worldwide (2008) (listed as document FP4 on the accompanying equivalent form PTO/SB/08A).

International Preliminary Report on Patentability for International Application No. PCT/US2009/003970, The International Bureau of WIPO, Switzerland, issued Jan. 11, 2011.

Rajgopal, S., et al., "Associates of fungi in the termite gut," *Curr. Sci.* 48(22):998-999, Indian Academy of Sciences, India (1979).

Rajgopal, S., et al., "Fungi of the Worker Termite-gut, *Odontotermes obesus* (Rambur) from Northern India," *Nova Hedwigia* 34:97-100, E. Schweizerbart Science Publishers, Germany (1981).

Schäfer, A. et al., "Hemicellulose-degrading bacteria yeasts from the termite gut," *J. Appl. Bacteriol.* 80:471-478, The Society for Applied Microbiology, England (1996).

Pasti, M.B. and Belli, M.L., "Cellulolytic activity of Actinomycetes isolated from termites (Termitidae) gut," *FEMS Microbiol. Let.* 26:107-112, Blackwell Publishing Ltd., England (1985).

Crow, K.S., et al., "Nature's Ethanol Factory," *UF Genetrics*, University of Florida's Scientific Thinking and Educational Partnership program, http://ufgenetics.com/default.aspx (2007).

\* cited by examiner

HETEROLOGOUS EXPRESSION OF TERMITE CELLULASES YEAST

This is a U.S. National Phase of International Appl. No. PCT/US2009/003970, filed Jul. 7, 2009, which claims the benefit of U.S. Provisional Appl. No. 61/078,735, filed Jul. 7, 2008, each of which is hereby incorporated by reference in its entirety.

BACKGROUND OF THE INVENTION

Lignocellulosic biomass is widely recognized as a promising source of raw material for production of renewable fuels and chemicals. The primary obstacle impeding the more widespread production of energy from biomass feedstocks is the general absence of low-cost technology for overcoming the recalcitrance of these materials to conversion into useful fuels. Lignocellulosic biomass contains carbohydrate fractions (e.g., cellulose and hemicellulose) that can be converted into ethanol. In order to convert these fractions, the cellulose and hemicellulose must ultimately be converted or hydrolyzed into monosaccharides; it is the hydrolysis that has historically proven to be problematic.

Biologically mediated processes are promising options for energy conversion, in particular for the conversion of lignocellulosic biomass into fuels. Biomass processing schemes involving enzymatic or microbial hydrolysis commonly involve four biologically mediated transformations: (1) the production of saccharolytic enzymes (cellulases and hemicellulases); (2) the hydrolysis of carbohydrate components present in pretreated biomass to sugars; (3) the fermentation of hexose sugars (e.g., glucose, mannose, and galactose); and (4) the fermentation of pentose sugars (e.g., xylose and arabinose). These four transformations occur in a single step in a process configuration called consolidated bioprocessing (CBP), which is distinguished from other less integrated configurations in that it does not involve a dedicated process step for cellulase and/or hemicellulase production.

CBP offers the potential for lower cost and higher efficiency than processes featuring dedicated cellulase production. The benefits result in part from avoiding capital costs associated for example, with substrates, raw materials and utilities required for cellulase production. In addition, several factors support the realization of higher rates of hydrolysis, and hence reduced reactor volume and capital investment using CBP, including enzyme-microbe synergy and the use of thermophilic organisms and/or complexed cellulase systems. Moreover, cellulose-adherent cellulolytic microorganisms are likely to compete successfully for products of cellulose hydrolysis with non-adhered microbes, e.g., contaminants, which could increase the stability of industrial processes based on microbial cellulose utilization. Progress in developing CBP-enabling microorganisms is being made through two strategies: engineering naturally occurring cellulolytic microorganisms to improve product-related properties, such as yield and titer; and engineering non-cellulolytic organisms that exhibit high product yields and titers to express a heterologous cellulase and hemicellulase system enabling cellulose and hemicellulose utilization.

Three major types of enzymatic activities are required for native cellulose degradation: The first type are endoglucanases (1,4-β-D-glucan 4-glucanohydrolases; EC 3.2.1.4). Endoglucanases cut at random in the cellulose polysaccharide chain of amorphous cellulose, generating oligosaccharides of varying lengths and consequently new chain ends. The second type are exoglucanases, including cellodextrinases (1,4-β-D-glucan glucanohydrolases; EC 3.2.1.74) and cellobiohydrolases (1,4-β-D-glucan cellobiohydrolases; EC 3.2.1.91). Exoglucanases act in a processive manner on the reducing or non-reducing ends of cellulose polysaccharide chains, liberating either glucose (glucanohydrolases) or cellobiose (cellobiohydrolase) as major products. Exoglucanases can also act on microcrystalline cellulose, presumably peeling cellulose chains from the microcrystalline structure. The third type are β-glucosidases (β-glucoside glucohydrolases; EC 3.2.1.21). β-Glucosidases hydrolyze soluble cellodextrins and cellobiose to glucose units.

A variety of plant biomass resources are available as lignocellulosics for the production of biofuels, notably bioethanol. The major sources are (i) wood residues from paper mills, sawmills and furniture manufacturing, (ii) municipal solid wastes, (iii) agricultural residues and (iv) energy crops. Preconversion of particularly the cellulosic fraction in these biomass resources (using either physical, chemical or enzymatic processes) to fermentable sugars (glucose, cellobiose and cellodextrins) would enable their fermentation to bioethanol, provided the necessary fermentative micro-organism with the ability to utilize these sugars is used.

On a world-wide basis, $1.3 \times 10^{10}$ metric tons (dry weight) of terrestrial plants are produced annually (Demain, A. L., et al., *Microbiol. Mol. Biol. Rev.* 69, 124-154 (2005)). Plant biomass consists of about 40-55% cellulose, 25-50% hemicellulose and 10-40% lignin, depending whether the source is hardwood, softwood, or grasses (Sun, Y. and Cheng, J., *Bioresource Technol.* 83, 1-11 (2002)). The major polysaccharide present is water-insoluble, cellulose that contains the major fraction of fermentable sugars (glucose, cellobiose or cellodextrins).

Bakers' yeast (*Saccharomyces cerevisiae*) remains the preferred micro-organism for the production of ethanol (Hahn-Hägerdal, B., et al., *Adv. Biochem. Eng. Biotechnol.* 73, 53-84 (2001)). Attributes that favor use of this microbe are (i) high productivity at close to theoretical yields (0.51 g ethanol produced/g glucose used), (ii) high osmo- and ethanol tolerance, (iii) natural robustness in industrial processes, (iv) being generally regarded as safe (GRAS) due to its long association with wine and bread making, and beer brewing. Furthermore, *S. cerevisiae* exhibits tolerance to inhibitors commonly found in hydrolyzaties resulting from biomass pretreatment.

The major shortcoming of *S. cerevisiae* is its inability to utilize complex polysaccharides such as cellulose, or its break-down products, such as cellobiose and cellodextrins. In contrast, termites, with the help of microbial species that reside in their guts, are efficient at breaking down cellulose. However, whether or not termite cellulases could be expressed in yeast systems was not clear, as termite cellulases could be endogenous insect cellulases or symbiotic cellulases (bacterial, protist or other). The post-translational apparatuses in yeast and insects (e.g., the glycosylation machinery) are quite different, and thus it would not be expected that a termite protein could be properly expressed in yeast. As for bacterial symbiotic cellulases, it would be more predictable to express them in a bacterial host, such as *E. coli*. Therefore, to address the limitations of currently known bioprocessing systems, the present invention provides for the successful heterologous expression of termite cellulases and termite-associated symbiont cellulases in host cells, such as yeast, including *Saccharomyces cerevisiae*. The expression in such host cells is useful for efficient and cost-effective consolidated bioprocessing systems.

BRIEF SUMMARY OF THE INVENTION

The present invention provides for the heterologous expression of termite and termite-associated symbiont cellulases in yeast cells, for example, *Saccharomyces cerevisiae*.

In particular, the invention provides polynucleotides comprising a nucleic acid fragment which encodes at least 50 contiguous amino acids of a cellulase, wherein the nucleic acid fragment is codon-optimized for expression in a yeast strain and wherein the cellulase is a termite cellulase or a termite-associated symbiont cellulase. In some embodiments, the codon adaptation index (CAI) of the nucleic acid fragment is from about 0.6 to 1.0. In some embodiments, the CAI is from about 0.7 to about 0.9.

In some embodiments the yeast strain can be selected from the group consisting of *Saccharomyces cerevisiae, Kluveromyces lactus, Kluyveromyces marxianus, Schizzosaccharomyces pombe, Candida albicans, Pichia pastoris, Pichia Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In some embodiments, the yeast is *Saccharomyces cerevisiae*.

In further embodiments of the present invention, the cellulase has exogluconase activity. In other embodiments, the cellulase has endogluconase activity. In still further embodiments, the cellulase has both exogluconase and endogluconase activity.

In some embodiments, the cellulase is a protozoan cellulase. The cellulase can be, for example, a *Holomastigotoides mirabile, Reticulitermes speratus* symbiont, *Coptotermes lacteus* symbiont, *Reticulitermes speratus* symbiont, *Cryptocercus punctulatus* symbiont, *Mastotermes darwiniensis* symbiont, *Pseudotrichonympha grassii, Reticulitermes flavipes* gut symbiont, *Hodotermopsis sjoestedti* symbiont or *Neotermes koshunensis* symbiont cellulase. In other embodiments, the cellulase is a metazoan cellulase. For example, the cellulase can be a *Coptotermes formosanus, Nasutitermes takasagoensis, Coptotermes acinaciformis, Mastotermes darwinensis, Reticulitermes speratus, Reticulitermes flavipes, Nasutitermes walkeri* or *Panesthia cribrata* cellulase.

In other embodiments the cellulase is a bacterial cellulase, a fungal cellulase or a yeast cellulase.

In some embodiments of the invention, the polynucleotide encodes at least about 100 contiguous amino acids of a termite cellulase or a termite-associated symbiotic cellulase. In further embodiments, the nucleic acid fragment encodes at least about 200, 300 or 350 contiguous amino acids of a cellulase.

In some embodiments, the nucleotide has additional characteristics. For example, in some embodiments, the polynucleotide is a polynucleotide in which at least one nucleotide within a sequence of 4, 5, 6, 7, 8, 9 or 10 or more consecutive A, C, G or T nucleotides is replaced with a different nucleotide, wherein the nucleotide replacement does not alter the amino acid sequence encoded by the polynucleotide and wherein the nucleotide replacement creates a codon that is the second most frequently used codon to encode an amino acid in *Saccharomyces cerevisiae*.

In other embodiments, the polynucleotide is a polynucleotide in which at least one restriction enzyme site within the polynucleotide is removed by replacing at least one nucleotide within the restriction enzyme site with a different nucleotide, wherein the nucleotide replacement does not alter the amino acid sequence encoded by the polynucleotide and wherein the nucleotide replacement creates a codon that is the second most frequently used codon to encode an amino acid in *Saccharomyces cerevisiae*. The restriction site can be, for example, a PacI, AscI, BamHI, BglII, EcoRI or XhoI restriction site.

In yet another embodiment, the polynucleotide is a polynucleotide in which one or more direct repeats, inverted repeats and mirror repeats with lengths of about 5, 6, 7 8, 9 or 10 bases or longer within said polynucleotide is altered by replacing at least one nucleotide within the repeat with a different nucleotide, wherein the nucleotide replacement does not alter the amino acid sequence encoded by the polynucleotide and wherein the nucleotide replacement creates a codon that is the second most frequently used codon to encode an amino acid in *Saccharomyces cerevisiae*.

In some embodiments, the polynucleotide of the invention is operably associated with a heterologous nucleic acid. For example, the heterologous nucleic acid can encode a signal peptide, and the signal peptide can be, for example, the *S. cerevisiae* alpha mating factor signal sequence. Additionally, and/or alternatively, the heterologous polynucleotide can encode a cellulose binding domain. The cellulose binding domain can be, for example, the cellulose binding domain of *T. reesei* Cbh1 or Cbh2. In some embodiments, the polynucleotide and the heterologous nucleic acid encode a fusion protein, which can be fused for example, via a linker sequence.

In some embodiments, the polynucleotide is at least about 70%, at least about 75%, at least about 80%, at least about 85%, at least about 90% or at least about 95% identical to a sequence selected from the group consisting of SEQ ID NO:1-20.

The invention further provides vectors comprising a polynucleotide as set forth above. The vectors can also comprise one or more additional polynucleotides. The one or more additional polynucleotides can encode, for example, one or more cellulases, and the one or more cellulases can be, for example, one or more endogluconases (e.g. endogluconase I), one or more exogluconases (e.g. cellobiohydrolase I or cellobiohydrolase II) or one or more β-glucosidases (e.g. β-glucosidase I). In some embodiments, the one or more polynucleotides can encode one or more cellulases from another organism, e.g. a *T. reesei, S. fibuligera* or *T. emersonii* cellulase. In other embodiments, the one or more additional polynucleotides can encode one or more additional termite or termite-associated symbiont cellulases. In some embodiments, the one or more additional polynucleotides can encode a cellulose binding domain. The cellulase binding domain can be, for example, the cellulose binding domain of *T. reesei* Cbh1 or Cbh2.

In some embodiments of the invention, the one or more additional polynucleotides in the vector can be in the forward orientation relative to the first polynucleotide. In some embodiments, the one or more additional polynucleotides can be in the reverse orientation relative to the first polynucleotide. In some embodiments, the first and additional polynucleotide(s) are operably associated by a linker sequence. In some embodiments, the one or more additional polynucleotides is at the 5' end of the first polynucleotide. In some embodiments, the one or more additional polynucleotides is at the 3' end of the first polynucleotide.

In some embodiments of the present invention, the vector is a plasmid. For example, the plasmid can be a yeast episomal plasmid or a yeast integrating plasmid.

In other embodiments of the present invention the first and additional polynucleotides are contained in a single linear DNA construct. The first and additional polynucleotides in the linear DNA construct can be in the same or different expression cassette.

The present invention also provides for host cells comprising a polynucleotide encoding at least 50 contiguous amino acids of a heterologous cellulase, wherein the heterologous cellulase is a termite cellulase or a termite-associated symbiotic cellulase, wherein the host cell is a yeast cell and wherein the heterologous cellulase is expressed.

The host cell can comprise a termite or termite-associated symbiont cellulase with exogluconase activity, a termite or termite-associated symbiont cellulase with endogluconase activity and/or a termite or termite-associated symbiont cellulase with both exogluconase activity and endogluconase activity. In further embodiments, the host cell comprises a termite or termite-associated symbiont cellulase with β-glucosidase activity.

The host cells of the present invention can comprise a protozoan cellulase, for example, a *Holomastigotoides mirabile, Reticulitermes speratus* symbiont, *Coptotermes lacteus* symbiont, *Reticulitermes speratus* symbiont, *Cryptocercus punctulatus* symbiont, *Mastotermes darwiniensis* symbiont, *Pseudotrichonympha grassii, Reticulitermes flavipes* gut symbiont, *Hodotermopsis sjoestedti* symbiont or *Neotermes koshunensis* symbiont cellulase. Alternatively and/or additionally, the host cells can also comprise a metazoan cellulase, for example a *Coptotermes formosanus, Nasutitermes takasagoensis, Coptotermes acinaciformis, Mastotermes darwinensis, Reticulitermes speratus, Reticulitermes flavipes, Nasutitermes walkeri* or *Panesthia cribrata* cellulase.

The host cells of the invention can comprise one or more cellulases encoded by a polynucleotide comprising a sequence selected from the group consisting of SEQ ID NOs: 1-20. The host cells can comprise one or more cellulases comprising the amino acid sequences of SEQ ID NOs: 21-40. The host cell can contain a polynucleotide encoding a termite or termite-associated symbiont cellulase that is codon-optimized for expression in yeast. The host cell can also comprise a vector comprising a polynucleotide encoding a termite or termite-associated symbiont cellulase that is codon-optimized for expression in yeast.

In some embodiments, the host cell comprises a termite or termite-associated symbiont cellulase that is tethered to the cell surface when expressed. In addition, the host cells can comprise a termite or termite-associated symbiont cellulase that is secreted by the cell.

In some embodiments, the host cell is a yeast selected from the group consisting of *Saccharomyces cerevisiae, Kluveromyces lactus, Kluyveromyces marxianus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe* and *Schwanniomyces occidentalis*. In one particular embodiment, the yeast is *Saccharomyces cerevisiae*.

In some embodiments of the present invention, the host cell comprises one or more polynucleotides encoding one or more heterologous cellulases. The one or more polynucleotides can, for example, encode one or more endogluconases (e.g. endogluconase I), one or more exogluconases (e.g. cellobiohydrolase I or cellobiohydrolase II) and/or one or more β-glucosidases (e.g. β-glucosidase I).

In some embodiments, the one or more heterologous cellulases in the host cell is a *T. reesei, S. fibuligera* and/or *T. emersonii* cellulase. In addition, the one or more heterologous cellulases can be a termite cellulase or a termite-associated symbiont cellulase. In some embodiments, the one or more heterologous cellulases is encoded by a polynucleotide selected from the polynucleotides of SEQ ID NOs: 1-20. In some embodiments, the one or more heterologous cellulases is a protein which comprises an amino acid sequence selected from SEQ ID NOs: 21-40.

In other aspects the invention encompasses host cells comprising one or more termite cellulases or termite-associate symbiont cellulases wherein at least one heterologous cellulase is tethered to the cell surface when expressed. In other embodiments, at least one heterologous cellulase is secreted by the cell. In still further embodiments, at least one heterologous cellulase is tethered to the cell surface and at least one heterologous cellulase is secreted by the cell.

The invention also provides for host cells, wherein the host cells have the ability to saccharify crystalline cellulose. In additional embodiments, the host cells also have the ability to ferment crystalline cellulose.

Furthermore, the invention provides methods of using the polynucleotides, vectors, polypeptides and host cells of the invention. For example, the invention provides a method for hydrolyzing a cellulosic substrate, comprising contacting the cellulosic substrate with a host cell of the invention. In some embodiments, the cellulosic substrate comprises a lignocellulosic biomass selected from the group consisting of grass, switch grass, cord grass, rye grass, reed canary grass, miscanthus, sugar-processing residues, sugarcane bagasse, agricultural wastes, rice straw, rice hulls, barley straw, corn cobs, cereal straw, wheat straw, canola straw, oat straw, oat hulls, corn fiber, stover, soybean stover, corn stover, forestry wastes, recycled wood pulp fiber, paper sludge, sawdust, hardwood, softwood, and combinations thereof.

In addition, the invention also provides a method of fermenting cellulose using the host cells of the invention. The method comprises culturing a host cell in medium that contains crystalline cellulose under suitable conditions for a period sufficient to allow saccharification and fermentation of the cellulose. In still further embodiments, the host cell produces ethanol.

BRIEF DESCRIPTION OF THE DRAWINGS/FIGURES

FIG. 1 depicts a plasmid map of pMU451. Synthetic termite cellulase genes were inserted into the PacI/AscI sites. "S.cer ENO1 pr" and "S.cer ENO ter" indicate the *S. cerevisiae* ENO1 promoter and terminator sequences respectively. "S.cer URA3" indicates the *S. cerevisiae* URA3 auxotrophic marker. "2 mu ori" indicates the *S. cerevisiae* 2 mu plasmid origin of replication sequence. "Bla(AmpR)" indicates the Amp resistance sequence, and "pBR322 ori" indicates the *E. coli* pB322 plasmid origin of replication sequence.

Figure 2:
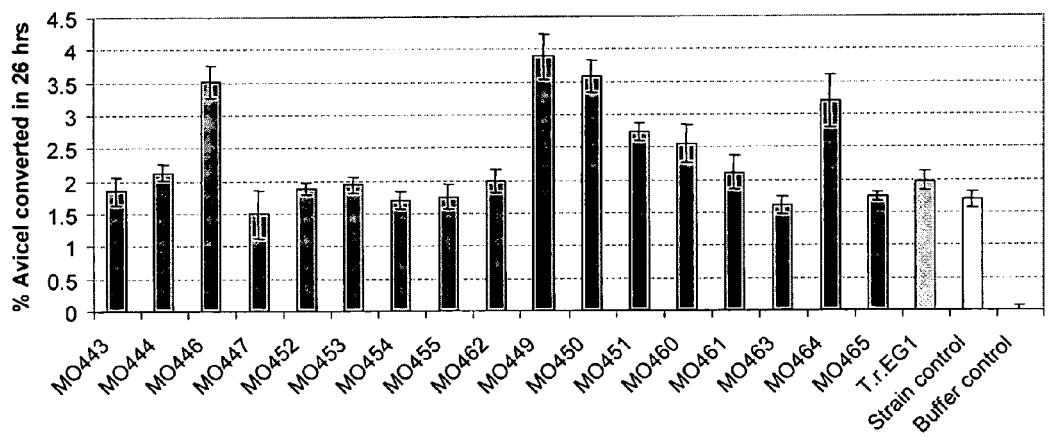

FIG. 2 depicts a bar graph showing Avicel conversion by supernatants of *S. cerevisiae* strains expressing termite cellulase genes. "Strain control" indicates MO375 strain transformed with empty pMU451 vector (negative control). "T.r.EG1" indicates MO375 transformed with *T. reesei* endogluconase 1 (EG1) in pMU451 vector (positive control). Numbering of other strains is according to numbering shown in Table 5. "Buffer control" indicates the condition in which Avicel conversion assay reaction buffer was used instead of yeast culture supernatant.

Figure 3:
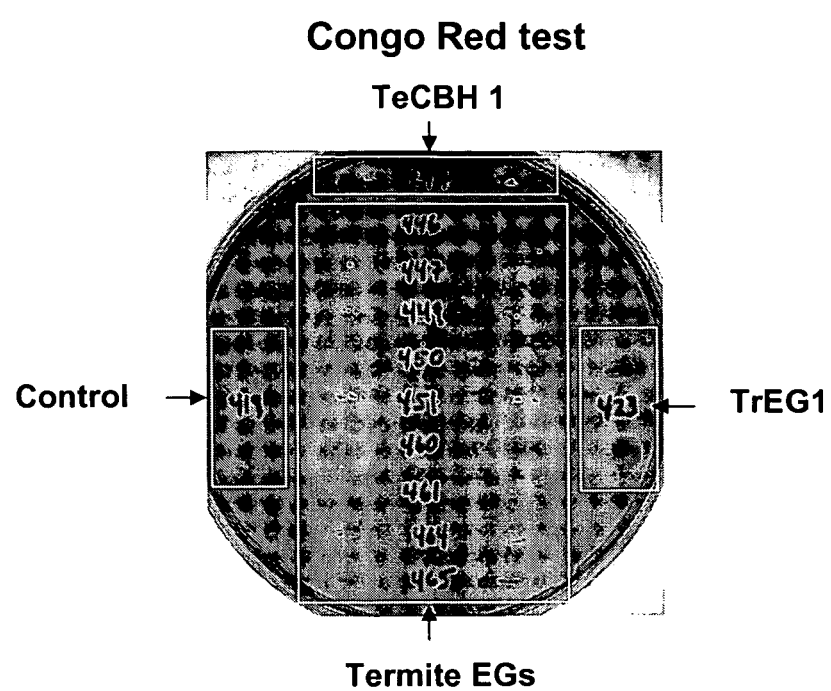

FIG. 3 depicts an image of a Congo Red test performed on *S. cerevisiae* expressing termite cellulase or termite-associated symbiotic protozoan cellulase genes. "MO419" indicates MO375 strain transformed with empty pMU451 vector (negative control). "MO423" indicates MO375 transformed with *T. reesei* EG1 in pMU451 vector (positive control). "MO247" indicates Y294 strain with fur1 gene knocked out (to stabilize the episomal plasmid) and expressing *T. emersonii* CBH1 in a vector similar to pMU451. "MO449" corresponds to MO375 transformed with *Coptotermes formosanus* EG (CfEG). Numbering of other strains is according to numbering shown in Table 5.

Figure 4:
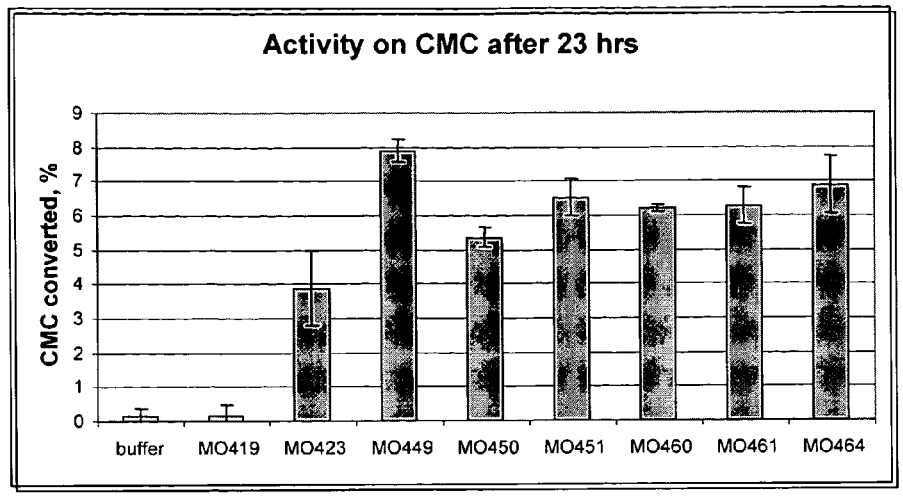

FIG. 4 depicts a bar graph showing results of a carboxymethyl-cellulose (CMC) conversion assay using *S. cerevisiae* expressing termite cellulase genes. "MO419" indicates MO375 strain transformed with empty vector (negative control). "MO423" indicates MO375 transformed with T. reesei EG1 (positive control). Numbering of other strains is according to numbering shown in Table 5. "Buffer control" indicates the condition in which buffer was used instead of yeast culture supernatant.

Figure 5:
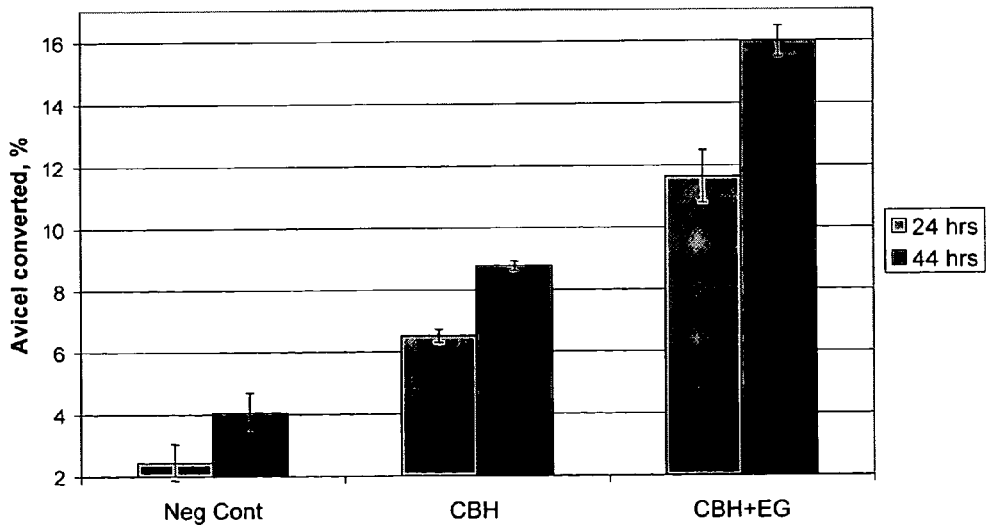

FIG. 5 depicts a bar graph showing the effect of addition of yeast made termite CfEG to yeast made fungal CBHs on crystalline cellulose conversion measured by Avicel assay. "Neg Cont" is the negative control and corresponds to 300 µl of parental non-cellulytic M0509 strain supernatant; "CBH" corresponds to 100 ul of CBH mix (M0579 and M0969 samples mixed at ratio 4:1) added to 200 µl of control M0509 supernatant; "CBH+EG" corresponds to 100 µl of CBH mix added to 200 µl of M0968 supernatant (CfEG). All measurements were done in quadruplicates. The samples and strains are also described in Table 6 below.

Figure 6:
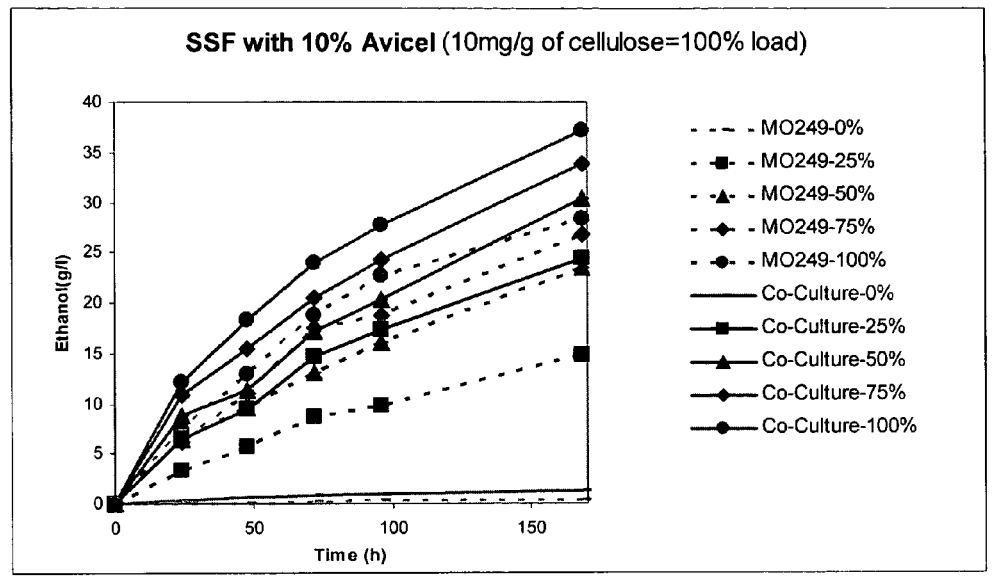

FIG. 6 depicts a graph showing the results of SSF ethanol production of co-cultured cellulytic yeast strains at different external enzyme loads compared to the control non-cellulytic strain MO249. 100% of external cellulase load corresponds to 10 mg of enzyme per gram of Avicel.

Figure 7:
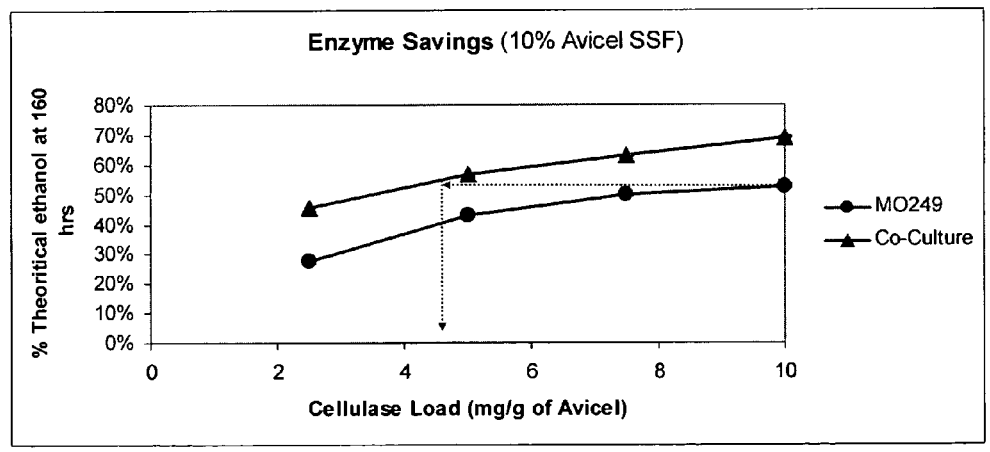

FIG. 7 depicts a graph showing the theoretical ethanol yield at 160 hrs of SSF plotted against external cellulase loads. The co-culture contains strains MO595, 563, 592, 566; MO249 is the control non-cellulytic strain.

Figure 8:
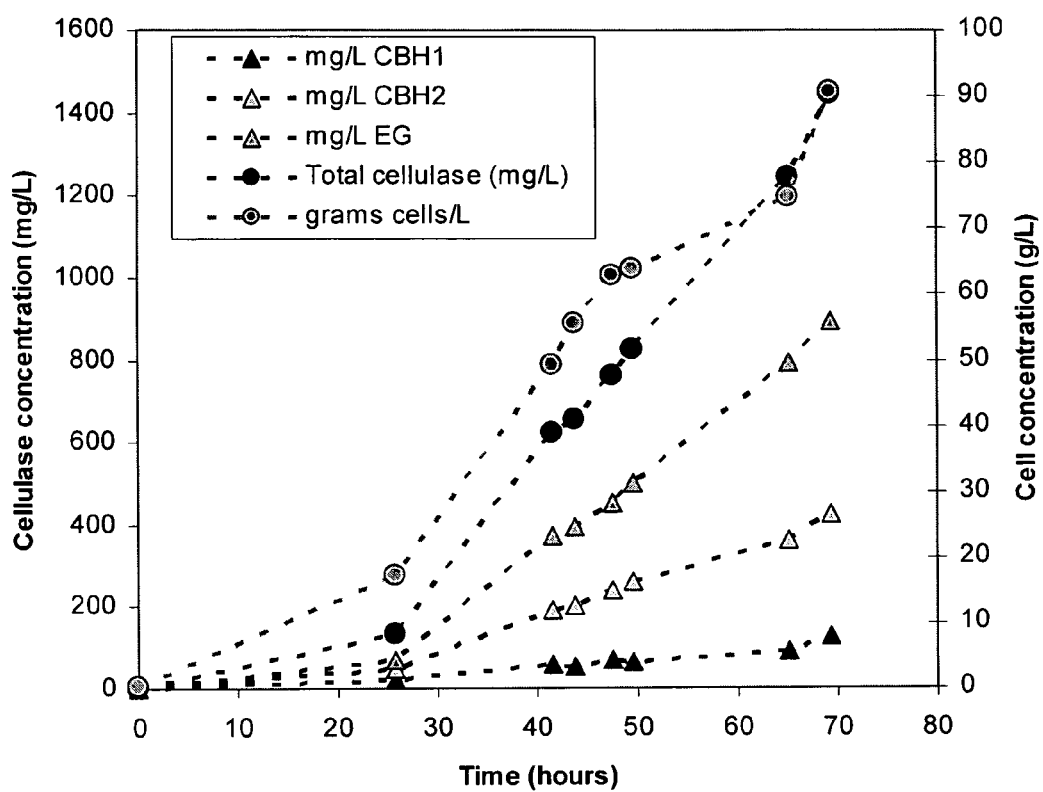

FIG. 8 depicts a graph showing results for cellulase production by yeast in a bioreactor. Strain M0712 was batch cultivated in YPD-based rich media with 50 g/L, glucose in 1 L bioreactor for 24 hours, followed by a stepped feed of 50% glucose with vitamins and trace elements for another 36 hours. At several time points, reactor samples were taken and the dry cell weight was measured. Additionally, the protein concentration for each cellulase was measured by HPLC.

Figure 9:
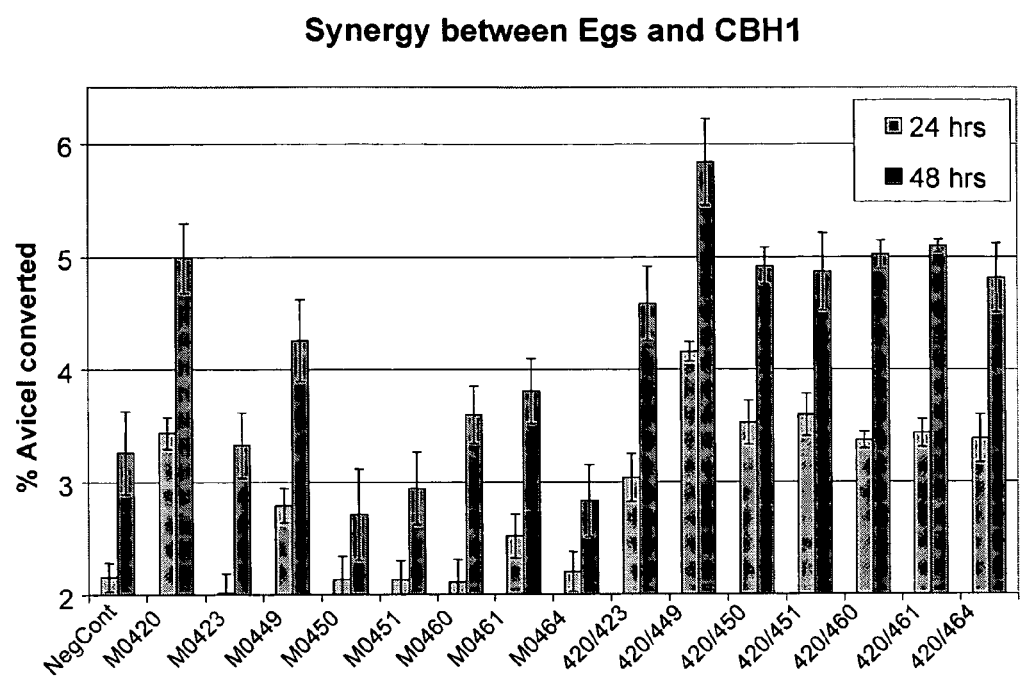

FIG. 9 depicts a graph showing results from an Avicel conversion assay utilizing supernatants of S. cerevisiae strains expressing termite cellulase genes in synergy with a yeast-made T. emersonii CBH1 (strain M0420). "NegCont" corresponds to the negative control MO375 strain transformed with empty pMU451 vector. "MO423" corresponds to the MO375 strain transformed with T. reesei endoglucanase 1 (EG1) in the pMU451 vector (positive control). The other numbered strains are described in Table 5 below. For single strains, 300 µl or supernatant was used; for the combined samples 150 µl of each supernatant was used. For example, "420/423" means that 150 µl of the M0420 strain supernatant was mixed with 150 µl of the M0423 supernatant.

DETAILED DESCRIPTION OF THE INVENTION

The present invention relates to, inter alia, the heterologous expression of termite cellulases and termite-associated symbiont cellulases in host cells, including yeast, e.g., *Saccharomyces cerevisiae*. The present invention provides important tools to enable growth of yeast on cellulosic substrates for ethanol production.

Definitions

A "vector," e.g., a "plasmid" or "YAC" (yeast artificial chromosome) refers to an extrachromosomal element often carrying one or more genes that are not part of the central metabolism of the cell, and is usually in the form of a circular double-stranded DNA molecule. Such elements may be autonomously replicating sequences, genome integrating sequences, phage or nucleotide sequences, linear, circular, or supercoiled, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. Preferably, the plasmids or vectors of the present invention are stable and self-replicating.

An "expression vector" is a vector that is capable of directing the expression of genes to which it is operably associated.

The term "heterologous" as used herein refers to an element of a vector, plasmid or host cell that is derived from a source other than the endogenous source. Thus, for example, a heterologous sequence could be a sequence that is derived from a different gene or plasmid from the same host, from a different strain of host cell, or from an organism of a different taxonomic group (e.g., different kingdom, phylum, class, order, family genus, or species, or any subgroup within one of these classifications). The term "heterologous" is also used synonymously herein with the term "exogenous."

The term "domain" as used herein refers to a part of a molecule or structure that shares common physical or chemical features, for example hydrophobic, polar, globular, helical domains or properties, e.g., a DNA binding domain or an ATP binding domain. Domains can be identified by their homology to conserved structural or functional motifs. Examples of cellulase domains include the catalytic domain (CD) and the cellulose binding domain (CBD).

A "nucleic acid," "polynucleotide," or "nucleic acid molecule" is a polymeric compound comprised of covalently linked subunits called nucleotides. Nucleic acid includes polyribonucleic acid (RNA) and polydeoxyribonucleic acid (DNA), both of which may be single-stranded or double-stranded. DNA includes cDNA, genomic DNA, synthetic DNA, and semi-synthetic DNA.

An "isolated nucleic acid molecule" or "isolated nucleic acid fragment" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules (e.g., restriction fragments), plasmids, and chromosomes. In discussing the structure of particular double-stranded DNA molecules, sequences may be described herein according to the normal convention of giving only the sequence in the 5' to 3' direction along the non-transcribed strand of DNA (i.e., the strand having a sequence homologous to the mRNA).

A "gene" refers to an assembly of nucleotides that encode a polypeptide, and includes cDNA and genomic DNA nucleic acids. "Gene" also refers to a nucleic acid fragment that expresses a specific protein, including intervening sequences (introns) between individual coding segments (exons), as well as regulatory sequences preceding (5' non-coding sequences) and following (3' non-coding sequences) the coding sequence. "Native gene" refers to a gene as found in nature with its own regulatory sequences.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified, e.g., in Sambrook, J., Fritsch, E. F. and Maniatis, T. MOLECULAR CLONING: A LABORATORY MANUAL, Second Edition, Cold Spring Harbor Laboratory Press, Cold Spring Harbor (1989), particularly Chapter 11 and Table 11.1 therein (hereinafter "Maniatis", entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. For more stringent conditions, washes are performed at higher temperatures in which the washes are identical to those above except for the temperature of the final two 30 min washes in 0.2×SSC, 0.5% SDS are increased to 60° C. Another set of highly stringent conditions uses two final washes in 0.1×SSC, 0.1% SDS at 65° C. An additional set of highly stringent conditions are defined by hybridization at 0.1×SSC, 0.1% SDS, 65° C. and washed with 2×SSC, 0.1% SDS followed by 0.1×SSC, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see, e.g., Maniatis at 9.50-9.51). For hybridizations with shorter nucleic acids, i.e., oligonucleotides, the position of mismatches becomes more important, and the length of the oligonucleotide determines its specificity (see, e.g., Maniatis, at 11.7-11.8). In one embodiment the length for a hybridizable nucleic acid is at least about 10 nucleotides. Preferably a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences.

As known in the art, "similarity" between two polypeptides is determined by comparing the amino acid sequence and conserved amino acid substitutes thereto of the polypeptide to the sequence of a second polypeptide.

Suitable nucleic acid sequences or fragments thereof (isolated polynucleotides of the present invention) encode polypeptides that are at least about 70% to 75% identical to the amino acid sequences reported herein, at least about 80%, 85%, or 90% identical to the amino acid sequences reported herein, or at least about 95%, 96%, 97%, 98%, 99%, or 100% identical to the amino acid sequences reported herein. Suitable nucleic acid fragments are at least about 70%, 75%, or 80% identical to the nucleic acid sequences reported herein, at least about 80%, 85%, or 90% identical to the nucleic acid sequences reported herein, or at least about 95%, 96%, 97%, 98%, 99%, or 100% identical to the nucleic acid sequences reported herein. Suitable nucleic acid fragments not only have the above identities/similarities but typically encode a polypeptide having at least 50 amino acids, at least 100 amino acids, at least 150 amino acids, at least 200 amino acids, or at least 250 amino acids.

The term "probe" refers to a single-stranded nucleic acid molecule that can base pair with a complementary single stranded target nucleic acid to form a double-stranded molecule.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

As used herein, the term "oligonucleotide" refers to a nucleic acid, generally of about 18 nucleotides, that is hybridizable to a genomic DNA molecule, a cDNA molecule, or an mRNA molecule. Oligonucleotides can be labeled, e.g., with 32P-nucleotides or nucleotides to which a label, such as biotin, has been covalently conjugated. An oligonucleotide can be used as a probe to detect the presence of a nucleic acid according to the invention. Similarly, oligonucleotides (one or both of which may be labeled) can be used as PCR primers, either for cloning full length or a fragment of a nucleic acid of the invention, or to detect the presence of nucleic acids according to the invention. Generally, oligonucleotides are prepared synthetically, preferably on a nucleic acid synthesizer. Accordingly, oligonucleotides can be prepared with non-naturally occurring phosphoester analog bonds, such as thioester bonds, etc.

A DNA or RNA "coding region" is a DNA or RNA molecule which is transcribed and/or translated into a polypeptide in a cell in vitro or in vivo when placed under the control of appropriate regulatory sequences. "Suitable regulatory regions" refer to nucleic acid regions located upstream (5' non-coding sequences), within, or downstream (3' non-coding sequences) of a coding region, and which influence the transcription, RNA processing or stability, or translation of the associated coding region. Regulatory regions may include promoters, translation leader sequences, RNA processing site, effector binding site and stem-loop structure. The boundaries of the coding region are determined by a start codon at the 5' (amino) terminus and a translation stop codon at the 3' (carboxyl) terminus. A coding region can include, but is not limited to, prokaryotic regions, cDNA from mRNA, genomic DNA molecules, synthetic DNA molecules, or RNA molecules. If the coding region is intended for expression in a eukaryotic cell, a polyadenylation signal and transcription termination sequence will usually be located 3' to the coding region.

"Open reading frame" is abbreviated ORF and means a length of nucleic acid, either DNA, cDNA or RNA, that comprises a translation start signal or initiation codon, such as an ATG or AUG, and a termination codon and can be potentially translated into a polypeptide sequence.

"Promoter" refers to a DNA fragment capable of controlling the expression of a coding sequence or functional RNA. In general, a coding region is located 3' to a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity. A promoter is generally bounded at its 3' terminus by the transcription initiation site and extends upstream (5' direction) to include the minimum number of bases or elements necessary to initiate transcription at levels detectable above background. Within the promoter will be found a transcription initiation site (conveniently defined for example, by mapping with nuclease Si), as well as protein binding domains (consensus sequences) responsible for the binding of RNA polymerase.

A coding region is "under the control" of transcriptional and translational control elements in a cell when RNA polymerase transcribes the coding region into mRNA, which is then trans-RNA spliced (if the coding region contains introns) and translated into the protein encoded by the coding region.

"Transcriptional and translational control regions" are DNA regulatory regions, such as promoters, enhancers, terminators, and the like, that provide for the expression of a coding region in a host cell. In eukaryotic cells, polyadenylation signals are control regions.

The term "operably associated" refers to the association of nucleic acid sequences on a single nucleic acid fragment so that the function of one is affected by the other. For example, a promoter is operably associated with a coding region when it is capable of affecting the expression of that coding region (i.e., that the coding region is under the transcriptional control of the promoter). Coding regions can be operably associated to regulatory regions in sense or antisense orientation.

The term "expression," as used herein, refers to the transcription and stable accumulation of sense (mRNA) or antisense RNA derived from the nucleic acid fragment of the invention. Expression may also refer to translation of mRNA into a polypeptide.

Termite Cellulases and Termite-Associated Symbiont Cellulases

Termite guts have been referred to as tiny bioreactors due to their efficiency at lignocellulose digestion. This efficiency can be attributed not only to the activity of cellulases encoded by the termite genome, but also to the microbes that populate termite guts. The present invention provides for the use of both termite cellulases (i.e. cellulases that are expressed endogenously in termite cells) and termite-associated symbiont cellulases (i.e. cellulases that are expressed by symbiotic organisms found in termite guts).

In some embodiments of the present invention, the cellulase is a termite cellulase. The termite can be, for example, a higher termite, i.e. a termite from the family Termitidae. The termite of can also be a lower termite. For example, the lower termite can be a Mastotermiitidae, Hodotermitidae, Termopsidae, Kalotermitidae, Rhinotermitidae or Serritermitidae. In some embodiments, the termite is selected from the group consisting of *Coptotermes formosanus*, *Nasutitermes takasagoensis*, *Coptotermes acinaciformis*, *Mastotermes darwinensis*, *Reticulitermes speratus*, *Reticulitermes flavipes*, *Nasutitermes walkeri* and *Panesthia cribrata*.

According to the present invention, the cellulase can also be from a termite-associated symbiont. The termite-associated symbiont can be, for example, a fungal symbiont, a yeast symbiont, a bacterial symbiont or a protozoan symbiont. The bacterial symbiont can be, for example, fibroacters or spirochetes. The protozoan symbiont can be, for example, a flagellated protozoan. In some embodiments, the protozoan symbiont is an actinomycete. In some embodiments, the protozoan symbiont is selected from the group consisting of *Holomastigotoides mirabile*, *Reticulitermes speratus* symbiont, *Coptotermes lacteus* symbiont, *Reticulitermes speratus* symbiont, *Cryptocercus punctulatus* symbiont, *Mastotermes darwiniensis* symbiont, *Pseudotrichonympha grassii*, *Reticulitermes flavipes* gut symbiont, *Hodotermopsis sjoestedti* symbiont and *Neotermes koshunensis* symbiont.

In some embodiments of the present invention, the cellulase has endogluconase activity. In some embodiments, the cellulase has exogluconase activity. In some embodiments, the cellulase has both exogluconase and endogluconase activity. In some embodiments of the invention, the cellulase has β-glucosidase activity. Endogluconase, exogluconase and β-glucosidase activity can be determined using any method known in the art. For example, CMC conversion assays are commonly used to assess endogluconase activity, and Avicel conversion assays are commonly used to assess exogluconase activity.

Codon Optimization

According to the present invention, sequences encoding cellulases can be codon optimized. As used herein the term "codon optimized" refers to a nucleic acid that has been adapted for expression in the cells of a given organism by replacing at least one, or more than one, or a significant number, of codons with one or more codons that are more frequently used in the genes of that organism.

In general, highly expressed genes in an organism are biased towards codons that are recognized by the most abundant tRNA species in that organism. One measure of this bias is the "codon adaptation index" or "CM," which measures the extent to which the codons used to encode each amino acid in a particular gene are those which occur most frequently in a reference set of highly expressed genes from an organism. The Codon Adaptation Index is described in more detail in Sharp and Li, *Nucleic Acids Research* 15: 1281-1295 (1987)), which is incorporated by reference herein in its entirety.

The CAI of codon optimized sequences of the present invention can be from about 0.5 to 1.0, from about 0.6 to 1.0, from about 0.7 to 1.0, from about 0.75 to 1.0, from about 0.8 to 1.0 or from about 0.9 to 1.0. In some embodiments, the CM of the codon optimized sequences of the present invention corresponds to from about 0.5 to about 0.9, from about 0.7 to about 0.9, from about 0.6 to about 0.8, from about 0.7 to about 0.8 or from about 0.75 to about 0.8.

A codon optimized sequence may be further modified for expression in a particular organism, depending on that organism's biological constraints. For example, large runs of "As"

or "Ts" (e.g., runs greater than 3, 4, 5, 6, 7, 8, 9, or 10 consecutive bases) can effect transcription negatively. Therefore, it can be useful to remove a run by, for example, replacing at least one nucleotide in the run with another nucleotide. Furthermore, specific restriction enzyme sites may be removed for molecular cloning purposes by replacing at least one nucleotide in the restriction site with another nucleotide. Examples of such restriction enzyme sites include PacI, AscI, BamHI, BglII, EcoRI and XhoI. Additionally, the DNA sequence can be checked for direct repeats, inverted repeats and mirror repeats with lengths of about 5, 6, 7, 8, 9 or 10 bases or longer. Runs of "As" or "Ts", restriction sites and/or repeats can be modified by replacing at least one codon within the sequence with the "second best" codons, i.e., the codon that occurs at the second highest frequency for a particular amino acid within the particular organism for which the sequence is being optimized.

Deviations in the nucleotide sequence that comprise the codons encoding the amino acids of any polypeptide chain allow for variations in the sequence coding for the gene. Since each codon consists of three nucleotides, and the nucleotides comprising DNA are restricted to four specific bases, there are 64 possible combinations of nucleotides, 61 of which encode amino acids (the remaining three codons encode signals ending translation). The "genetic code" which shows which codons encode which amino acids is reproduced herein as Table 1. As a result, many amino acids are designated by more than one codon. For example, the amino acids alanine and proline are coded for by four triplets, serine and arginine by six triplets each, whereas tryptophan and methionine are coded for by just one triplet. This degeneracy allows for DNA base composition to vary over a wide range without altering the amino acid sequence of the proteins encoded by the DNA.

TABLE 1

The Standard Genetic Code

| | T | C | A | G |
|---|---|---|---|---|
| T | TTT Phe (F) | TCT Ser (S) | TAT Tyr (Y) | TGT Cys (C) |
| | TTC Phe (F) | TCC Ser (S) | TAC Tyr (Y) | TGC |
| | TTA Leu (L) | TCA Ser (S) | TAA Ter | TGA Ter |
| | TTG Leu (L) | TCG Ser (S) | TAG Ter | TGG Trp (W) |
| C | CTT Leu (L) | CCT Pro (P) | CAT His (H) | CGT Arg (R) |
| | CTC Leu (L) | CCC Pro (P) | CAC His (H) | CGC Arg (R) |
| | CTA Leu (L) | CCA Pro (P) | CAA Gln (Q) | CGA Arg (R) |
| | CTG Leu (L) | CCG Pro (P) | CAG Gln (Q) | CGG Arg (R) |
| A | ATT Ile (I) | ACT Thr (T) | AAT Asn (N) | AGT Ser (S) |
| | ATC Ile (I) | ACC Thr (T) | AAC Asn (N) | AGC Ser (S) |
| | ATA Ile (I) | ACA Thr (T) | AAA Lys (K) | AGA Arg (R) |
| | ATG Met (M) | ACG Thr (T) | AAG Lys (K) | AGG Arg (R) |
| G | GTT Val (V) | GCT Ala (A) | GAT Asp (D) | GGT Gly (G) |
| | GTC Val (V) | GCC Ala (A) | GAC Asp (D) | GGC Gly (G) |
| | GTA Val (V) | GCA Ala (A) | GAA Glu (E) | GGA Gly (G) |
| | GTG Val (V) | GCG Ala (A) | GAG Glu (E) | GGG Gly (G) |

Many organisms display a bias for use of particular codons to code for insertion of a particular amino acid in a growing peptide chain. Codon preference or codon bias, differences in codon usage between organisms, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, genes can be tailored for optimal gene expression in a given organism based on codon optimization.

Given the large number of gene sequences available for a wide variety of animal, plant and microbial species, it is possible to calculate the relative frequencies of codon usage. Codon usage tables are readily available, for example, at http://phenotype.biosci.umbc.edu/codon/sgd/index.php (visited May 7, 2008) or at http://www.kazusa.or.jp/codon/ (visited Mar. 20, 2008), and these tables can be adapted in a number of ways. See Nakamura, Y., et al. "Codon usage tabulated from the international DNA sequence databases: status for the year 2000" *Nucl. Acids Res.* 28:292 (2000). Codon usage tables for yeast, calculated from GenBank Release 128.0 [15 Feb. 2002], are reproduced below as Table 2. This table uses mRNA nomenclature, and so instead of thymine (T) which is found in DNA, the tables use uracil (U) which is found in RNA. The Table has been adapted so that frequencies are calculated for each amino acid, rather than for all 64 codons.

TABLE 2

Codon Usage Table for *Saccharomyces cerevisiae* Genes

| Amino Acid | Codon | Number | Frequency per hundred |
|---|---|---|---|
| Phe | UUU | 170666 | 26.1 |
| Phe | UUC | 120510 | 18.4 |
| Leu | UUA | 170884 | 26.2 |
| Leu | UUG | 177573 | 27.2 |
| Leu | CUU | 80076 | 12.3 |
| Leu | CUC | 35545 | 5.4 |
| Leu | CUA | 87619 | 13.4 |
| Leu | CUG | 68494 | 10.5 |
| Ile | AUU | 196893 | 30.1 |
| Ile | AUC | 112176 | 17.2 |
| Ile | AUA | 116254 | 17.8 |
| Met | AUG | 136805 | 20.9 |
| Val | GUU | 144243 | 22.1 |
| Val | GUC | 76947 | 11.8 |
| Val | GUA | 76927 | 11.8 |
| Val | GUG | 70337 | 10.8 |
| Ser | UCU | 153557 | 23.5 |
| Ser | UCC | 92923 | 14.2 |
| Ser | UCA | 122028 | 18.7 |
| Ser | UCG | 55951 | 8.6 |
| Ser | AGU | 92466 | 14.2 |
| Ser | AGC | 63726 | 9.8 |
| Pro | CCU | 88263 | 13.5 |
| Pro | CCC | 44309 | 6.8 |
| Pro | CCA | 119641 | 18.3 |
| Pro | CCG | 34597 | 5.3 |
| Thr | ACU | 132522 | 20.3 |
| Thr | ACC | 83207 | 12.7 |
| Thr | ACA | 116084 | 17.8 |
| Thr | ACG | 52045 | 8.0 |
| Ala | GCU | 138358 | 21.2 |
| Ala | GCC | 82357 | 12.6 |
| Ala | GCA | 105910 | 16.2 |
| Ala | GCG | 40358 | 6.2 |
| Tyr | UAU | 122728 | 18.8 |
| Tyr | UAC | 96596 | 14.8 |
| His | CAU | 89007 | 13.6 |
| His | CAC | 50785 | 7.8 |
| Gln | CAA | 178251 | 27.3 |
| Gln | CAG | 79121 | 12.1 |
| Asn | AAU | 233124 | 35.7 |
| Asn | AAC | 162199 | 24.8 |
| Lys | AAA | 273618 | 41.9 |
| Lys | AAG | 201361 | 30.8 |
| Asp | GAU | 245641 | 37.6 |
| Asp | GAC | 132048 | 20.2 |
| Glu | GAA | 297944 | 45.6 |
| Glu | GAG | 125717 | 19.2 |
| Cys | UGU | 52903 | 8.1 |
| Cys | UGC | 31095 | 4.8 |
| Trp | UGG | 67789 | 10.4 |
| Arg | CGU | 41791 | 6.4 |
| Arg | CGC | 16993 | 2.6 |

TABLE 2-continued

Codon Usage Table for *Saccharomyces cerevisiae* Genes

| Amino Acid | Codon | Number | Frequency per hundred |
|---|---|---|---|
| Arg | CGA | 19562 | 3.0 |
| Arg | CGG | 11351 | 1.7 |
| Arg | AGA | 139081 | 21.3 |
| Arg | AGG | 60289 | 9.2 |
| Gly | GGU | 156109 | 23.9 |
| Gly | GGC | 63903 | 9.8 |
| Gly | GGA | 71216 | 10.9 |
| Gly | GGG | 39359 | 6.0 |
| Stop | UAA | 6913 | 1.1 |
| Stop | UAG | 3312 | 0.5 |
| Stop | UGA | 4447 | 0.7 |

By utilizing this or similar tables, one of ordinary skill in the art can apply the frequencies to any given polypeptide sequence, and produce a nucleic acid fragment of a codon-optimized coding region which encodes the polypeptide, but which uses codons optimal for a given species. Codon-optimized coding regions can be designed by various different methods.

In one method, a codon usage table is used to find the single most frequent codon used for any given amino acid, and that codon is used each time that particular amino acid appears in the polypeptide sequence. For example, referring to Table 2 above, for leucine, the most frequent codon is UUG, which is used 27.2% of the time. Thus, suing this method, all the leucine residues in a given amino acid sequence would be assigned the codon UUG.

In another method, a codon-optimized sequence contains the same frequency of each codon as is used in the organism where the codon-optimized sequence is intended to be expressed. Thus, using this method for optimization, if a hypothetical polypeptide sequence had 100 leucine residues, referring to Table 2 for frequency of usage in the *S. cerevisiae*, about 5, or 5% of the leucine codons would be CUC, about 11, or 11% of the leucine codons would be CUG, about 12, or 12% of the leucine codons would be CUU, about 13, or 13% of the leucine codons would be CUA, about 26, or 26% of the leucine codons would be UUA, and about 27, or 27% of the leucine codons would be UUG. Using this method, the frequency of codon usage, and not necessarily the order of the codons, is important. Thus, as will be understood by those of ordinary skill in the art, the distribution of codons in the sequence can vary significantly using this method. However, the sequence always encodes the same polypeptide.

In one embodiment of the invention, a sequence can be codon-optimized for expression in two yeast strains, for example, in both *Saccharomyces cerevisiae* and *Kluveromyces lactus*. Thus, according to this embodiment, codons are selected according to their usage in both strains.

Codon-optimized sequences of the present invention include those as set forth in Table 3 below:

TABLE 3

Termite cellulase genes constructed

| Donor organism | DNA sequence used | Accession number and amino acid sequence |
|---|---|---|
| Holomasti-gotoides mirabile | TTAATTAAAATGAGATTTCCATCTATTTTCACTGCTGTTTTGTTCGCAGCCTCAAGTGC<br>TTTAGCAGAGAAACATCCTAAGTTCGTATGGCAACAGTGTACAAAGGGTGGATGCTC<br>CGACGTGTCTGGTTATTTGGTGCACGACAGACATATAGGGGACGTTTGGGACAGAGA<br>GAATACCGATTACCCAGAATTAGATTACGACGCCAACGTAGGTGTCACTGTGTCAGC<br>AGACGGAAAGACTTTATCACAAAGATTAGTTTCCAAATTGTGGGACGATAAGAAAGC<br>AGTAGGATCTAGAGTGTACATAGTGGACACCACTGACAAGAAATATCAGTTATTTCA<br>ATTTGTTGGTAAGGAGTTTACATACACTGTGGACATGTCACAAATTCCTTGCGGTGTC<br>AACGCCGCTTTGTACACTGTCGAAATGCCAGCAGAGGGAAATCTCCTGGTGGTGTA<br>GAATACGGTTATGGTTACTGCGACGCAAACTGTGTGGACGGTGGATGTTGCATGGAG<br>TTCGATATCCAAGAAGCCTCCTCTAAGGCAATAGTGTACACAACTCACTCATGTCAAT<br>CTCAGACCGGAGGTTGCGACACAAGTGGTTGTGGTTACAACCCATATAGAGATTCAA<br>ATGACCACGCCTTTTGGGGTCAAACTATTAATGTCAACCAACCTGTGACTATAGTGAC<br>ACAGTTCGTTGGATCAGGTGGTTCTTTAACTGAAGTCAAGAGATTGTACGTCCAAGG<br>AGGTAAAGTGACCCCAGCAGCCAAAAGTTTATCCGATTCATATTGCAATGTTAACGA<br>CTATCGTTCTTTGAAAACAATAGGAGCTTCATTCCAAAGAGGACATGTAGTCGTGTTC<br>TCATTATGGGACAGTGATGGAATGTCCTGGATGGATGGTGGAAACGCCGGTCCTTGT<br>ACGAGTTACAACGTTGCAACCGTTGAATCATCTCAGCCAAATTTGAAAGTAACATGG<br>TCCAACGTCAAGTTTGGTGATATCGACAGTACTTACTAAGGCGCGCC<br>(SEQ ID NO: 1) | Accession No: AB071011<br>MLVALAVSVFCEKHPKFVWQQCTK<br>GGCSDVSGYLVHDRHIGDVWDREN<br>TDYPELDYDANVGVTVSADGKTLS<br>QRLVSKLWDDKKAVGSRVYIVDTT<br>DKKYQLFQFVGKEFTYTVDMSQIPC<br>GVNAALYTVEMPAEGKSPGGVEYG<br>YGYCDANCVDGGCCMEFDIQEASS<br>KAIVYTTHSCQSQTGGCDTSGCGYN<br>PYRDSNDHAFWGQTINVNQPVTIVT<br>QFVGSGGSLTEVKRLYVQGGKVTP<br>AAKSLSDSYCNVNDYRSLKTIGASF<br>QRGHVVVFSLWDSDGMSWMDGGN<br>AGPCTSYNVATVESSQPNLKVTWSN<br>VKFGDIDSTY<br>(SEQ ID NO: 21) |
| Coptotermes lacteus symbiont | TTAATTAAAATGAGATTTCCTTCCATATTCACCGCTGTTTTGTTCGCAGCCTCAAGTGC<br>TTTAGCAGAATGTACTAAGGGTGGATGTACTAACAAGAATGGATACATAGTTCATGA<br>TAAGCACGTCGGTGACATCCAGAATAGAGACACTTTGGACCCTCCAGACTTAGATTA<br>TGAAAAGGACGTGGGAGTAACCGTGTCCGGTGGAACCCTTAGTCAAAGATTAGTCTC<br>AACTTGGAACGGTAAGAAAGTCGTGGGAAGTAGATTGTATATTGTGGACGAAGCCGA<br>CGAGAAATATCAATTATTCACATTTGTCGGTAAGGAGTTCACCTATACCGTTGATATG<br>TCCCAGATCCAATGTGGAATCAATGCCGCATTATACACAGTGGAAATGCCTGCCGCT<br>GGAAAGACCCCTGGAGGTGTTAAGTATGGATATGGATATTGTGATGCCAACTGCTG<br>GATGGAGATTGTTGTATGGAGTTCGATATCCAAGAAGCTTCTAACAAGGCAATCGTT<br>TACACCACCCATTCCTGTCAAAGTCAAACTTCAGGTTGCGATACCTCAGGATGCGGTT<br>ACAACCCTTACAGAGACAGTGGTGACAAGGCATTCTGGGGAACAACTATAAACGTAA<br>ACCAGCCTGTGACAATTGTAACACAGTTTATCGGTTCTGGTAGTTCCTTAACTGAAGT | Accession No: AB089801<br>ECTKGGCTNKNGYIVHDKHVGDIQ<br>NRDTLDPPDLDYEKDVGVTVSGGTL<br>SQRLVSTWNGKKVVGSRLYIVDEA<br>DEKYQLFTFVGKEFTYTVDMSQIQC<br>GINAALYTVEMPAAGKTPGGVKYG<br>YGYCDANCVDGDCCMEFDIQEASN<br>KAIVYTTHSCQSQTSGCDTSGCGYN<br>PYRDSGDKAFWGTTINVNQPVTIVT<br>QFIGSGSSLTEVKRLCVQGGKTFPPA<br>KSLTDSYCNANDYRSLRTMGASMA<br>RGHVVVFSLWDSNGMSWMDGGNA |

TABLE 3-continued

Termite cellulase genes constructed

| Donor organism | DNA sequence used | Accession number and amino acid sequence |
|---|---|---|
| | CAAAAGATTGTGCGTGCAAGGTGGAAAGACCTTCCCTCCAGCCAAATCATTAACCGA CAGTTATTGTAATGCCAACGACTATAGAAGTTTGAGAACTATGGGTGCATCCATGGC TAGAGGACACGTTGTTGTGTTTTCTTTGTGGGATTCTAATGGTATGAGTTGGATGGAT GGAGGTAACGCCGGTCCTTGTACCTCATATAATATTGAATCTTTGGAATCCAGTCAGC CAAACTTAAAGGTCACATGGTCAAACGTGAAATACGGAGAGATCGATTCTCCTTATT AAGGCGCGCC (SEQ ID NO: 2) | GPCTSYNIESLESSQPNLKVTWSNVK YGEIDSPY (SEQ ID NO: 22) |
| Cryptocercus punctulatus symbiont | TTAATTAAAATGAGATTTCCATCTATTTTCACTGCTGTGTTGTTTGCCGCTTCAAGTGC TTTAGCATCTAGAATATCCGTGTCATGGTTGAGTACATCCGGTTCCAAAATAACCGAT GGAGGTCAAACTGTCAGATTAACAGGAGTGAATTGGTTTGGTTATGAAACCTCAGAG GAAGTGTTTCACGGTTTGTGGGCCGCTGGTTTGCACGACTTGGTACAGGGTGTCTCCC AAAAGAAATTCAACACTTTTAGAGTGCCTATTTCCGCATCTGTTTTGCAAGACTGGAA GGCCGGAAAGCCAAACCCAAAACCAAACATCAATTTGAACGTGAATGCTGACTTAGA GGGGTTTGAACAATCAACAAATATTGACTTATTCTTAGCCGACTGTAAGAAGTACAA AATCTACGTGTTCATCGACGTGCATGGTGTTACAGATGGATCATATATGGACAACTTA TGGTACACCTCTGCTCACCCTGCCGAATGGATAACAGTGCATTGGAGTGGTTCGCCG ATCACTACAAGGGAGATCAGACTATTATAGGTATTGACATAAAGAACGAGCCACACG GTAGATGCGAACAAGCCGAAGCAGCTAAGTGGTCCGATAGTAAAGACAATAATAAC TGGAAGTACTTCATTGAGACAGCCGCAGCTAGAATCTTAGGTAAGAATCCTAACTTG TTAATATTGGTTGAAGGAATTGAGTGTTACAACAACAACTGGGGTTGGTGGGGTGGA AACTTAATCCCAGTTAATGACTATCCTATAAACTTGGGTTCTGGACAAGAAGCAATTAG TCTATTCCCCACACGAATACGGTCCTTCTGTGAATGATCAGTCATGGTTCAAATCTGG TTTCAATTATGATTCCTTGTACGCCGATCATTGGCAAAAGATGTGGATGTTCATTATC GAAAAGAACATCGCCCCTATATTGATCGGAGAGTGGGGTGGTCACGTTGTAGAACCT AATACTACCTGGATGAAGGCTTTGGTCCAATTAATATCCAAATATGGATTGTCACAA ACTTTCTGGTGCTTAAACCCTGATAGTGGTGACACTGGAGGTTTGTTAGAAAACGATT GGATAACTTGGGATACAGCCAAATTGGATATAATTAAAGGTGTGTTATAAGGCGCGC C (SEQ ID NO: 3) | Accession No: AB274702 MLLFLLSRISVSWLSTSGSKITDGGQ TVRLTGVNWFGYETSEEVFHGLWA AGLHDLVQGVSQKKFNTFRVPISAS VLQDWKAGKPNPKPNINLNVNADL EGLNNQQIFDLFLADCKKYKIYVFID VHGVTDGSYMDNLWYTSAHPAEWI YSALEWFADHYKGDQTIIGIDIKNEP HGRCEQAEAAKWSDSKDNNNWKY FIETAAARILGKNPNLLILVEGIECYN NNWGWWGGNLIPVNDYPINLGSGQ KQLVYSPHEYGPSVNDQSWFKSGFN YDSLYADHWQKMWMFIIEKNIAPIL IGEWGGHVVEPNTTWMKALVQLIS KYGLSQTFWCLNPDSGDTGGLLEN DWITWDTAKLDIIKGVL (SEQ ID NO: 23) |
| Mastotermes darwiniensis symbiont | TTAATTAAAATGAGATTTCCATCTATTTTCACTGCTGTTTTGTTCGCAGCCTCAAGTGC TTTAGCAGCCTATTACATCTCCGCTTCTGGTAATGAGTTGGTGGACCCAACCGGAAAA CAATTAAGAATCACCGGTATAAACTGGTTTGGATTCGAGACTTCACAGTCTGCTTTTC ACGGTTTGTGGAACGCCAACTTACACAGGTCGTGCAACAGGTTGCGGAGCACGGTT TTAATTGCTTCAGATGTCCAATCTCCTGTGACTTGATCCACAAATGATGAGAGGAGA TAAGACACCATTACAGTGGATTAACACTGAGCCAGACGCAAATCCTGATATGAAAGG TATCTCTTCAAGAGGAATATGGGATATGTTTATGGCCGACTGCAAGAAAGCCGGTAT TAAGGTGTTTATCGATATTCATGGTATCCAACCAGATTCTTATACATTGCCTTTATGG GGAGATACAGAATACTTGATTTCCGCCTTAGAGTGGTTCGCAAACGAGTTCAAGAAT GACGATACTTTCATTGCCATCGACGTCAAGAACGAACCACATCAGCAAGGTCAGGGA TGCGGTACTGGTGCAAATGACGCCGTGTGGGAATCTTCAACACGTTCTAACAATTGG CCTTATGTTGCGGGATTGCGGGTAAAAGAATATTAGCTAAGAATCCAGGATTATTA ATCTTGGTCGAAGGAAATCAATGCTACAAAGGTGATAGTTCCTGGTGGGGAGGTAAC TTAGCTGGTGTCAAAGATATCCCTGTGGACGTTGGAAACCCAAAGAAGTTAGTGTAT TCCCCTCACGAATACGGTCCTTCTGTGAATGATCAAGCCTGGTTCCATCCAACTATTA ACTATGACCAGTTGTATTCCCAGCATTGGCACAAACATTGGTTGTATATCCACGAAGA GGGTATTGCTCCATTATTGATAGGAGAATGGGGTGGAAAGTTATCGGGACCAATAC ACAGTGGATGAAGTTATTCGTTAACTTAATCGCACAGTACGGTTTAAGTCACACTTTC TGGTGCTTGAACCCAAACTCCGGAGATACCGGTGGATTGTTAAAGGATAATTGGAAA GACTGGGATGAGGAGAAATATGCTTTCATTAAGCCTTGTTTGGGTGGTTCCTTGTTTA AGTAAGGCGCGCC (SEQ ID NO: 4) | Accession No: AB274656 MLVLLASFGVAYYISASGNELVDPT GKQLRITGINWFGFETSSAFHGLW NANLHKVVQQVAEHGFNCFRCPISC DLIHKWMRGDKTPLQWINTEPDAN PDMKGISSRGIWDMFMADCKKAGI KVFIDIHGIQPDSYTLPLWGDTEYLIS ALEWFANEFKNDDTFIAIDVKNEPH QQGQGCGTGANDAVWESSTRSNN WPYVAGLAGKRILAKNPGLLILVEG NQCYKGDSSWWGGNLAGVKDIPVD VGNPKKLVYSPHEYGPSVNDQAWF HPTINYDQLYSQHWHKHWLYIHEE GIAPLLIGEWGGKLSGTNTQWMKLF VNLIAYGLSHTFWCLNPDSGDTGG LLKDNWKDWDEEKYAFIKPCLGGS LFK (SEQ ID NO: 24) |
| Neotermes koshunensis symbiont | TTAATTAAAATGAGATTTCCATCTATTTTCACTGCTGTTTTGTTCGCAGCCTCAAGTGC TTTAGCAGGCCTTGTCTGACTTGGTGAAGATTACATGTCGATGGTAATAGAATCGTGATG GGAAAACCAGGTTTGGCTTCCTCTAAAACAGCTATGTTGAGAGGAGTGTCATGTAGT TGGCACAACTGGTGGCCTCAATTTCATTCCGCCGCTACAGTTAGAGGTTTGAAATCTG ACTTTCACGCAAATGTCGTGAGAACTTTCATAGGTGTTGAAAAGGAGGGAGGTTTCT TAACAAACCAGCAAAAGGCTTATGATTGCTGTTACGCCGTAGTCGATGAATGCATCG CACAAGGAATATGTTATTATAAACTGGGCTTCAGTTTTGACCTACCAAACTCA AGCTACCCAGTTCTTCAAGACCGTTGCAACCAAATATCATAGTTCTTCTTACGTCATA TACGAGTTATTGAACGAACCAGAAGCTGCGACATGGGCACAAATTAAACCTTATAGT CAAGCTTTAATTCAAACAATCAGAGCTATTGACCCATCTAATTTGATATTAGTCCCAA CCCCTAGATGGGATCAAGAGATTGGTGCAGCTGCAAACGACCCTATCACAGGAGATA ACAATTTGGCTTATACTTTACACATATACACCGGAACACACCCAGCTAGTTATAGAG ATGACGCCAGAGCAGCTAAGAAGAAAATCCCAGTGTGGGCCGACGAAAACGGTGCA ATGAACGCTGATGGAAAAGGAGCCTTGGATAGAACTGGTTGGAATACCTGGATCGCC TTTTACGAAGAGTTACAGATACCTTGGTTGGGATATGGTACAAGATACTTCCGAA ACCTGTTCAATTTTCAAATCTACAGATTCCTTTAATGACTTGTCCGATTGGGGGAAAGT TATTGAAGGAAACCATAAGAAAATACCAATAAGGCGCGCC (SEQ ID NO: 5) | Accession No: AB274614 MLGLLLSPSLSEADPDLVRLHVDGN RIVMGKPGLASSKTAMLRGVSCSW HNWWPQFHSAATVRGLKSDFHANV VRTFIGVEKEGGFLTNQQKAYDCCY AVVDECIAQGIYVIINWASFVLTYQT QATQFFKTVATKYHSSSYVIYELLN EPEAATWAQIKPYSQALIQTIRAIDPS NLILVPTPRWDQEIGAAANDPITGDN NLAYTLHIYTGTHPASYRDDARAAK KKIPVWADENGAMNADGKGALDR TGWNTWIAFYEELQIPWLGYGTQDT SETCSIFKSTDSFNDLSDWGKLLKET IRKYQ (SEQ ID NO: 25) |

TABLE 3-continued

Termite cellulase genes constructed

| Donor organism | DNA sequence used | Accession number and amino acid sequence |
|---|---|---|
| Hodotermopsis sjoestedti symbiont | TTAATTAAAATGAGATTCCCTTCCATTTTCACTGCTGTTTTGTTCGCAGCCTCAAGTGC<br>TTTAGCAGCCCCTCCATTTGGAAGATTATGCGTTGAAGGAAACAAAATCGTCGGTAA<br>CAAGAGAGCTCCTGGAGTGTTAAGAGGTGTTGGTTTGTCCTGGCATAATTGGTGGCCT<br>CAGTTTTACAACGCTGCAACCATCAATCACTTAAAGAACGACTTTCATGCCAATGTCA<br>TTAGAGCTGCTATAGGAGTGGAGAAAGAGAATGGTTACTTTGACAATCAGCAAAACG<br>CCTATGATTTGTTATACGCAGCTGTGGACGCAGCCTTGTCCGCTGGAATATATGTTAT<br>CGTGGATTGGCAGGCCTTCCAAATCCACGAATCAGATGCAAAACAATTCTTTACTAC<br>AGTTGTGAATAAGTACAAAGGTAAGAGTAACGTTATCTATGAGATATTTAATGAACC<br>TGAATCCGCTGGTTGGTCTGAAATCAAGAAGTATTCAATTTCCTTAATTCAGACAATC<br>AGAGCAATTGATTCCAACGCATTCATATTGGTTCCAACCCCTAATTGGGATCAGTATG<br>TTGAACAGGCTGCAGCCGACCCTATTAGTGAGTACAGTAATATCGCCTATACAATTC<br>ACATATATGCCGCAACACATCCTTTATCTTATTTGGATAACGCTAGAACTGCCTTGAA<br>AACTATCGCCTTATTTGGGACCGAGATAGGTGCAATGAGGCATCCGGTGATGGAGC<br>AATAGACCAATCCAAGTACCAACAGTGGATCGATTTCTATGAGCAGAATGGAATCTC<br>ATACTTATGCTGGGCTGTACAGTCTAAAGAAGAGACTGACAGTATATTGAAACCAAG<br>TGAAGATTGGAATGATTTGACAGCATGGGGAAAATTGTGTAAGTCAACAATTACTGC<br>ACACCAGTAAGGCGCGCC<br>(SEQ ID NO: 6) | Accession No: AB274582<br>MLVLLLHFINSKAPPFGRLCVEGN<br>KIVGNKRAPGVLRGVGLSWHNWW<br>PQFYNAATINHLKNDFHANVIRAAI<br>GVEKENGYFDNQQNAYDLLYAAVD<br>AALSAGIYVIVDWQAFQIHESDAKQ<br>FFTTVVNKYKGKSNVIYEIFNEPESA<br>GWSEIKKYSISLIQTIRAIDSNAFILVP<br>TPNWDQYVEQAAADPISEYSNIAYTI<br>HIYAATHPLSYLDNARTALKTIALFG<br>TEIGAMEASGDGAIDQSKYQQWIDF<br>YEQNGISYLCWAVQSKEETDSILKPS<br>EDWNDLTAWGKLCKSTITAHQ<br>(SEQ ID NO: 26) |
| Reticulitermes speratus symbiont | TTAATTAAAATGAGATTTCCATCTATTTTCACTGCTGTTTTGTTCGCAGCCTCAAGTGC<br>TTTAGCAGCCTTGGTACATATGGAATTAGAGAATAACTCCACTAGATTGAGAGTGAA<br>GGGAAATAAGATCGTGGTCGGAAACTCTGATAAAGGTTTGAGATTAAGAGGAGTGA<br>ATTTGTCCTGGAACAACTGGTGGCACCAATTCTACAACGCTGACACCGTTAGACACTT<br>AAAGAACGACTTTCACGTCAATGTGATAAGAGCAGCCATTGGTGTGGAACAGGATGG<br>TGGATGGGAATCAAACAAGCAAAGAAGTTACGATGACTTGTACGCTGTTATCGACGC<br>ATGTATCGCTAATAACGTCTATGTGATTGTCGATTGGCAGACTTTCTCTATCAAGTTG<br>TCAGAAGCCACAGAGTTCTTCACCAACGTTGCAAACAAATACCATAGTTCTTCCTATA<br>TCATCTACGACTTGTTGAACGAGCCTGATTCATCTGTGCCAAGTTGGTCCGCAATCAA<br>GTCCTATGCCGAATCTTTGATAAAGACCATTAGAGCTATAGATTCCTCCAACTTAATA<br>ATTGTGCCAACTCCAAATTGGGATCAGTACGTGAAGCAGGCTGCCGCAGATCCTATT<br>ACATCTGACAGTAACTTAATCTACTCAATACACATATACGTCGGTACTCACCCTATGA<br>GTTATATGGACGATGCTAGAGAAGCCTTAAAGACAATCCCTTTAATCGGAGGTGAAA<br>TAGGTGCAATGAATGCTGATGGTGACGGAGCTTTGGATGTTTCCAAATTCAACCAAT<br>GGATAGACTTCTTATAAGGCGCGCC<br>(SEQ ID NO: 7) | Accession No: AB274534<br>MRKAMFVGLFLIALVHMELENNST<br>RLRVKGNKIVVGNSDKGLRLRGVN<br>LSWNNWWHQFYNADTVRHLKNDF<br>HVNVIRAAIGVEQDGGWESNKQRS<br>YDDLYAVIDACIANNVYVIVDWQTF<br>SIKLSEATEFFTNVANKYHSSSYIIYD<br>LLNEPDSSVPSWSAIKSYAESLIKTIR<br>AIDSSNLIIVPTPNWDQYVKQAAAD<br>PITSDSNLIYSIHIYVGTHPMSYMDD<br>AREALKTIPLIGGEIGAMNADGDGA<br>LDVSKFNQWIDFL<br>(SEQ ID NO: 27) |
| Reticulitermes speratus symbiont | TTAATTAAAATGAGATTTCCATCTATTTTCACAGCAGTTTTGTTCGCAGCCTCAAGTG<br>CTTTGGCCGGTGATTCCGGAAGAACAACCAGATATTGGGACTGTTGCAAAGCCTCTT<br>GTGCTTGGGAAAAGAAAGCAGCCGTAACTCAACCTGTTGACACGTGCGGTAAGGACG<br>GAACCACTAGATTGGCTAGTAATGATACCGTGAAAAGTTCCTGTGACGGAGGTGATG<br>GATACATGTGTTATGATCAGGCACCATGGGCTGTTAACGATTCTGTAGCCTACGGTTT<br>CGCCGCAGCTGCATGTTGTGGTGGAGAAACCGGTGCTTGCTGTAATTGCTATGAGTTG<br>ACATTCACATCAGGTCCAGTGAATGGAAAAAAAATGGTGGTCCAGGTGACTAATACC<br>GGAGGTGATTTGGGAAGTAACCAGTTCGACTTAGCCATCCCAGGAGGTGGTGTCGGA<br>ATATACAATGGTTGTACACAACAATCAGGTGCCCCTGCTGACGGTTGGGGATCAAGA<br>TACGGAGGTGTCAGTTCTAGAAGTGAGTGTTCCCAGTTGCCATCAGGTTTACAAGCC<br>GGATGCCAGTGGAGATTCGACTGGTTCCAAAACGCAGACAATCCTTCAATTAATTTC<br>AACCAAGTCACTTGTCCAAGTGAATTGATTGCAAGAACCAACTGCAAGAGAACATAA<br>GGCGCGCC<br>(SEQ ID NO: 8) | Accession No: AB045179<br>MLLLFSLCLISWLVGDSGRTTRYWD<br>CCKASCAWEKKAAVTQPVDTCGKD<br>GTTRLASNDTVKSSCDGGDGYMCY<br>DQAPWAVNDSVAYGFAAAACCGG<br>ETGACCNCYELTFTSGPVNGKKMV<br>VQVTNTGGDLGSNQFDLAIPGGGVG<br>IYNGCTQQSGAPADGWGSRYGGVS<br>SRSECSQLPSGLQAGCQWRFDWFQ<br>NADNPSINFNQVTCPSELIARTNCKR<br>T<br>(SEQ ID NO: 28) |
| Pseudotrichonympha grassii | TTAATTAAAATGAGATTCCCTTCTATATTCACTGCTGTTTTGTTTGCAGCCAGTTCTGC<br>CTTAGCACAGGCTGAGAATCACCCATCCTTGTCTTGGCAAATTGTAGATCCGGTGG<br>ATCATGCACCCAAACCTCCGGTTCAGTTGTCTTGGATTCCAACATGAGATTTCCTTCT<br>ATCTTTACTGCTGTCTTATTCGCCGCTTCATCAGCTTTAGCATGGAGATGGACACACG<br>ATTCCAGTTTAACTAATTGTTATGATGGAAATGAGTGGAGTTCCTCATTATGCCCTGA<br>CCCTAAAACTTGTTCTGATAACTGTTTAATCGACGGTGCCGATTACTCTGGAACTTAT<br>GGAATTACTTCCTCTGGAAACTCCTTGAAGTTGGTGTTCGTCACTAACGGACCTTACT<br>CTACTAACATAGGTTCAAGAGTGTACTTGTTAAAAGACGAATCTCACTACCAAATATT<br>TGACTTAAAGAACAAAGAGTTTACATTCACTGTTGATGATTCTAATTTGGACTGCGGA<br>TTAAACGGAGCCTTGTACTTTGTAGATGAGGATGGAGGACGGTAGAACTTCAAGATTC<br>TCTTCCAATAAGGCAGGAGCCAAATACGGTACTGGATATTGTGACGCCCAATGCCCA<br>CACGATATTAAGTTCATTAACGGTGAAGCAAACGTTGAAAACTGGAAACCTCAAACC<br>AATGACGAAAATGCTGGTAACGGTAGATACGGAGCCTGCTGTACAGAGATGGATATA<br>TGGGAGGCAAATAAGTATGCTACTGCCTATACCCCTCACATCTGTACAGTCAACGGA<br>GAATATAGATGTGATGGTAGTGAATGTGGTGACACTGATTCCGGAAATAGATATGGA<br>GGAGTGTGCGATAAGGACGGATGCGATTTCAACTCTTATAGAATGGGTAACACTTCA<br>TTTTGGGGTCCAGGATTGATCATTGACACAGGTAAGCCAGTTACTGTTGTAACCCAGT<br>TCGTAACCAAAGATGGAACTGACAACGGTCAATTGTCAGAGATAAGAAGAAAGTAC<br>GTCCAGGGAGGTAAGGTTATTGAGAATACAGTAGTCAACATCGCGGGTATGTCCAGT<br>GGTAATAGTATTACAGACGACTTTTGCAACGAGCAGAAATCAGCATTCGGAGACACT<br>AACGATTTTGAAAAGAAGGGTGGATTATCCGGTTTGGGAAAAGCCTTCGATTATGGT<br>ATGGTGTTAGTTTTGTCTTTATGGGATGATCATCAAGTTAATATGTTATGGTTAGATTC<br>CATATACCCTACCGACCAGCCTGCATCCCAGCCAGGTGTAAAGAGAGGACCATGTGC | Accession No: AB071864<br>MFVFVLLWLTQSLGTGTNQAENHPS<br>LSWQNCRSGGSCTQTSGSVVLDSN<br>WRWTHDSSLTNCYDGNEWSSSLCP<br>DPKTCSDNCLIDGADYSGTYGITSSG<br>NSLKLVFVTNGPYSTNIGSRVYLLK<br>DESHYQIFDLKNKEFTFVDDSNLD<br>CGLNGALYFVSMDEDGGTSRFSSNK<br>AGAKYGTGYCDAQCPHDIKFINGEA<br>NVENWKPQTNDENAGNGRYGACC<br>TEMDIWEANKYATAYTPHICTVNGE<br>YRCDGSECGDTDSGNRYGGVCDKD<br>GCDFNSYRMGNTSFWGPGLIIDTGK<br>PVTVVTQFVTKDGTDNGQLSEIRRK<br>YVQGGKVIENTVVNIAGMSSGNSIT<br>DDFCNEQKSAFGDTNDFEKKGGLSG<br>LGKAFDYGMVLVLSLWDDHQVNM<br>LWLDSIYPTDQPASQPGVKRGPCAT<br>SSGAPSDVESQHPDSSVTFSDIRFGPI<br>DSTY<br>(SEQ ID NO: 29) |

TABLE 3-continued

Termite cellulase genes constructed

| Donor organism | DNA sequence used | Accession number and amino acid sequence |
|---|---|---|
| | TACTTCATCTGGTGCCCCAAGTGATGTCGAATCACAACACCCTGACAGTTCCGTGACC<br>TTTAGTGATATCAGATTTGGTCCAATAGATTCAACATATTAAGGCGCGCC<br>(SEQ ID NO: 9) | |
| *Reticulitermes flavipes* gut symbiont | TTAATTAAAATGAGATTCCCTTCCATTTTCACTGCCGTCTTATTTGCAGCCTCATCAGC<br>ATTAGCCGAGAAACATCCTGCCTTTCAATGGAAGAAAGATGGTGTCACTCAAAATGG<br>ATTCTTGGTTCATGACAGACATGTGGGTGATAACTGGTATAGAGATCAGAAAGATGG<br>AAAATCCGGTGCTTTAGACTTAGACTACGAGAATGATGTTGGTGTTACTGTGTCCGGT<br>GGTACTTTAACCCAGAGATTGGTGTCAAACTATAGTTGGAATAACAAGACCGTTGTA<br>GGGTCCAGATTATACATCATGACCGCCGACGAAAAGAAGTATGAGAAATTTAACTTA<br>ACTGGTAAGGAGTTTACCTTCACCGTCAATTTGGCCCAAATACCATGTGGTGTGAACG<br>CTGCATTATACACAGTGGAAATGCCTGCTGACGGAATTGACGCCACTGACCAAACCC<br>AGGGTGCACCATACGGTTACGGATATTGCGATGCAAACTGTGTTGATGGAGGTTGTT<br>GTCCTGAGTTTGATGGTATTGAAGCCACGAGTAAAGCATTAGTATTCACTACCCACAC<br>GTGCTCAGGTACTGGAAGTGGTAGAGGAGGTTACACCGGTTGTGATACATCCGGATG<br>TGGTTACAACCCTTATCGTGACGACAACAACCATTCTTTCTGGACGAATGTCAGTGAAC<br>TTAGCTCAACCTGTGACTATAGTGACACAGTTCCAAACTAATGGTGATGTTACCAGA<br>AAATATATTCAAAATGGAAACCCAATCGACGGTGGAACCTAAACCAGAGTAGATGT<br>TCCGGAAAGCAAAACATGACTTCTACCTTCTCAGAGGTCATGTCGTGGTTTTCAGTT<br>TGTGGGATTCCGACGGAATGTCATGGTTAGATGGTGGTAATGCTGGACCTTGTACTTC<br>TTACAATATTAAAGATGTGGAAACAAGAACCCCAAACTTGACTGTAACCTGGTCCGA<br>TGTGAAATTCGGAAACATTGGATCAACAACTAATTAAGGCGCGCC<br>(SEQ ID NO: 10) | Accession No: DQ014511<br>MLTVLFLLSLGWCEKHPAFQWKKD<br>GVTQNGFLVHDRHVGDNWYRDQK<br>DGKSGALDLDYENDVGVTVSGGTL<br>TQRLVSNYSWNNKTVVGSRLYIMT<br>ADEKKYEKFNLTGKEFTFTVNLAQI<br>PCGVNAALYTVEMPADGIDATDQT<br>QGAPYGYGYCDANCVDGGCCPEFD<br>GIEATSKALVFTHTCSGTGSGRGG<br>YTGCDTSGCGYNPYRDDNNHSFWT<br>SSVNLAQPVTIVTQFQTNGDVTRKYI<br>QNGNPIDGGTLNQSRCSGKQNMTST<br>FSRGHVVVFSLWDSDGMSWLDGGN<br>AGPCTSYNIKDVETRTPNLTVTWSD<br>VKFGNIGSTTN<br>(SEQ ID NO: 30) |
| *Reticulitermes flavipes* gut symbiont | TTAATTAAAATGAGATTTCCATCTATTTTCACTGCTGTTTTGTTCGCAGCCTCAAGTGC<br>TTTAGCACAATGGATGCAGATCGGTGGTAAGCAGAAATATCCTGCCTTTAAGCCAGG<br>TGCTAAGTACGGAAGAGGTTATTGTGACGGACAGTGCCCTCACGACATGAAGGTGTC<br>TAGTGGAAGAGCAAACGTTGACGGATGGAAGCCACAAGACAACGAGAAAATAGTG<br>GAAATGGAAAATTGGGTACATGTTGCTGGGAGATGGATATATGGGAAGGAAACTTA<br>GTGTCCCAAGCCTACACCGTTCACGCTGGTTCCAAGTCCGGACAATATGAGTGTACTG<br>GAACACAATGCGGTGACACCGACAGTGGTGAAAGATTCAAGGGAACATGCGATAAA<br>GATGGTTGTGATTTCGCAAGTTACAGATGGGGAGCTACAGACTATTACGGTCCTGGA<br>AAGACCGTGGACACCAAACAGCCAATGACAGTCGTGACCCAGTTCATTGGTGACCCT<br>TTGACTGAGATAAAGAGAGTTTATGTACAAGGAGGAAAAGTCATAAACAATTCCAAA<br>ACATCTAACTTAGGTTCAGTGTACGATTCTTTGACTGAGGCCTTCTGCGATGACACCA<br>AACAGGTTACAGGTGATACAAATGACTTTAAGGCTAAAGGAGGTATGTCTGGATTCT<br>CCAAGAACTTAGACACCCCACAAGTTTTGGTGATGTCTTTATGGGATGACCATACAG<br>CTAATATGTTATGGTTAGATTCTACTTATCCTACCGATAGTACAAAGCCAGGTGCCGC<br>AAGAGGTACTTGTGCCGTCACCTCCGGGGACCCTAAAGATGTGGAATCCAAGCAAGC<br>CAACTCTCAGGTAGTTTACAGTGACATTAAGTTTGGTCCTATTAATTCAACATACAAA<br>GCAAATTAAGGCGCGCC<br>(SEQ ID NO: 11) | Accession No: DQ014512<br>MVLCILLQWMQIGGKQKYPAFKPG<br>AKYGRGYCDGQCPHDMKVSSGRA<br>NVDGWKPQDNDENSGNGKLGTCC<br>WEMDIWEGNLVSQAYTVHAGSKSG<br>QYECTGTQCGDTDSGERFKGTCDK<br>DGCDFASYRWGATDYYGPGKTVDT<br>KQPMTVVTQFIGDPLTEIKRVYVQG<br>GKVINNSKTSNLGSVYDSLTEAFCD<br>DTKQVTGDTNDFKAKGGMSGFSKN<br>LDTPQVLVMSLWDDHTANMLWLD<br>STYPTDSTKPGAARGTCAVTSGDPK<br>DVESKQANSQVVYSDIKFGPINSTY<br>KAN<br>(SEQ ID NO: 31) |
| *Reticulitermes flavipes* gut symbiont | TTAATTAAAATGAGATTTCCATCTATTTTCACTGCTGTTTTGTTCGCAGCCTCCAGTGC<br>ATTAGCAGAGTTTACATTCACAACCGATGTATCCGGTTTACCTTGTGGGTTAAACGGT<br>GCCTTGTACTTTGTCGCCATGGACGAGGACGGAGGTAAAGCAAAGCATCCATTATCC<br>AAACCAGGTGCTAAGTACGGAATGGGTTACTGTGACGCCCAATGTCCACACGATATG<br>AAGTTTATCGAAGGATTGGCAAACTGCGAGGGTTGGAAGCCTCAGGATAATGACGAA<br>AACTCAGGTAATGGAAAATACGGTACTTGTTGCGCTGAAATGGACATATATGGGAGGCC<br>AACAGTCAAGCAACAGCTTATACTGTGCATGCCTGTTCCAAGACCGGAGCAACCAAA<br>TGGTCCGGAAATGACTGTGGTGATGATGACAACAGATACAATGGAATTTGCGATAAG<br>GACGGTTGCGATTACAACTCATGGAGATTAGGTAATCAGACTTTCTTCGGACCTGGTT<br>TAATTGTAGATAGTTCCAAACCTGTAACAGTCGTGACCCAATTCATAACTTCCAATAA<br>CCAAGATTCAGGAGAATTAGTCGAGGTTAGAAGATTGTACGTCCAGAACAACAAAGT<br>CATCCAGAACACTGTTACTAACATCCAGGGTATAAAGAATGCTGATTCTATTACCGAT<br>TCCTTTTGCGATGATACAAAGTCCGTTTTCGGTGACACTAATGACTATAAGGCCAAGG<br>GAGCAATGGCTGGATTTTTCAAAGAGTATCGATCCAGGTGTAGTCTTAGTGAGAAGTT<br>TGTGGGACGATCACTCCGTTAATATGTTGGATTCAACCTACCCTACCGATAGACAG<br>TAACAAACCAGGAGCCAGTAGAGGTCCTTGCGCAATTACTTCAGGAAAACCATCTGA<br>TGTAGAATCCCAGTCCGCTTCTGCATCTGTCAAGTTCTCCGATATTAGATTCGGTCCA<br>ATAGATTCTACTTATAGTAAATAAGGCGCGCC<br>(SEQ ID NO: 12) | Accession No: DQ014513<br>MFKLKNKEFTFTTDVSGLPCGLNGA<br>LYFVAMDEDGGKAKHPLSKPGAKY<br>GMGYCDAQCPHDMKFIEGLANCEG<br>WKPQDNDENSGNGKYGTCCAEMDI<br>WEANSQATAYTVHACSKTGATKWS<br>GNDCGDDDNRYNGICDKDGCDYNS<br>WRLGNQTFFGPGLIVDSSKPVTVVT<br>QFITSNNQDSGELVEVRRLYVQNNK<br>VIQNTVTNIQGIKNADSITDSFCDDT<br>KSVFGDTNDYKAKGAMAGFSKSIDP<br>GVVLVRSLWDDHSVNMLWLDSTYP<br>TDSNKPGASRGPCAITSGKPSDVESQ<br>SASASVKFSDIRFGPIDSTYSK<br>(SEQ ID NO: 32) |
| *Mastotermes darwinensis* | TTAATTAAAATGAGATTCCCAAGTATATTTACTGCTGTTTTGTTCGCAGCCAGTTCTG<br>CTTTAGCAGCCTATGATTACAATGACGTATTAACCAAAAGTTTGTTGTTCTACGAAGC<br>TCAAAGATCCGGTAAGTTACCTTCTGATCAGAAAGTTACCTGGAGAAAAGATTCAGC<br>ATTAAACGATAAGGGACAAAATGGTGAGGACTTAACTGGTTGGATATATGACGCCGG<br>TGATTACGTGAAGTTTGGTTTTCCAATGGCATATACTGCTACCGTTTTGGCTTGGGGT<br>TTAGTGGACCATCCTGCCGGATACAGTTCTGCGGGTGTCTTGGATGATGGTAGAAAA<br>GCTGTGAAGTGGGTTACCGATTACTTAATCAAAGCCACAGATGATCAAAGAACGAATTA<br>TACGGACAGGTCGGTGACGGTGACGCAGATCACGCTTATTGGGGACGTCCAGAGGAT<br>ATGACAATGGCAAGACCAGCATACAAAATAGACACTTCAAGACCAGGTTCCGACTTA<br>GCGGGTGAAACCGCAGCGGCATTGGCTGCTGCATCTATTGTGTTTAAGTCAACAGAT<br>TCTAATTACGCCAACACCTTATTGACCCACGCAAAACAATTATTCGACTTTGCCAATA<br>ACTATAGAGGTAAGTATAGTGATTCCATAACACAGGCATCTAATTTCTACAGTAGTTC | Accession No: AJ511343<br>MRVLLCLLSAFALCQGAYDYNDVL<br>TKSLLFYEAQRSGKLPSDQKVTWRK<br>DSALNDKGQNGEDLTGGYYDAGDY<br>VKFGFPMAYTATVLAWGLVDHPAG<br>YSSAGVLDDGRKAVKWVTDYLIKA<br>HVSKNELYGQVGDGDADHAYWGR<br>PEDMTMARPAYKIDTSRPGSDLAGE<br>TAAALAASIVFKSTDSNYANTLLT<br>HAKQLFDFANNYRGKYSDSITQASN<br>FYSSSDYKDELVWAAVWLYRATND<br>QTYLTTAEKLYSDLGLQSWNGGFT |

TABLE 3-continued

Termite cellulase genes constructed

| Donor organism | DNA sequence used | Accession number and amino acid sequence |
|---|---|---|
| | CGACTATAAAGATGAATTGGTTTGGGCAGCTGTATGGTTGTACAGAGCCACTAACGA<br>TCAGACCTATTTGACAACTGCAGAGAAGTTATACTCAGACTTGGGATTACAGTCCTG<br>GAACGGAGGTTTCACATGGGACACAAAAAATTAGTGGAGTAAGCGTTATTGGCTAA<br>GATTACTGGTAAACAGGCATATAAGGACAAAGTAAAGGGATATTGTGATTATATCTC<br>AGGATCTCAGCAGAAAACACCTAAAGGATTAGTTTACATAGATAAGTGGGGTTCCTT<br>AAGAATGGCCGCAAACGCCGCATATATTTGCGCTGTAGCCGCAGACGTCGGAATCAG<br>TTCAACAGCTTACAGACAGTTCGCCAAAACACAGATTAATTACATATTGGGTGATGC<br>CGGACGTTCTTTTGTGGTTGGTTACGGAAACAACCCACCTACACACCCACATCACAG<br>ATCCAGTTCATGTCCTGACGCCCAGCAACATGCGATTGGAATAACTACAACAGTGC<br>TAACCCTAATCCACATGTTTTATACGGTGCATTAGTTGGTGGACCAGATTCCAACGAT<br>AATTATCAAGACTTAAGATCAGATTATGTCGCCAACGAAGTGGCAACAGACTACAAT<br>GCAGCCTTCCAGTCATTGTTAGCATTAATCGTGGACTTAGGTTTGTAAGGCGCGCC<br>(SEQ ID NO: 13) | WDTKISGVEVLLAKITGKQAYKDK<br>VKGYCDYISGSQQKTPKGLVYIDKW<br>GSLRMAANAAYICAVAADVGISSTA<br>YRQFAKTQlNYILGDAGRSFVVGYG<br>NNPPTHPHHRSSSCPDAPATCDWNN<br>YNSANPNPHVLYGALVGGPDSNDN<br>YQDLRSDYVANEVATDYNAAFQSL<br>LALIVDLGL<br>(SEQ ID NO: 33) |
| Reticulitermes flavipes | TTAATTAAAATGAGATTTCCAAGTATATTTACTGCCGTCTTATTTGCAGCCTCAAGTG<br>CTTTAGCCGCTTATGACTACAAAACAGTATTGTCCAATTCCTTGTTGTTCTACGAAGC<br>TCAAAGATCCGGTAAGTTACCTTCTGATCAGAAAGTCACTTGGAGAAAGGATTCAGC<br>ATTAAACGACAAAGGACAAAAGGGTGAGGACTTGACTGGAATGAGATTCCCATCAA<br>TATTCACCGCCGTGTTGTTGCTGCATCTTCAGCTTTAGCCGGTTATTACGATGCCGGT<br>GATTTCGTCAAATTCGGATTTCCAATGGCTTACACAGTTACCTTGGCATTAGCGGGTG<br>TTATTGATTACGAAAGTGCATACTCTGCTGCCGGAGCATTGGATTCAGGTAGAAAGG<br>CATTAAAGTACGGGACCGACTATTTCTTAAAGGCCCATACAGCTGCCAATGAGTTCT<br>ATGGACAGGTAGGTCAAGGAGATGTGGACCATGCATATTGGGGACGTCCAGAGGAT<br>ATGACATGTCTCGTCCTGCTTACAAAATAGACACCTCCAAGCCAGGTTCCGACTTAG<br>CTGCAGAGACTGCAGCTGCCTTAGCCGCAACGCCATCGCATACAAATCAGCTGATG<br>CAACATATTCCAATAACTTGATAACTCATGCAAAGCAGTTATTCGACTTTGCTAACAA<br>CTATAGAGGAAAATATAGTGATTCCATTACCGATGCCAAGAACTTTTATGCCTCAGG<br>AGATTATAAAGACGAATTAGTCTGGGCCGCTGCAGGTTTATACAGAGCTACAAATGA<br>CAACACATATTTGACCAAGGCTGAATCCTTATACAATGAGTTCGGATTGGGAAACTG<br>GAATGGTGCCTTCAATTGGGATAACAAAATCAGTTGGAGTACAGGTCTTATTGGCCAA<br>GTTAACATCAAAACAGGCATACAAGGATAAGGTTCAGGGTTACGTGGATTACTTGAT<br>CTCCTCCCAAAAAAAGACCCCTAAGGGATTAGTTTACATTGATCAATGGGGAACCTT<br>GAGACACGCTGCTAATAGTGCCTTAATCGCGTTGCAGGCTGCCGATTTAGGTATTAA<br>CGCAGCTACCTATAGAGCCTACGCAAAGAAGCAAATCGACTATGCTTTGGGTGATGG<br>TGGACGTTCTTATGTGGTGGGTTTTGGTACTAACCCACCTGTAAGACCACATCACAGA<br>AGTTCCAGTTGTCCTGACGCCCCAGCAGTCTGCGATTGGAACACCTACAATTCAGCTG<br>GTCCAAACGCCCACGTGTTAACTGGTGCCTTAGTTGGTGGACCTGATTCTAATGATTC<br>CTATACTGACGTCTAGATCAGACTACATTTCTAACGAGGTTGCAACTGATTACAACGCC<br>GGATTTCAGAGTGCTGTCGCTGGATTATTAAAGGCTGGAGTGTAAGGCGCGCC<br>(SEQ ID NO: 14) | Accession No: AY572862<br>MKVFVCLLSLALALCQAAYDYKTVL<br>SNSLLFYEAQRSGKLPSDQKVTWRK<br>DSALNDKGQKGEDLTGGYYDAGDF<br>VKFGFPMAYTVTVLAWGVIDYESA<br>YSAAGALDSGRKALKYGTDYFLKA<br>HTAANEFYGQVGQGDVDHAYWGR<br>PEDMTMSRPAYKIDTSKPGSDLAAE<br>TAAALAATAIAYKSADATYSNNLIT<br>HAKQLFDFANNYRGKYSDSITDAKN<br>FYASGDYKDELVWAAAWLYRATN<br>DNTYLTKAESLYNEFGLGNWNGAF<br>NWDNKISGVQVLLAKLTSKQAYKD<br>KVQGYVDYLISSQKKTPKGLVYIDQ<br>WGTLRHAANSALIALQAADLGINAA<br>TYRAYAKKQIDYALGDGGRSYVVG<br>FGTNPPVRPHHRSSSCPDAPAVCDW<br>NTYNSAGPNAHVLTGALVGGPDSN<br>DSYTDARSDYISNEVATDYNAGFQS<br>AVAGLLKAGV<br>(SEQ ID NO: 34) |
| Reticulitermes speratus | TTAATTAAAATGAGATTCCCAAGTATATTTACTGCCGTCTTATTTGCAGCCTCCAGTG<br>CATTAGCCGCTTATGACTACAAAACAGTATTGTCCAATTCCTTGTTGTTCTACGAAGC<br>TCAAAGATCCGGTAAGTTACCTTCTGACCAGAAAGTGACCTGGAGAAAGGATTCAGC<br>ATTAAACGACAAAGGACAAAAGGGTGAGGACTTAACCGGTGGATATTACGACGCCG<br>GAGACTTTGTGAAATTTGGTTTTCCAATGGCTTACACAGTTACCGTATTGGCATGGGG<br>TGTTATTGATTACGAATCCGCCTACTCTGCCGCAGGAGCTTTAGATTCAGGTAGAAAG<br>GCCTTGAAATATGGGACCGACTATTTCTTAAAGGCACATACAGCAGCTAACGAGTTT<br>TACGGACAGGTTGGTCAAGGTGACGTTGACCACGCATACTGGGGACGTCCTGAAGAT<br>ATGACCATGAGCAGACCAGCATACAAAATAGACACTTCTAAGCCTGGTTCCGACTTA<br>GCTGCAGAGACTGCAGCTGCATTAGCAGCCACAGCTATTGCATACAAATCTGCCGAT<br>GCAACATATTCCAACAATTTGATAACACATGCAAAACAATTATTCGACTTTGCCAAC<br>AATTACAGAGGAAAATATTCCGATAGTATTACCGATGCCAAGAACTTTTATGCTTCTG<br>GTGATTACAAAGACGAATTGGTATGGGCCGCTGCAGGTTGTACAGAGCAACCAATG<br>ACAACACATATTTGACTAAGGCAGAATCCTTATACAATGAATTGGTTTGGGAAACTT<br>CAATGGTGCCTTCAATTGGGATAACAAAGTCTCCGGAGTCCAGGTGTTATTGGCCAA<br>GTTAACCTCAAAACAAGTGTATAAGGATAAGGTACAGTCTTACGTGGACTATTTGAT<br>CTCCTCACAAAAAAAGACACCAAAAGGTTTAGTGTACATCGATCAATGGGGTACTTT<br>AAGACACGCAGCTAATTCTGCTTTGATCGCTTTGCAGGCAGCTGACTTAGGAATTAAC<br>GCTGCTACTTACAGAGCCTACGCAAAGAAGCAAATCGACTATGCTTTGGGTGATGGT<br>GGAAGATCCTATGTTATTGGATTTGGGACCAACCCTCCAGTAAGACCACATCACAGA<br>AGTTCATCTTGCCCAGATGCACCAGCTGTCTGCGATTGGAACACCTATAACTCCGGCT<br>GTCCAAACGCCCACGTGTTAACCGGTGCATTGGTTGGAGGACCTGATAGTAATGATA<br>GTTATACCGATGCTCGTTCTGACTACATATCCAACGAAGTGGCAACTGATTACAATGC<br>GGGTTTCCAATCCGCTGTCGCTGGATTATTGAAGGCGGGTGTCTAAGGCGCGCC<br>(SEQ ID NO: 15) | Accession No: AB019095<br>MKVFVCLLSLALCQAAYDYKTVL<br>SNSLLFYEAQRSGKLPSDQKVTWRK<br>DSALNDKGQKGEDLTGGYYDAGDF<br>VKFGFPMAYTVTVLAWGVIDYESA<br>YSAAGALDSGRKALKYGTDYFLKA<br>HTAANEFYGQVGQGDVDHAYWGR<br>PEDMTMSRPAYKIDTSKPGSDLAAE<br>TAAALAATAIAYKSADATYSNNLIT<br>HAKQLFDFANNYRGKYSDSITDAKN<br>FYASGDYKDELVWAAAWLYRATN<br>DNTYLTKAESLYNEFGLGNFNGAFN<br>WDNKVSGVQVLLAKLTSKQVYKD<br>KVQSYVDYLISSQKKTPKGLVYIDQ<br>WGTLRHAANSALIALQAADLGINAA<br>TYRAYAKKQIDYALGDGGRSYVIGF<br>GTNPPVRPHHRSSSCPDAPAVCDWN<br>TYNSAGPNAHVLTGALVGGPDSND<br>SYTDARSDYISNEVATDYNAGFQSA<br>VAGLLKAGV<br>(SEQ ID NO: 35) |
| Coptotermes formosanus | TTAATTAAAATGAGATTCCCTTCCATTTTCACTGCTGTTTTGTTCGCAGCCTCAAGTGC<br>TTTAGCAGCCTATGACTACAAGACAGTATTGAAGAACTCCTTGTTGTTCTACGAAGCT<br>CAAAGAAGTGGAAAATTGCCTGCAGACCAGAAGGTGACCTGGAGAAAGGATTCCGC<br>ATTAAACGACAAGGGACAAGGGAGAGGACTTAACTGGAGGTTATTACGACGCCG<br>GAGACTTTGTGAAGTTCGGTTTTCCAATGGCATACACAGTTACCGTGTTGGCCTGGG<br>TTTAGTCGATTATGAATCTGCTTACAGTACTGCGGGTGCCTTGGATGATGGTAGAAAG<br>GCCTTGAAATGGGGTACAGATTATTTCTTGAAAGCACATACCGCTGCCAATGAGTTTT<br>ACGGACAGGTGGGTCAGGGAGATGTGGATCATGCTTACTGGGGACGTCCTGAGGACA | Accession No: AB058671<br>MRVFVCLLSLALCQAAYDYKTVL<br>KNSLLFYEAQRSGKLPADQKVTWR<br>KDSALNDKGQKGEDLTGGYYDAGD<br>FVKFGFPMAYTVTVLAWGLVDYES<br>AYSTAGALDDGRKALKWGTDYFLK<br>AHTAANEFYGQVGQGDVDHAYWG<br>RPEDMTMSRPAYKIDTSKPGSDLAA |

TABLE 3-continued

Termite cellulase genes constructed

| Donor organism | DNA sequence used | Accession number and amino acid sequence |
|---|---|---|
| | TGACTATGTCTAGACCAGCTTACAAGATCGATACATCAAAACCTGGTAGTGACTTAG<br>CTGCAGAAACAGCAGCCGCTTTAGCAGCAACCGCAATAGCTTACAAGTCAGCCGATT<br>CTACCTACAGTAACAACTTAATTACTCATGCAAAGCAGTTGTTCTGATTTTGCAAACAA<br>TTATAGAGGAAAGTACTCTGATAGTATTACCGATGCCAAGAATTTCTATGCATCCGGT<br>GATTATAAGGACGAATTAGTATGGGCTGCAGCCTGGTTGTATAGAGCTACAAATGAT<br>AACACTTACTTAACCAAAGCCGAATCATTGTATAATGAATTTGGTTTAGGATCTTGGA<br>ACGGTGCATTCAATTGGGATAACAAGATATCCGGAGTTCAGGTCTTATTAGCCAAAT<br>TGACATCCAAACAAGCATACAAAGATAAAGTTCAGGGTTATGTTGATTACTTAGTCT<br>CCTCTCAAAAGAAAACTCCAAAGGGATTGGTCTATATTGACCAATGGGGAACCTTAA<br>GACACGCAGCTAATAGTGCCTTGATCGCTTTACAGGCCGCTGATTTGGGTATAAACG<br>CTGCTAGTTATAGACAATACGCAAAGAAGCAAATTGATTATGCCTTAGGTGACGGAG<br>GTCGTTCTTACGTGGTCGGATTCGGAACTAACCCTCCAGTAAGACCTCATCATAGATC<br>CAGTTCCTGTCCTGACGCACCAGCCGCTTGCGACTGGAATACTTACAACTCTGCCGGA<br>CCAAATGCCCACGTCTTGACCGGAGCCTTAGTAGGTGGACCAGATTCCAACGATAGT<br>TACACAGATTCACGTTCTGATTATATCAGTAACGAAGTCGCTACTGATTACAATGCCG<br>GTTTCCAATCTGCAGTTGCTGGTTTGTTGAAAGCCGGAGTATAAGGCGCGCC<br>(SEQ ID NO: 16) | ETAAALAATAIAYKSADSTYSNNLIT<br>HAKQLFDFANNYRGKYSDSITDAKN<br>FYASGDYKDELVWAAAWLYRATN<br>DNTYLTKAESLYNEFGLGSWNGAF<br>NWDNKISGVQVLLAKLTSKQAYKD<br>KVQGYVDYLVSSQKKTPKGLVYID<br>QWGTLRHAANSALIALQAADLGINA<br>ASYRQYAKKQIDYALGDGGRSYVV<br>GFGTNPPVRPHHRSSSCPDAPAACD<br>WNTYNSAGPNAHVLTGALVGGPDS<br>NDSYTDSRSDYISNEVATDYNAGFQ<br>SAVAGLLKAGV<br>(SEQ ID NO: 36) |
| Coptotermes acinaciformis | TTAATTAAAATGAGATTCCCTAGTATTTTCACTGCCGTCTTATTTGCAGCCAGTTCTGC<br>TTTAGCCGCATATGATTATACCACAGTTTTGAAAAGTTCCTTATTGTTCTACGAAGCTC<br>CAAAGATCCGGTAAGTTGCCAGCCGACCAGAAGGTCACTTGGAAAAAGATTCAGC<br>ATTAGACGATAAGGAAATAATGGAGAGGACTTAACAGGAGGTTATTATGACGCTG<br>GTGATTTTGTGAAGTTTGGTTTTCCTTTAGCATACACCGCTACTGTTTTAGCCTGGGGT<br>TTGGTGGACTATGAAGCGGGTTACTCATCCGCTGGAGCCACAGATGACGGTAGAAAG<br>GCAGTGAAATGGGCAACCGACTATTGTTGAAGGCACATACTGCCGCTACCGAGTTA<br>TACGGACAGGTCGGGACGGTGACGCCGATCACGCATATTGGGGACGTCCTGAAGAT<br>ATGACTATGGCTAGACCAGCATACAAGATCGACGTAGACAGACCAGGATCTGACTTA<br>GCGGGTGAAACGCTGCCGCTTTAGCCGCTGCATCATAGTTTCAAAGGTGTAGATT<br>CTTCATATTCTGACAACTTGTTAGCTCACGCTAAACAGTTATTTGATTTCGCTGACAA<br>TTATAGAGGAAAATACAGTGATTCCATAACACAAGCTTCAAACTTTTACGCCTCCGG<br>AGATTACAAAGACGAGTTAGTCTGGGCTGCCACTTGGTTGTACAGAGCAACCAACGA<br>TAATACATATTTGACCAAAGCAGAATCCTTGTACAACGAGTTCGGATTAGGAAACTG<br>GAACGGAGCCTTTAATTGGGACAACAAGGTGTCCAGGTGTTCAGGTGTTGTTAGCCAA<br>ATTGACCTCCAAGCAGGCTTATAAAGACACCGTTCAAGGATCGTCGATTATTTGATT<br>AACAATCAGCAAAAGACCCCAAAGGGTTTGTTATACATAGACCAATGGGGGACCTTG<br>AGACACGCAGCTAATGCTGCCTTAATAATCTTACAGGCTGCTGATTTGGGTATTTCTG<br>CCGACAGTTATAGACAATTCGCCAAAGAAGCAAATAGATTACGCTTTAGGTGACGGA<br>GTAGATCATATGTAGTTGGTTTTGGAGACAATCCTCCAACACATCCTCATCACCGTTC<br>TTCCTCATGCCCTGACGCCCAGCAGTATGCGATTGGAATACTTTCAATTCACCTGAT<br>CCAAACTTTCATGTCTTAACCGGAGCTTTAGTGGGAGGTCCTGATCAGAACGATAACT<br>ACGTTGATGATCGTTCTGACTACGTGTCCAACGAGTTGCAACCGACTATAATGCAG<br>GATTCCAAAGTGCTGTGGCCGCTTTAGTTACTTTAGGAGTTTAAGGCGCGCC<br>(SEQ ID NO: 17) | Accession No: AF336120<br>MRVFVCLLSALALCQAAYDYTTVL<br>KSSLLFYEAQRSGKLPADQKVTWR<br>KDSALDDKGNNGEDLTGGYYDAGD<br>FVKFGFPLAYTATVLAWGLVDYEA<br>GYSSAGATDDGRKAVKWATDYLLK<br>AHTAATELYGQVGDGDADHAYWG<br>RPEDMTMARPAYKIDASRPGSDLAG<br>ETAAALAAASIVFKGVDSSYSDNLL<br>AHAKQLFDFADNYRGKYSDSITQAS<br>NFYASGDYKDELVWAATWLYRAT<br>NDNTYLTKAESLYNEFGLGNWNGA<br>FNWDNKVSGVQVLLAKLTSKQAYK<br>DTVQGYVDYLINNQQKTPKGLLYID<br>QWGTLRHAANAALIILQAADLGISA<br>DSYRQFAKKQIDYALGDGGRSYVV<br>GFGDNPPTHPHHRSSSCPDAPAVCD<br>WNTFNSPDPNFHVLTGALVGGPDQ<br>NDNYVDDRSDYVSNEVATDYNAGF<br>QSAVAALVTLGV<br>(SEQ ID NO: 37) |
| Nasutitermes walkeri | TTAATTAAAATGAGATTTCCATCTATTTTCACTGCCGTCTTATTTGCAGCCTCAAGTGC<br>TTTAGCAGCCTATGATTACAAACAAGTATTGAGAGATTCCTTATTGTTCTACGAAGCT<br>CAGAGAAGCGGTAGATTACCAGCAGACCAGAAGGTCACCTGGAGAAAAGATTCCGC<br>CTTGAATGATCAGGGAGAGCAAGGTCAAGACTTAACCGGAGGTTATTTTGACGCCGG<br>TGATTTTGTGAAGTTTGGATTCCCAATGGCTTACGCAACCGTTTTGGCCTGGGGT<br>TTAATCGACTTTGAAGCCGGTTACTCTTCTGCTGGTGCCTTGGACGATGGTAGAAAAG<br>CAGTAAAGTGGGCTACTGATTACTTTATAAAAGCCCATACTTCTCAAAACGAGTTTTA<br>CGGACAAGTCGGTCAGGGTGACGTAGATCACGCATATTGGGGACGTCCTGAAGATAT<br>GACAATGGCTAGACCAGCCTACAAGATTGATACCAGCAGACCAGGATCTGACTTAGC<br>AGGAGAAACTGCTGCAGCTTTGGCTGCCGCATCCATCGTTTTCAAGAATGTAGATGG<br>TACATATTCCAACAACTTACTTACTCATGCTAGACAGTTGTTTGATTTCGCCAACAAT<br>TACAGAGGAAAATACTCTGATAGTATTACCGATGCAAGAAACTTTTACGCTAGTGCC<br>GACTATAGAGATGAGTTAGTCTGGGCAGCTGCCTGGTTGTACAGACAACCAACGAC<br>AATTCTTACTTGAACACTGCTGAATCATTATACAACGAGTTTGGATTGCAAAATTGGG<br>GTGGAGGGTTAAACTGGGATTCTAAAGTGAGTGGTGTTCAAGTTTTGTTAGCCAAGTT<br>GACCAACAAAAAGAGTATAAGGACACTATTCAATCATACGTGAATTACTTAATCAA<br>TAACCAACAGAAAACTCCAAAGGGATTGTTATACATTGACATGTGGGGGACCTTGAG<br>ACACGCAGCTAACGCAGCCTTTATAATGTTAGAAGCTGCCGACTTAGGTTTATCCGCT<br>TCATCTTATAGACAGTTCGCCCAAACACAAATAGACTACGCATTGGGGGACGGTGGA<br>CGTTCTTTTGTCTGTGGTTTCGGTTCTAATCCTCCAACTAGACCTCATCATAGATCCAG<br>TTCATGCCCGCCTGCTCCAGCTACCTGTGATTGGAATACATTCAATTCTCCTGACCCA<br>AACTACAATGTTTTATCCGGTGCCTTGGTTGGTCCTGACCAGAATGATAACTACG<br>TGGACGATAGAAGTGATTACGTCCATAATGAGGTAGCAACTGACTACAATGCCGGTT<br>TCCAATCAGCCTTAGCCGCTTTAGTCGCCTTAGGTTACTAAGGCGCGCC<br>(SEQ ID NO: 18) | Accession No: AB013273<br>MRVFLCLLSALALCQAAYDYKQVL<br>RDSLLFYEAQRSGRLPADQKVTWR<br>KDSALNDQGEQGQDLTGGYFDAGD<br>FVKFGFPMAYTATVLAWGLIDFEAG<br>YSSAGALDDGRKAVKWATDYFIKA<br>HTSQNEFYGQVGQGDVDHAYWGR<br>PEDMTMARPAYKIDTSRPGSDLAGE<br>TAAALAAASIVFKNVDGTYSNNLLT<br>HARQLFDFANNYRGKYSDSITDARN<br>FYASADYRDELVWAAAWLYRATN<br>DNSYLNTAESLYNEFGLQNWGGGL<br>NWDSKVSGVQVLLAKLTNKQEYKD<br>TIQSYVNYLINNQQKTPKGLLYIDM<br>WGTLRHAANAAFIMLEAADLGLSA<br>SSYRQFAQTQIDYALGDGGRSFVCG<br>FGSNPPTRPHHRSSSCPPAPATCDWN<br>TFNSPDPNYNVLSGALVGGPDQNDN<br>YVDDRSDYVHNEVATDYNAGFQSA<br>LAALVALGY<br>(SEQ ID NO: 38) |
| Nasutitermes takasagoensis | TTAATTAAAATGAGATTTCCATCTATTTTCACTGCCGTCTTATTTGCAGCCTCCAGTGC<br>ATTAGCAGCCTATGATTATAAACAAGTTTTGAGAGATTCCTTATTGTTCTACGAAGCT<br>CAGAGAAGCGGTAGATTACCAGCAGACCAGAAGGTCACTTGGAGAAAAGATTCAGC<br>CTTGAATGATCAGGGAGATCAAGGTCAAGACTTAACCGGAGGTTATTTTGACGCCGG<br>TGATTTTGTGAAATTTGGTTTCCCAATGGCATATACTGCTACCGTCTTGGCCTGGGGT | Accession No: AB013272<br>MRVFLCLLSALALCQAAYDYKQVL<br>RDSLLFYEAQRSGRLPADQKVTWR<br>KDSALNDQGDQGQDLTGGYFDAGD<br>FVKFGFPMAYTATVLAWGLIDFEAG |

TABLE 3-continued

Termite cellulase genes constructed

| Donor organism | DNA sequence used | Accession number and amino acid sequence |
|---|---|---|
| | TTAATCGATTTTGAGGCAGGATACAGTTCCGCTGGTGCCTTGGATGACGGTAGAAAA<br>GCAGTAAAGTGGGCAACTGATTACTTTATAAAGGCCCACACTTCACAGAATGAGTTT<br>TACGGACAAGTCGGTCAGGGTGACGCTGATCACGCTTTCTGGGGACGTCCTGAAGAT<br>ATGACCATGGCTAGACCAGCCTACAAGATTGACACCAGCAGACCAGGTAGTGACTTA<br>GCGGGTGAAACCGCAGCGGCATTGGCAGCTGCCAGTATCGTGTTTAGAAATGTTGAT<br>GGTACATACTCTAACAACTTACTTACTCATGCCAGACAATTATTTGACTTTGCAAATA<br>ACTACAGAGGAAAATACTCAGATTCCATAACCGACGCTAGAAACTTTTACGCCAGTG<br>CAGATTACCGTGACGAATTGGTTTGGGCTGCCGCATGGTTGTACAGAGCTACAAATG<br>ACAACACTTACTTGAATACCGCAGAATCCTTGTATGATGAATTTGGATTGCAGAACTG<br>GGGTGGAGGGTTAAACTGGGATTCAAAGGTGTCTGGTGTCCAGGTCTTGTTAGCAAA<br>ATTGACCAACAAACAGGCTTACAAAGATACTGTGCAGTCTTACGTGAATTACCTGAT<br>TAATAACCAGCAAAAGACCCCAAAAGGATTGTTATACATTGATATGTGGGGTACATT<br>GAGACACGCCGCAAATGCTGCATTCATCATGTTGGAAGCTGCCGAGTTGGGTTTATC<br>CGCATCATCTTACAGACAGTTTGCTCAAACTCAGATCGACTACGCTTTGGGTGACGGT<br>GGAAGAAGTTTCGTCTGTGGTTTTGGTTCAAACCCTCCTACAAGACCACATCATCGTT<br>CTTCCAGTTGCCCGCCTGCCCCAGCAACTTGTGACTGGAATACATTCAACTCACCTGA<br>CCCAAATTACCACGTGTTATCTGGAGCTTTGGTAGGAGGACCAGATCAAAACGATAA<br>TTATGTGGATGATAGATCCGACTACGTCCATAACGAAGTGGCAACCGACTACAACGC<br>CGGATTTCAGAGTGCTTTGGCAGCCTTAGTTGCTTTGGGTTATTAAGGCGCGCC<br>(SEQ ID NO: 19) | YSSAGALDDGRKAVKWATDYFIKA<br>HTSQNEFYGQVGQGDADHAFWGRP<br>EDMTMARPAYKIDTSRPGSDLAGET<br>AAALAAASIVFRNVDGTYSNNLLTH<br>ARQLFDFANNYRGKYSDSITDARNF<br>YASADYRDELVWAAAWLYRATND<br>NTYLNTAESLYDEFGLQNWGGGLN<br>WDSKVSGVQVLLAKLTNKQAYKDT<br>VQSYVNYLINNQQKTPKGLLYIDM<br>WGTLRHAANAAFIMLEAAELGLSAS<br>SYRQFAQTQIDYALGDGGRSFVCGF<br>GSNPPTRPHHRSSSCPPAPATCDWN<br>TFNSPDPNYHVLSGALVGGPDQNDN<br>YVDDRSDYVHNEVATDYNAGFQSA<br>LAALVALGY<br>(SEQ ID NO: 39) |
| Panesthia cribrata | TTAATTAAAATGAGATTTCCATCTATTTTCACTGCTGTTTTGTTCGCAGCCTCAAGTGC<br>TTTAGCCGCAACTTATGATTACTCCCAATTGATCCAGTATTCCTTATTGTTCTACGAGG<br>CTCAGAGAAGTGGAAAATTGCCAGCCGATCAGAAGGTGACCTGGAGAAAAGATTCC<br>GCATTAAATGACAAGGGACAAAATGGTGAGGACTTAACTGGAGGATATTACGATGCC<br>GGTGATTATGTCAAATTTGGATACCCAATGGCCTTTACAGCAACCTTGTTAGCCTGGA<br>GTTTGATTGACTATGAACAAGGTTATGCAAAGGCTAATTCCGTCGAGGACGCGAGAA<br>AGGCAGTGAAATGGGCCACTGACTATTTCTTAAAAGCCCATGTATCAGAACACGAGT<br>TCTACGGACAGGTGGGAGAGGGAAACTTGGATCATAATTCATGGGGACGTCCTGAGG<br>ACATGACTATGGAAAGACCAGCATATAAGATTGATGAGCAAAACCCTGGAACCGAA<br>TTAGCTGCCGAAACTGCTGCAGCCTTAGCCGCTGCCTCCATCGTGTTCAAATCTGTTG<br>ACCCTAGTTACTCCAATACATTACTTACTCACGCTAAACAATTGTATGACTTTGGTGA<br>TAACTTTAGAGGAAAATACAGTGAATCCATAAACGACGCCCAACATTCACTCTATAGATC<br>AAACGAATTTGAGGACGAATTGGTTTGGGGTGCCTTATGGTTGTACAAGGCTACTAT<br>GGATGAGAGTTTCTTAACAAAAGCCCAACAGTACTATGACGATTTTGGAATTGCCGA<br>GTATAATCCTTGGTTCAGTTGGGACCAGAAATGTACTTCCTCACAGTTGTTATTGGCA<br>CAAATTACCCAGGACACAACAATACATAGACACAAAATCACTGCTTATTGTGACCATATG<br>ATTTCAGGACAGCAAAGAACTCCAAAGGGTTTAGTGTACATTGACACTTGGGGTTCT<br>TTGAGAATGGCCGCAAACGCTGCCTACTTATGTTTGGAAGCAGCTTCAGCCGGTTTAA<br>AACCTACAGAGTACAGAGCATTCGCAACAGAACAAATAGGATACGCATTGGGTGAT<br>ACAGGAAAATCTTTCGTGGTTGGATTTGGTGTTAACCCACCTTCCCATGAAAGTCACA<br>GATCATCTTCCTGCCCAGACGCTCCAGCCCCTTGTGATTGGGTAACATATGGTAGTGT<br>CGATCCAAACCCTCATGTGTTATACGGAGCAATTGTTGGTGGACCAGGTCCTAACGA<br>TGAATATGATGACCAGAGATACGATTATGTACACAATGAAGTCGCTGATGACTACAA<br>CGCTGGTTATCAAGGATGCCTGGCCGCTTTGAACGAGTTGTAAGGCGCGCC<br>(SEQ ID NO: 20) | Accession No: AF220597<br>MKIILLFLGGLALCQGATYDYSQLIQ<br>YSLLFYEAQRSGKLPADQKVTWRK<br>DSALNDKGQNGEDLTGGYYDAGDY<br>VKFGYPMAFTATLLAWSLIDYEQGY<br>AKANSVEDARKAVKWATDYFLKA<br>HVSEHEFYGQVGEGNLDHNSWGRP<br>EDMTMERPAYKIDEQNPGTELAAET<br>AAALAAASIVFKSVDPSYSNTLLTH<br>AKQLYDFGDNFRGKYSESINDAQQF<br>YRSNEFEDELVWGALWLYKATMDE<br>SFLTKAQQYYDDFGIAEYNPWFSW<br>DQKCTSSQLLLAQITQEQQYIDKITA<br>YCDHMISGQQRTPKGLVYIDTWGSL<br>RMAANAAYLCLEAASAGLKPTEYR<br>AFATEQIGYALGDTGKSFVVGFGVN<br>PPSHESHRSSSCPDAPAPCDWVTYG<br>SVDPNPHVLYGAIVGGPGPNDEYDD<br>QRYDYVHNEVADDYNAGYQGCLA<br>ALNEL<br>(SEQ ID NO: 40) |

When using the methods above, the term "about" is used precisely to account for fractional percentages of codon frequencies for a given amino acid. As used herein, "about" is defined as one amino acid more or one amino acid less than the value given. The whole number value of amino acids is rounded up if the fractional frequency of usage is 0.50 or greater, and is rounded down if the fractional frequency of use is 0.49 or less. Using again the example of the frequency of usage of leucine in human genes for a hypothetical polypeptide having 62 leucine residues, the fractional frequency of codon usage would be calculated by multiplying 62 by the frequencies for the various codons. Thus, 7.28 percent of 62 equals 4.51 UUA codons, or "about 5," i.e., 4, 5, or 6 UUA codons, 12.66 percent of 62 equals 7.85 UUG codons or "about 8," i.e., 7, 8, or 9 UUG codons, 12.87 percent of 62 equals 7.98 CUU codons, or "about 8," i.e., 7, 8, or 9 CUU codons, 19.56 percent of 62 equals 12.13 CUC codons or "about 12," i.e., 11, 12, or 13 CUC codons, 7.00 percent of 62 equals 4.34 CUA codons or "about 4," i.e., 3, 4, or 5 CUA codons, and 40.62 percent of 62 equals 25.19 CUG codons, or "about 25," i.e., 24, 25, or 26 CUG codons.

Randomly assigning codons at an optimized frequency to encode a given polypeptide sequence, can be done manually by calculating codon frequencies for each amino acid, and then assigning the codons to the polypeptide sequence randomly. Additionally, various algorithms and computer software programs are readily available to those of ordinary skill in the art. For example, the "EditSeq" function in the Lasergene Package, available from DNAstar, Inc., Madison, Wis., the backtranslation function in the VectorNTI Suite, available from InforMax, Inc., Bethesda, Md., and the "backtranslate" function in the GCG—Wisconsin Package, available from Accelrys, Inc., San Diego, Calif. In addition, various resources are publicly available to codon-optimize coding region sequences, e.g., the "backtranslation" function at http://www.entelechon.com/bioinformatics/backtranslation.php?lang=eng (visited Apr. 15, 2008) and the "backtranseq" function available at http://bioinfo.pbi.nrc.ca:8090/EMBOSS/index.html (visited Jul. 9, 2002). Constructing a rudimentary algorithm to assign codons based on a given frequency can also easily be accomplished with basic mathematical functions by one of ordinary skill in the art.

A number of options are available for synthesizing codon optimized coding regions designed by any of the methods described above, using standard and routine molecular biological manipulations well known to those of ordinary skill in the art. In one approach, a series of complementary oligonucleotide pairs of 80-90 nucleotides each in length and spanning the length of the desired sequence are synthesized by standard methods. These oligonucleotide pairs are synthesized such that upon annealing, they form double stranded fragments of 80-90 base pairs, containing cohesive ends, e.g., each oligonucleotide in the pair is synthesized to extend 3, 4, 5, 6, 7, 8, 9, 10, or more bases beyond the region that is complementary to the other oligonucleotide in the pair. The single-stranded ends of each pair of oligonucleotides is designed to anneal with the single-stranded end of another pair of oligonucleotides. The oligonucleotide pairs are allowed to anneal, and approximately five to six of these double-stranded fragments are then allowed to anneal together via the cohesive single stranded ends, and then they ligated together and cloned into a standard bacterial cloning vector, for example, a TOPO® vector available from Invitrogen Corporation, Carlsbad, Calif. The construct is then sequenced by standard methods. Several of these constructs consisting of 5 to 6 fragments of 80 to 90 base pair fragments ligated together, i.e., fragments of about 500 base pairs, are prepared, such that the entire desired sequence is represented in a series of plasmid constructs. The inserts of these plasmids are then cut with appropriate restriction enzymes and ligated together to form the final construct. The final construct is then cloned into a standard bacterial cloning vector, and sequenced. Additional methods would be immediately apparent to the skilled artisan. In addition, gene synthesis is readily available commercially.

In certain embodiments, an entire polypeptide sequence, or fragment, variant, or derivative thereof is codon optimized by any of the methods described herein. Various desired fragments, variants or derivatives are designed, and each is codon-optimized individually. In addition, partially codon-optimized coding regions of the present invention can be designed and constructed. For example, the invention includes a nucleic acid fragment of a codon-optimized coding region encoding a polypeptide in which at least about 1%, 2%, 3%, 4%, 5%, 10%, 15%, 20%, 25%, 30%, 35%, 40%, 45%, 50%, 55%, 60%, 65%, 70%, 75%, 80%, 85%, 90%, 95%, or 100% of the codon positions have been codon-optimized for a given species. That is, they contain a codon that is preferentially used in the genes of a desired species, e.g., a yeast species such as *Saccharomyces cerevisiae*, in place of a codon that is normally used in the native nucleic acid sequence.

In some embodiments of the present invention, the codon-optimized polynucleotide encoding the termite or termite-associated symbiont cellulase is about 85%, about 80%, about 75%, about 70%, about 65%, about 60%, about 55% or about 50% identical to the endogenous coding sequence. In some embodiments the codon-optimized polynucleotide encoding the termite or termite-associated symbiont cellulase is less than about 95%, about 90%, about 85%, about 80%, about 75%, about 70%, about 65%, about 60%, about 55%, or about 50% identical to the endogenous coding sequence. In some embodiments, the codon-optimized polynucleotide encoding the termite or termite-associated symbiont cellulase is from about 50% to about 95%, from about 60% to about 95%, from about 70% to about 95%, from about 80% to about 95% or from about 90% to about 95% identical to the endogenous coding sequence. In some embodiments, the codon-optimized polynucleotide encoding the termite or termite-associated symbiont cellulase is from about 50% to about 90%, from about 60% to about 90%, from about 70% to about 90% or from about 80% to about 90% identical to the endogenous coding sequence. In some embodiments, the codon-optimized polynucleotide encoding the termite or termite-associated symbiont cellulase is from about 50% to about 85%, from about 60% to about 85% or from about 70% to about 85% identical to the endogenous coding sequence. In some embodiments, the codon-optimized polynucleotide encoding the termite or termite-associated symbiont cellulase is from about 50% to about 80%, from about 60% to about 80% or from about 70% to about 80% identical to the endogenous coding sequence. In some embodiments, the codon-optimized polynucleotide encoding the termite or termite-associated symbiont cellulase is from about 50% to about 75% or from about 60% to about 75% identical to the endogenous coding sequence. In some embodiments, the codon-optimized polynucleotide encoding the termite or termite-associated symbiont cellulase is from about 50% to about 70% or from about 60% to about 70% identical to the endogenous coding sequence.

In additional embodiments, a full-length polypeptide sequence is codon-optimized for a given species resulting in a codon-optimized coding region encoding the entire polypeptide, and then nucleic acid fragments of the codon-optimized coding region, which encode fragments, variants, and derivatives of the polypeptide are made from the original codon-optimized coding region. As would be well understood by those of ordinary skill in the art, if codons have been randomly assigned to the full-length coding region based on their frequency of use in a given species, nucleic acid fragments encoding fragments, variants, and derivatives would not necessarily be fully codon optimized for the given species. However, such sequences are still much closer to the codon usage of the desired species than the native codon usage. The advantage of this approach is that synthesizing codon-optimized nucleic acid fragments encoding each fragment, variant, and derivative of a given polypeptide, although routine, would be time consuming and would result in significant expense.

The codon-optimized coding regions can be versions encoding a termite or termite-associated symbiont cellulase or domains, fragments, variants, or derivatives thereof.

Codon optimization is carried out for a particular species by methods described herein. For example, in certain embodiments codon-optimized coding regions encoding termite cellulases or termite-associated symbiont cellulases, or domains, fragments, variants, or derivatives thereof that are optimized according to yeast codon usage, e.g., *Saccharomyces cerevisiae, Kluveromyces lactus* or both. In particular, the present invention relates to codon-optimized coding regions encoding polypeptides of termite cellulases or termite-associated symbiont cellulases, or domains, variants or derivatives thereof which have been optimized according to yeast codon usage, for example, *Saccharomyces cerevisiae* and *Kluveromyces lactus* codon usage. Also provided are polynucleotides, vectors, and other expression constructs comprising codon-optimized coding regions encoding termite cellulases or termite-associated symbiont cellulases, or domains, fragments, variants, or derivatives thereof, and various methods of using such polynucleotides, vectors and other expression constructs.

In certain embodiments described herein, a codon-optimized coding region encoding any of SEQ ID NOs: 21-40, or domain, fragment, variant, or derivative thereof, is optimized according to codon usage in yeast (e.g. *Saccharomyces cerevisiae*). Alternatively, a codon-optimized coding region encoding any of SEQ ID NOs: 21-40 may be optimized according to codon usage in any plant, animal, or microbial species. In certain embodiments, the codon-optimized coding region is a polynucleotide comprising a nucleotide sequence selected from the group consisting of SEQ ID NOs: 1-20, or a fragment thereof.

Polynucleotides of the Invention

The present invention provides for polynucleotides comprising a nucleic acid fragment which encodes at least 50 amino acids of a cellulase, wherein said nucleic acid fragment is codon-optimized for expression in a yeast strain and wherein the cellulase is a termite cellulase or a termite-associated cellulase. In some embodiments, the cellulase is a cellulase comprising the amino acid sequence of SEQ ID NOs: 21-40, or a fragment, variant or derivative thereof. In some embodiments, the cellulase is encoded by a polynucleotide of SEQ ID NOs: 1-20 or a fragment, variant or derivative thereof.

The present invention also provides for the use of an isolated polynucleotide comprising a nucleic acid at least about 70%, 75%, or 80% identical, at least about 90% to about 95% identical, or at least about 96%, 97%, 98%, 99% or 100% identical to any of SEQ ID NOs:1-20, or fragments, variants, or derivatives thereof.

In certain aspects, the present invention relates to a polynucleotide comprising a nucleic acid encoding a functional or structural domain of a termite cellulase or termite-associated symbiont cellulase. The present invention also encompasses an isolated polynucleotide comprising a nucleic acid that is about 70%, 75%, or 80% identical, at least about 90% to about 95% identical, or at least about 96%, 97%, 98%, 99% or 100% identical to a nucleic acid encoding a functional or structural domain of a termite cellulase or termite-associated symbiont cellulase.

The present invention also encompasses variants of a termite cellulase or termite-associated symbiont cellulase. Variants may contain alterations in the coding regions, non-coding regions, or both. Examples are polynucleotide variants containing alterations which produce silent substitutions, additions, and/or deletions, but do not alter the properties or activities of the encoded polypeptide, e.g. the biological activity such as cellulase activity. For example, polynucleotide variants include one or several nucleic acid deletions, substitutions and/or additions, where the encoded variant retains cellulase activity. In certain embodiments, nucleotide variants are produced by silent substitutions due to the degeneracy of the genetic code. In further embodiments, termite cellulase or termite-associated symbiont cellulase polynucleotide variants can be produced for a variety of reasons, e.g., to optimize codon expression for a particular host as described above (e.g., change codons in the termite cellulase or termite-associated symbiont cellulase mRNA to those preferred by a host such as the yeast *Saccharomyces cerevisiae*).

The present invention also encompasses an isolated polynucleotide comprising a nucleic acid that is about 70%, 75%, or 80% identical, at least about 90% to about 95% identical, or at least about 96%, 97%, 98%, 99% or 100% identical to a nucleic acid encoding a fusion protein, where the nucleic acid comprises: (1) a first polynucleotide, where the first polynucleotide encodes for a termite cellulase or termite-associated symbiont cellulase, or domain, fragment, variant, or derivative thereof; and (2) one or more additional polynucleotides, where the one or more additional polynucleotides encodes for a termite cellulase or termite-associated symbiont cellulase, or domain, fragment, variant, or derivative thereof.

In certain embodiments, the nucleic acid encoding a fusion protein comprises a first polynucleotide encoding for a termite cellulase or termite-associated symbiont cellulase or domain, fragment, variant or derivative thereof and a second polynucleotide encoding for the *S. cerevisiae* alpha mating factor signal sequence.

In certain embodiments, the nucleic acid encoding a fusion protein comprises a first polynucleotide encoding for a termite cellulase or termite-associated symbiont cellulase and one or more additional polynucleotides encoding for a cellulose binding domain (CBM) domain. In one embodiment, the CBM domain is the CBM domain of *T. reesei* cbh1 or *T. reesei* cbh2. The amino acid sequence of the CBM domains of *T. reesei* Cbh1 and *T. reesei* Cbh2 are as follows:

```
T. reesei Cbh1
                                        (SEQ ID NO: 41)
HYGQCGGIGYSGPTVCASGTTCQVLNPYYSQCL T. reesei Cbh2
                                        (SEQ ID NO: 42)
VYSNDYYSQCLPGAASSSSSTRAASTTSRVSP
```

In one particular embodiment the nucleic acid encoding a fusion protein includes a first polynucleotide that is a codon-optimized termite cellulase or termite-associated symbiont cellulase, and the one or more additional polynucleotides encodes for a codon-optimized CBM of *T. reesei* Cbh1 or Cbh2.

In further embodiments of the fusion protein, the first polynucleotide is either 5' (i.e. upstream) or 3' (i.e. downstream) to the one or more additional polynucleotides. In certain other embodiments, the first polynucleotide and/or the one or more additional polynucleotides are encoded by codon-optimized polynucleotides, for example, polynucleotides codon-optimized for *S. cerevisiae*.

Also provided in the present invention are allelic variants, orthologs, and/or species homologs. Procedures known in the art can be used to obtain full-length genes, allelic variants, splice variants, full-length coding portions, orthologs, and/or species homologs of genes corresponding to any of SEQ ID NOs: 1-20, using information from the sequences disclosed herein. For example, allelic variants and/or species homologs may be isolated and identified by making suitable probes or primers from the sequences provided herein and screening a suitable nucleic acid source for allelic variants and/or the desired homologue.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the particular polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence shown of any of SEQ ID NOs:1-20, or any fragment or domain specified as described herein.

As a practical matter, whether any particular nucleic acid molecule or polypeptide is at least 80%, 85%, 90%, 95%, 96%, 97%, 98% or 99% identical to a nucleotide sequence or polypeptide of the present invention can be determined conventionally using known computer programs. A method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* (1990) 6:237-245.) In a sequence alignment the query and subject sequences are both DNA sequences. An RNA sequence can be compared by converting U's to T's. The result of said global sequence alignment is in percent identity. Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty 0.05, Window Size=500 or the length of the subject nucleotide sequence, whichever is shorter.

If the subject sequence is shorter than the query sequence because of 5' or 3' deletions, not because of internal deletions, a manual correction must be made to the results. This is because the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of the present invention. Only bases outside the 5' and 3' bases of the subject sequence, as displayed by the FASTDB alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are to be made for the purposes of the present invention.

Some embodiments of the invention encompass a nucleic acid molecule comprising at least 10, 20, 30, 35, 40, 50, 60, 70, 80, 90, 100, 200, 300, 400, 500, 600, 700, or 800 consecutive nucleotides or more of any of SEQ ID NOs:1-20, or domains, fragments, variants, or derivatives thereof.

The polynucleotide of the present invention may be in the form of RNA or in the form of DNA, which DNA includes cDNA, genomic DNA, and synthetic DNA. The DNA may be double stranded or single-stranded, and if single stranded may be the coding strand or non-coding (anti-sense) strand. The coding sequence which encodes the mature polypeptide may be identical to the coding sequence encoding SEQ ID NOs: 21-40 or may be a different coding sequence which coding sequence, as a result of the redundancy or degeneracy of the genetic code, encodes the same mature polypeptide as the DNA of any one of SEQ ID NOs:1-20.

In certain embodiments, the present invention provides an isolated polynucleotide comprising a nucleic acid fragment which encodes at least 10, at least 20, at least 30, at least 40, at least 50, at least 60, at least 70, at least 80, at least 90, at least 95, at least 100, at least 150, at least 200, at least 250, at least 300 or at least 350 or more contiguous amino acids of SEQ ID NOs: 21-40.

The polynucleotide encoding for the mature polypeptide comprising the amino acid sequence of SEQ ID NOs:21-40 may include, for example, only the coding sequence for the mature polypeptide; the coding sequence of any domain of the mature polypeptide; the coding sequence for the mature polypeptide and the coding sequence for a fusion polypeptide; and the coding sequence for the mature polypeptide (or domain-encoding sequence) together with non-coding sequence, such as introns or non-coding sequence 5' and/or 3' of the coding sequence for the mature polypeptide.

Thus, the term "polynucleotide encoding a polypeptide" encompasses a polynucleotide which includes only sequences encoding for the polypeptide as well as a polynucleotide which includes additional coding and/or non-coding sequences. In some embodiments of the present invention, the polynucleotide encodes at least about 100, 150, 200, 250, 300 or 350 contiguous amino acids of a termite cellulase or a termite-associated symbiont cellulase.

In further aspects of the invention, nucleic acid molecules having sequences at least about 70%, 75%, 80%, 85%, 90%, 95%, 96%, 97%, 98% or 99% identical to the nucleic acid sequences disclosed herein, encode a polypeptide having cellulase functional activity. By "a polypeptide having cellulase functional activity" is intended polypeptides exhibiting activity similar, but not necessarily identical, to a functional activity of the cellulase polypeptides of the present invention, as measured, for example, in a particular biological assay. For example, a cellulase functional activity can routinely be measured by determining the ability of a cellulase polypeptide to hydrolyze cellulose, i.e. by measuring the level of cellulase activity Of course, due to the degeneracy of the genetic code, one of ordinary skill in the art will immediately recognize that a large portion of the nucleic acid molecules having a sequence at least about 90%, 95%, 96%, 97%, 98%, or 99% identical to the nucleic acid sequence of any of SEQ ID NOs:1-20, or fragments thereof, will encode polypeptides "having cellulase functional activity." In fact, since degenerate variants of any of these nucleotide sequences all encode the same polypeptide, in many instances, this will be clear to the skilled artisan even without performing the above described comparison assay. It will be further recognized in the art that, for such nucleic acid molecules that are not degenerate variants, a reasonable number will also encode a polypeptide having cellulase functional activity.

Fragments of the full length gene of the present invention may be used as a hybridization probe for a cDNA library to isolate the full length cDNA and to isolate other cDNAs which have a high sequence similarity to the termite cellulase and termite-associated symbiont cellulase genes of the present invention, or a gene encoding for a protein with similar biological activity. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

In certain embodiments, a hybridization probe may have at least 30 bases and may contain, for example, 50 or more bases. The probe may also be used to identify a cDNA clone corresponding to a full length transcript and a genomic clone or clones that contain the complete gene including regulatory and promoter regions, exons, and introns. An example of a screen comprises isolating the coding region of the gene by using the known DNA sequence to synthesize an oligonucleotide probe. Labeled oligonucleotides having a sequence complementary to that of the gene of the present invention are used to screen a library of bacterial or fungal cDNA, genomic DNA or mRNA to determine which members of the library the probe hybridizes to.

The present invention further relates to polynucleotides which hybridize to the hereinabove-described sequences if there is at least about 70%, at least about 90%, or at least about 95% identity between the sequences. The present invention particularly relates to polynucleotides which hybridize under stringent conditions to the hereinabove-described polynucleotides. As herein used, the term "stringent conditions" means hybridization will occur only if there is at least about 95% or at least about 97% identity between the sequences. In certain aspects of the invention, the polynucleotides which hybridize to the hereinabove described polynucleotides encode polypeptides which either retain substantially the same biological function or activity as the mature polypeptide encoded by the DNAs of any of SEQ ID NOs:1-20.

Alternatively, polynucleotides which hybridize to the hereinabove-described sequences may have at least 20 bases, at least 30 bases, or at least 50 bases which hybridize to a polynucleotide of the present invention and which has an identity thereto, as hereinabove described, and which may or may not retain activity. For example, such polynucleotides may be employed as probes for the polynucleotide of any of SEQ ID NOs: 1-20, for example, for recovery of the polynucleotide or as a diagnostic probe or as a PCR primer.

Hybridization methods are well defined and have been described above. Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

For example, genes encoding similar proteins or polypeptides to those of the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (see, e.g., Maniatis, 1989). Moreover, the entire sequences can be used directly to synthesize DNA probes by methods known to the skilled artisan such as random primers DNA labeling, nick translation, or end-labeling techniques, or RNA probes using available in vitro transcription systems.

In certain aspects of the invention, polynucleotides which hybridize to the hereinabove-described sequences having at least 20 bases, at least 30 bases, or at least 50 bases which hybridize to a polynucleotide of the present invention may be employed as PCR primers. Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. Generally two short segments of the instant sequences may be used in polymerase chain reaction (PCR) protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Therefore, the nucleic acid sequences and fragments thereof of the present invention may be used to isolate genes encoding homologous proteins from the same or other fungal species or bacterial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, Mullis et al., U.S. Pat. No. 4,683, 202; ligase chain reaction (LCR) (Tabor, S. et al., *Proc. Acad. Sci. USA* 82, 1074, (1985)); or strand displacement amplification (SDA, Walker, et al., *Proc. Natl. Acad. Sci. U.S.A.*, 89, 392, (1992)).

The polynucleotides of the present invention can also comprise nucleic acids encoding a termite cellulase or termite-associated symbiont cellulase, or domain, fragment, variant, or derivative thereof, fused in frame to a marker sequence which allows for detection of the polypeptide of the present invention. The marker sequence may be a yeast selectable marker selected from the group consisting of URA3, HIS3, LEU2, TRP1, LYS2, ADE2 or SMR1. Additional marker sequences include other auxotrophic markers or dominant markers known to one of ordinary skill in the art such as ZEO (zeocin), NEO (G418), hyromycin, arsenite, HPH, NAT and the like.

Polypeptides of the Invention

The present invention further relates to the expression of termite cellulase or termite-associated symbiont cellulase polypeptides in a yeast host cell, such as *Saccharomyces cerevisiae*. The sequences of several examples of termite cellulase or termite-associated symbiont cellulase polypeptides are set forth above and summarized in Table 3.

The present invention further encompasses polypeptides which comprise, or alternatively consist of, an amino acid sequence which is at least about 80%, 85%, 90%, 95%, 96%, 97%, 98%, 99% identical to, for example, the polypeptide sequence shown in SEQ ID NOs: 21-40, and/or domains, fragments, variants, or derivative thereof, of any of these polypeptides (e.g., those fragments described herein, or domains of any of SEQ ID NOs: 21-40).

By a polypeptide having an amino acid sequence at least, for example, 95% "identical" to a query amino acid sequence of the present invention, it is intended that the amino acid sequence of the subject polypeptide is identical to the query sequence except that the subject polypeptide sequence may include up to five amino acid alterations per each 100 amino acids of the query amino acid sequence. In other words, to obtain a polypeptide having an amino acid sequence at least 95% identical to a query amino acid sequence, up to 5% of the amino acid residues in the subject sequence may be inserted, deleted, (indels) or substituted with another amino acid. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence of SEQ ID NOs: 21-40 can be determined conventionally using known computer programs. As discussed above, a method for determining the best overall match between a query sequence (a sequence of the present invention) and a subject sequence, also referred to as a global sequence alignment, can be determined using the FASTDB computer program based on the algorithm of Brutlag et al. (*Comp. App. Biosci.* 6:237-245 (1990)). In a sequence alignment the query and subject sequences are either both nucleotide sequences or both amino acid sequences. The result of said global sequence alignment is in percent identity. Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. Also as discussed above, manual corrections may be made to the results in certain instances.

In certain embodiments, the polypeptide of the present invention encompasses a fusion protein comprising a first polypeptide, where the first polypeptide is a termite cellulase or a termite-associated symbiont cellulase or domain, fragment, variant, or derivative thereof, and one or more additional polypeptides. In some embodiments the one or more additional polypeptides is a signal sequence. The signal sequence can be from any organism. For example, in some embodiments, the one or more additional polypeptides is an *S. cerevisiae* polypeptide. In one particular embodiment, the *S. cerevisiae* polypeptide is the *S. cerevisiae* alpha mating factor signal sequence. In some embodiments the signal sequence comprises the amino acid sequence MRFPSIFTAVLFAASSALA (SEQ ID NO: 43).

In certain embodiments, the polypeptide of the present invention encompasses a fusion protein comprising a first polypeptide, where the first polypeptide is a termite cellulase or a termite-associated symbiont cellulase or domain, fragment, variant, or derivative thereof, and one or more additional polypeptides, where the one or more additional polypeptides comprises a cellulose binding domain (CBM).

In some embodiments, the CBM is *Neosartorya fischeri* Cbh1, *H. grisea* Cbh1, *Chaetomium thermophilum* Cbh1, *T. reesei* Cbh1 or *T. reesei* Cbh2, or a domain, fragment, variant, or derivative thereof.

In further embodiments of the fusion protein, the first polypeptide is either N-terminal or C-terminal to the one or more additional polypeptides. In certain other embodiments, the first polypeptide and/or the one or more additional polypeptides are encoded by codon-optimized polynucleotides, for example, polynucleotides codon-optimized for expression in *S. cerevisiae*. In particular embodiments, the first polynucleotide is a codon-optimized termite cellulase or a termite-associated symbiont cellulase and the one or more additional polynucleotides encodes for a codon-optimized CBM from *T. reesei* Cbh1 or Cbh2. In certain other embodiments, the first polypeptide and the one or more additional polypeptides are fused via a linker sequence.

In certain aspects of the invention, the polypeptides and polynucleotides of the present invention are provided in an isolated form, e.g., purified to homogeneity.

The present invention also encompasses polypeptides which comprise, or alternatively consist of, an amino acid sequence which is at least 80%, 85%, 90%, 95%, 96%, 97%, 98%, 99% similar to a polypeptide comprising the amino acid sequence of any of SEQ ID NOs: 21-40, and to portions of such polypeptide with such portion of the polypeptide generally containing at least 30 amino acids and more preferably at least 50 amino acids.

As known in the art "similarity" between two polypeptides is determined by comparing the amino acid sequence and conserved amino acid substitutes thereto of the polypeptide to the sequence of a second polypeptide.

The present invention further relates to a domain, fragment, variant, derivative, or analog of the polypeptide comprising the amino acid sequence of any of SEQ ID NOs: 21-40.

Fragments or portions of the polypeptides of the present invention may be employed for producing the corresponding full-length polypeptide by peptide synthesis, therefore, the fragments may be employed as intermediates for producing the full-length polypeptides.

Fragments of termite cellulase and termite-associated symbiont cellulase polypeptides of the present invention encompass domains, proteolytic fragments, deletion fragments and in particular, fragments of termite cellulase and termite-associated symbiont cellulase polypeptides which retain any specific biological activity of the cellulase protein. Polypeptide fragments further include any portion of the polypeptide which comprises a catalytic activity of the cellulase protein.

The variant, derivative or analog of the polypeptide comprising the amino acid sequence of any of SEQ ID NOs: 21-40, can be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide for purification of the polypeptide or (v) one in which a fragment of the polypeptide is soluble, i.e., not membrane bound, yet still binds ligands to the membrane bound receptor. Such variants, derivatives and analogs are deemed to be within the scope of those skilled in the art from the teachings herein.

The polypeptides of the present invention further include variants of the polypeptides. A "variant" of the polypeptide can be a conservative variant, or an allelic variant. As used herein, a conservative variant refers to alterations in the amino acid sequence that does not adversely affect the biological functions of the protein. A substitution, insertion or deletion is said to adversely affect the protein when the altered sequence prevents or disrupts a biological function associated with the protein. For example, the overall charge, structure or hydrophobic-hydrophilic properties of the protein can be altered without adversely affecting a biological activity. Accordingly, the amino acid sequence can be altered, for example to render the peptide more hydrophobic or hydrophilic, without adversely affecting the biological activities of the protein.

A "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Alternatively, mutations can be introduced randomly along all or part of the coding sequence, such as by saturation mutagenesis, and the resultant mutants can be screened for biological activity to identify mutants that retain activity (e.g., cellulase activity).

By an "allelic variant" is intended alternate forms of a gene occupying a given locus on a chromosome of an organism. Genes II, Lewin, B., ed., John Wiley & Sons, New York (1985). Non-naturally occurring variants may be produced using art-known mutagenesis techniques. Allelic variants, though possessing a slightly different amino acid sequence than those recited above, will still have the same or similar biological functions associated with the termite cellulase or termite-associated symbiont cellulase protein.

In some embodiments, the allelic variants, the conservative substitution variants, and members of the termite cellulase or termite-associated symbiont cellulase protein family, will have an amino acid sequence having at least 75%, at least 80%, at least 90%, at least 95% amino acid sequence identity with a termite cellulase or termite-associated symbiont cellulase amino acid sequence set forth in any one of SEQ ID NOs:21-40. Identity or homology with respect to such sequences is defined herein as the percentage of amino acid residues in the candidate sequence that are identical with the known peptides, after aligning the sequences and introducing gaps, if necessary, to achieve the maximum percent homology, and not considering any conservative substitutions as part of the sequence identity. N terminal, C terminal or internal extensions, deletions, or insertions into the peptide sequence shall not be construed as affecting homology.

Thus, the proteins and peptides of the present invention include molecules comprising the amino acid sequence of SEQ ID NOs: 21-40 or fragments thereof having a consecutive sequence of at least about 3, 4, 5, 6, 10, 15, 20, 25, 30, 35 or more amino acid residues of the termite cellulase or termite-associated symbiont cellulase polypeptide sequence; amino acid sequence variants of such sequences wherein at least one amino acid residue has been inserted N- or C-terminal to, or within, the disclosed sequence; amino acid sequence variants of the disclosed sequences, or their fragments as defined above, that have been substituted by another residue. Contemplated variants further include those containing predetermined mutations by, e.g., homologous recombination, site-directed or PCR mutagenesis, and the corresponding proteins of other animal species, the alleles or other naturally occurring variants of the family of proteins, and derivatives wherein the protein has been covalently modified by substitution, chemical, enzymatic, or other appropriate means with a moiety other than a naturally occurring amino acid (for example, a detectable moiety such as an enzyme or radioisotope).

Using known methods of protein engineering and recombinant DNA technology, variants may be generated to improve or alter the characteristics of the termite or termite-associated symbiont cellulase. For instance, one or more amino acids can be deleted from the N-terminus or C-terminus of the secreted protein without substantial loss of biological function.

Thus, the invention further includes termite cellulase or termite-associated symbiont cellulase polypeptide variants which show substantial biological activity. Such variants include deletions, insertions, inversions, repeats, and substitutions selected according to general rules known in the art so as have little effect on activity. Polypeptide variants of the invention further include one or several amino acid deletions, substitutions and/or additions, where the variant retains substantial biological activity. For example, polypeptide variants include one or several amino acid deletions, substitutions and/or additions, where the variant retains cellulase activity.

The skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in Bowie et al., "Deciphering the Message in Protein Sequences: Tolerance to Amino Acid Substitutions," Science 247:1306-1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081-1085 (1989).) The resulting mutant molecules can then be tested for biological activity.

As the authors state, these two strategies have revealed that proteins are often surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved. Moreover, tolerated conservative amino acid substitutions involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

The terms "derivative" and "analog" refer to a polypeptide differing from the termite cellulase or termite-associated symbiont cellulase polypeptide, but retaining essential properties thereof. Generally, derivatives and analogs are overall closely similar, and, in many regions, identical to the termite cellulase or termite-associated symbiont cellulase polypeptides. The term "derivative" and "analog" when referring to termite cellulase or termite-associated symbiont cellulase polypeptides of the present invention include any polypeptides which retain at least some of the activity of the corresponding native polypeptide, e.g., the endogluconase activity, exogluconase activity, β-glucosidase activity or the activity of the catalytic domain of one of these proteins.

Derivatives of termite cellulase or termite-associated symbiont cellulase polypeptides of the present invention, are polypeptides which have been altered so as to exhibit additional features not found on the native polypeptide. Derivatives can be covalently modified by substitution, chemical, enzymatic, or other appropriate means with a moiety other than a naturally occurring amino acid (for example, a detectable moiety such as an enzyme or radioisotope). Examples of derivatives include fusion proteins.

An analog is another form of a termite cellulase or termite-associated symbiont cellulase polypeptide of the present invention. An "analog" also retains substantially the same biological function or activity as the polypeptide of interest, i.e., functions as a cellobiohydrolase. An analog includes a proprotein which can be activated by cleavage of the proprotein portion to produce an active mature polypeptide.

The polypeptide of the present invention may be a recombinant polypeptide, a natural polypeptide or a synthetic polypeptide, preferably a recombinant polypeptide.

Vectors Encoding Termite Cellulases and/or Termite-Associated Symbiont Cellulases The present invention also relates to vectors which include polynucleotides of the present invention. Vectors of the present invention may be, for example, a cloning vector for example, in the form of a plasmid, a viral particle, a phage, etc. In addition, the polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; and yeast plasmids. Both episomal vectors (such as pMU451) and integrative vectors (such as pMU562) can be used. The vector pMU562 is an integrative yeast expression vector that includes the following sequences: the intergenic region of phage f1; the pMB1 replicon responsible for the replication of phagemid; the gene coding for beta-lactamase that confers resistance to ampicillin; *S. cerevisiae* delta integration sites; *S. cerevisiae* ENO1 promoter; *S. cerevisiae* ENO1 terminator; *S. cerevisiae* TEF1 promoter; *S. cerevisiae* TEF1 terminator; *Streptoalloteichus hindustanus* ble Zeocin resistance gene; and Cre recombinase recognition site. Furthermore, any other vector that can be maintained in a host cell and allow for gene expression can be used.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively associated with an appropriate expression control sequence(s) (promoter) to direct mRNA synthesis. Representative examples of such promoters are as follows:

TABLE 4

Exemplary Promoters

| Gene | Organism | Systematic name | Reason for use/benefits |
|---|---|---|---|
| PGK1 | *S. cerevisiae* | YCR012W | Strong constitutive promoter |
| ENO1 | *S. cerevisiae* | YGR254W | Strong constitutive promoter |
| TDH3 | *S. cerevisiae* | YGR192C | Strong constitutive promoter |
| TDH2 | *S. cerevisiae* | YJR009C | Strong constitutive promoter |
| TDH1 | *S. cerevisiae* | YJL052W | Strong constitutive promoter |
| ENO2 | *S. cerevisiae* | YHR174W | Strong constitutive promoter |
| GPM1 | *S. cerevisiae* | YKL152C | Strong constitutive promoter |
| TPI1 | *S. cerevisiae* | YDR050C | Strong constitutive promoter |

Additionally, promoter sequences from stress and starvation response genes are useful in the present invention. In some embodiments, promoter regions from the *S. cerevisiae* genes GAC1, GET3, GLC7, GSH1, GSH2, HSF1, HSP12, LCB5, LRE1, LSP1, NBP2, PIL1, PIM1, SGT2, SLG1, WHI2, WSC2, WSC3, WSC4, YAP1, YDC1, HSP104, HSP26, ENA1, MSN2, MSN4, SIP2, SIP4, SIP5, DPL1, IRS4, KOG1, PEP4, HAP4, PRB1, TAX4, ZPR1, ATG1, ATG2, ATG10, ATG11, ATG12, ATG13, ATG14, ATG15, ATG16, ATG17, ATG18, and ATG19 can be used. Any suitable promoter to drive gene expression in the host cells of the invention can be used.

Additionally the *E. coli*, lac or trp, and other promoters are known to control expression of genes in prokaryotic or lower eukaryotic cells. Promoter regions can be selected from any desired gene. Particular named yeast promoters include the constitute promoter ENO1, the PGK1 promoter, the TEF1 promoter and the HXT7 promoter. Particular named bacterial promoters include lacI, lacZ, T3, T7, gpt, lambda PR, PL and trp. Eukaryotic promoters include CMV immediate early, HSV thymidine kinase, early and late SV40, LTRs from retrovirus, and mouse metallothionein-I.

The expression vector also contains a ribosome binding site for translation initiation and a transcription terminator. The vector may also include appropriate sequences for amplifying expression, or may include additional regulatory regions.

In addition, the expression vectors may contain one or more sequences encoding selectable marker to provide a phenotypic trait for selection of transformed host cells such as URA3, HIS3, LEU2, TRP1, LYS2, ADE2, dihydrofolate reductase or neomycin (G418) resistance for eukaryotic cell culture, or tetracycline or ampicillin resistance in *E. coli*.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In one aspect of this embodiment, the construct further comprises regulatory sequences, including, for example, a promoter, operably associated to the sequence.

Large numbers of suitable vectors and promoters are known to those of skill in the art, and are commercially available. The following vectors are provided by way of example.

The vector containing the appropriate DNA sequence as herein, as well as an appropriate promoter or control sequence, can be employed to transform an appropriate host to permit the host to express the protein.

Thus, in certain aspects, the present invention relates to host cells containing the above-described constructs. The host cell can be a higher eukaryotic cell, such as a mammalian cell, or a lower eukaryotic cell, such as a yeast cell, e.g., *Saccharomyces cerevisiae*, or the host cell can be a prokaryotic cell, such as a bacterial cell.

Representative examples of appropriate hosts include bacterial cells, such as *E. coli, Streptomyces, Salmonella typhimurium*; thermophilic or mesophilic bacteria; fungal cells, such as yeast; and plant cells, etc. The selection of an appropriate host is deemed to be within the scope of those skilled in the art from the teachings herein.

Appropriate fungal hosts include yeast. In certain aspects of the invention the yeast is *Saccharomyces cerevisiae, Kluveromyces lactus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schwanniomyces occidentalis, Issatchenkia orientalis*, or *Kluveromyces marxianus*.

Yeast: Yeast vectors include those of five general classes, based on their mode of replication in yeast, YIp (yeast integrating plasmids), YRp (yeast replicating plasmids), YCp (yeast replicating plasmids with centromere (CEN) elements incorporated), YEp (yeast episomal plasmids), and YLp (yeast linear plasmids). With the exception of the YLp plasmids, all of these plasmids can be maintained in *E. coli* as well as in *Saccharomyces cerevisiae* and thus are also referred to as yeast shuttle vectors.

In certain aspects, these plasmids can contain types of selectable genes including plasmid-encoded drug-resistance genes and/or cloned yeast genes, where the drug resistant gene and/or cloned yeast gene can be used for selection. Drug-resistance genes include, e.g., ampicillin, kanamycin, tetracycline, neomycin, hygromycin, zeocin, NAT, and sulfometuron methyl. Cloned yeast genes include e.g., HIS3, LEU2, LYS2, TRP1, URA3, TRP1 and SMR1. pYAC vectors may also be utilized to clone large fragments of exogenous DNA on to artificial linear chromosomes In certain aspects of the invention, YCp plasmids, which have high frequencies of transformation and increased stability to due the incorporated centromere elements, are utilized. In certain other aspects of the invention, YEp plasmids, which provide for high levels of gene expression in yeast, are utilized. In additional aspects of the invention, YRp plasmids are utilized.

The vector can also contain one or more polynucleotides. The one or more polynucleotides can, for example, encode one or more cellulases. The one or more cellulases can be one or more endogluconases, such as endogluconase I, an exogluconase, such as cellobiohyrolase I or cellobiohydrolase II or a β-glucosidase, such as β-glucosidase I. The one or more polynucleotides can be a termite or termite-associated symbiont polynucleotide, or can be a polynucleotide from another organism, for example from *T. reesei, S. fibuligera, Neosartorya fisheri, Chaetomium thermophilum* or *T. emersonni*. In some embodiments, the one or more polynucleotides encodes a termite or termite-associated symbiont cellulase or a cellulase from another organism such as *T. reesei, S. fibuligera, Neosartorya fisheri, Chaetomium thermophilum* or *T. emersonni*.

In one embodiment of the present invention, one of the one or more polynucleotides encodes the *Schizochytrium aggregatum* Cbh1 polypeptide, or a fragment, variant or derivative thereof. The amino acid sequence of the *Schizochytrium aggregatum* Cbh1 polypeptide corresponds to SEQ ID NO: 44 as follows:

```
                                        (SEQ ID NO: 44)
MSAITLALGALALSSVVNAQQAGTLTPEKHPAFSVSTCSAGGTCTSKTQS

IVLDGNWRWLHSTSGSTNCYTGNTFDKTLCPDGVTCAANCALDGADYTGT

YGIKASGNSLSLQLKTGSNVGSRVYLMDEQDKNYQLFNLKNQEFTFDVDV

SKIGCGLNGALYFVSMPADGGLSTTNKAGTKFGTGYCDAQCPKDIKFIKG

KANSDGWTASSNNANTGFGTTGSCCNEMDIWEANGISNAVTPHSCSPGNA

ACTSDTTCGSGDGNRYKGYCDKDGCDFNPFRMGNQTFYGPGKTIDTTKPL

TVVTQFITSDNTASGDLVEIRRKYVQGGKVFDQPTSNVAGVSGNSITDTF

CKNQKSVFGDTNDFAAKGGLKAMGDAFADGMVLVMSLWDDYDVNMHWLNS

PYPTDADPTKPGVARGTCSITSGKPADVESQTPGATVVYSNIKTGPIGST

FSGAQQPGGPGSGSSSSSAGGSSTTSRSSSTTSRATTTSVGTTTTTSS

RTTTTSAAGGVVQKYGQCGGLTYTGPTTCVSGTTCTKANDYYSQCL
```

In one particular embodiment, one of the one or more polynucleotides comprises the cDNA sequence encoding *Schizochytrium aggregatum* cbh1, or a fragment, derivative or variant thereof. The cDNA sequence encoding the *Schizochytrium aggregatum* cbh1 is as follows:

```
                                        (SEQ ID NO: 45)
ATGTCTGCCATTACCCTCGCCCTGGGTGCTCTTGCCCTCAGCTCTGTTGT

CAACGCTCAGCAGGCTGGAACCCTTACTCCTGAAAAACACCCTGCTTTTT

CTGTGTCTACTTGCTCTGCCGGCGGCACTTGCACGTCCAAGACCCAGAGC

ATTGTGCTCGATGGCAACTGGCGCTGGCTCCACTCTACTTCCGGCTCCAC

CAACTGCTACACAGGTAACACCTTCGACAAGACTTTGTGCCCTGATGGAG

TGACTTGCGCCGCAAACTGCGCCCTCGATGGTGCTGACTACACCGGCACT

TACGGTATCAAGGCATCCGGCAACTCTCTGAGCCTTCAGCTCAAGACTGG

CAGCAACGTTGGCTCCAGAGTCTACCTCATGGACGAGCAGGACAAGAACT

ACCAGCTCTTCAACCTGAAGAACCAGGAGTTTACGTTCGACGTCGACGTC

AGCAAGATCGGATGTGGTCTCAACGGCGCTCTGTACTTCGTGTCCATGCC

CGCAGATGGTGGACTTTCTACCACTAACAAGGCCGGCACCAAGTTCGGAA

CAGGATATTGTGATGCTCAGTGTCCTAAAGACATCAAGTTTATCAAGGGC

AAGGCAAACAGCGATGGCTGGACAGCATCTTCCAACAACGCAAACACCGG

TTTCGGTACGACCGGCTCCTGCTGCAACGAGATGGATATCTGGGAGGCAA

ACGGGATCTCCAACGCTGTGACTCCTCACTCCTGCAGTCCCGGCAACGCC

GCTTGCACTTCTGACACAACTTGTGGCTCTGGCGACGGTAACCGCTACAA

AGGCTACTGTGACAAGGACGGTTGCGATTTCAACCCCTTCAGGATGGGCA

ACCAGACCTTCTACGGCCCCGGCAAGACTATCGACACCACCAAGCCTCTC
```

```
ACTGTGGTCACCCAATTCATTACCTCTGACAACACTGCTAGTGGCGATCT
TGTTGAGATCCGTCGCAAGTACGTCCAGGGCGGCAAGGTCTTCGATCAGC
CCACATCCAACGTTGCTGGCGTTAGCGGCAACTCGATCACCGACACCTTC
TGCAAAAACCAGAAGTCCGTCTTCGGTGACACTAACGACTTCGCTGCGAA
GGGTGGCTTGAAGGCTATGGGCGACGCCTTCGCTGATGGCATGGTCCTTG
TCATGTCTCTGTGGGATGATTACGATGTCAACATGCACTGGCTCAACTCT
CCTTACCCAACTGACGCCGACCCAACAAAGCCTGGTGTTGCCCGTGGAAC
TTGCTCTATCACCTCTGGTAAGCCCGCCGACGTCGAGAGCCAGACTCCTG
GTGCCACCGTTGTCTACTCGAACATCAAGACTGGTCCCATTGGCTCCACC
TTCTCTGGCGCCCAACAGCCCGGTGGCCCCGGCAGTGGTTCTTCATCTTC
CAGCTCAGCGGGAGGCTCAAGCACCACCTCCAGGTCTTCTTCTACCACCT
CCAGGGCTACCACCACGAGTGTCGGGACCACTACCACCACCACTAGCTCT
CGCACGACCACAACCAGCGCTGCTGGCGGCGTCGTCCAGAAGTACGGACA
GTGCGGTGGCCTGACATACACTGGTCCTACTACTTGTGTGAGCGGAACCA
CTTGCACCAAGGCCAACGACTACTACTCGCAGTGCTTG.
```

In another particular embodiment, the one or more polynucleotides comprises a codon-optimized version of the cDNA sequence encoding *Schizochytrium aggregatum* cbh1, or a fragment, derivative or variant thereof. For example, a codon-optimized cDNA sequence encoding the *Schizochytrium aggregatum* cbh1 can comprise the sequence of SEQ ID NO:46 as follows, or a fragment, variant or derivative thereof. In SEQ ID NO:46, the *Schizochytrium aggregatum* cbh1 cDNA sequence has been codon optimized for expression in *Saccharomyces cerevisiae*. The native *Schizochytrium aggregatum* cbh1 signal sequence is exchanged by replacing it with a slightly modified (one amino acid different) *Saccharomyces cerevisiae* alpha mating factor pre signal sequence (underlined). The STOP-codon is double underlined in the sequence shown below.

```
                                      (SEQ ID NO: 46)
ATGAGATTTCCATCTATTTTCACTGCTGTTTTGTTCGCAGCCTCATCGAG

TCTAGCTCAACAGGCCGGTACTCTAACGCCTGAGAAACATCCCGCCTTCT

CCGTTAGTACATGTTCCGCTGGAGGCACGTGCACTAGTAAGCACAAAGC

ATAGTCTTAGATGGCAACTGGAGATGGCTTCACAGCACATCCGGTTCAAC

GAACTGTTATACTGGCAATACATTCGACAAGACGCTTTGTCCCGATGGTG

TCACTTGTGCCGCTAATTGTGCTTTGGACGGTGCAGACTATACCGGAACG

TATGGCATAAAGGCTTCAGGAAATTCCTTATCCCTACAGCTTAAAACTGG

AAGTAATGTGGGTTCTAGAGTTTACTTGATGGACGAGCAAGATAAGAATT

ATCAATTATTCAACTTGAAGAATCAGGAGTTCACTTTTGATGTAGACGTG

TCAAAGATCGGCTGTGGTTTAAACGGCGCCTTGTACTTCGTGTCCATGCC

AGCAGACGGAGGTTTGTCCACAACTAACAAAGCTGGTACGAAGTTCGGCA

CGGGATATTGTGACGCCCAATGCCCAAAAGATATTAAGTTCATCAAGGA

AAGGCAAATTCTGATGGCTGGACAGCTTCCTCAAATAATGCCAACACAGG

ATTCGGCACAACCGGTAGTTGTTGCAATGAAATGGATATATGGGAAGCAA
```

ACGGAATTAGTAATGCTGTTACACCTCATTCATGTTCTCCTGGAAATGCC

GCATGTACGTCCGATACGACTTGCGGTAGTGGTGACGGAAACAGATACAA

AGGCTATTGCGATAAGGATGGATGCGACTTTAATCCATTCAGAATGGGAA

ATCAAACTTTCTACGGCCCCGGAAAGACGATAGATACTACGAAGCCACTA

ACGGTGGTGACACAGTTCATAACGTCAGACAATACAGCTTCTGGCGACTT

AGTTGAAATTAGAAGAAAGTATGTGCAAGGAGGTAAAGTGTTTGATCAGC

CCACCAGCAACGTAGCCGGTGTCAGTGGCAATTCAATTACAGACACTTTT

TGCAAGAACCAGAAATCTGTGTTTGGAGATACGAATGACTTCGCAGCTAA

GGGCGGATTAAAAGCAATGGGAGATGCATTTGCTGATGGTATGGTCCTAG

TAATGTCCTTATGGGACGATTACGACGTCAATATGCATTGGCTTAATTCA

CCTTATCCAACCGATGCCGACCCTACAAAGCCAGGTGTTGCTAGAGGTAC

ATGCAGTATCACTAGTGGAAAGCCCGCTGATGTGGAGAGCCAAACCCCTG

GTGCTACAGTTGTATACTCAAACATTAAGACTGGTCCAATTGGCTCTACG

TTCAGTGGAGCCCAGCAACCTGGAGGCCCCGGATCTGGTTCCTCAAGTAG

TTCATCCGCAGGCGGTTCATCCACTACGTCAAGGTCCAGTAGCACTACCT

CTAGAGCTACAACTACCAGCGTCGGAACAACCACTACGACAACCTCTAGT

AGGACGACCACTACAAGCGCCGCAGGCGGTGTAGTTCAGAAATATGGCCA

GTGTGGAGGTCTAACTTACACAGGACCAACGACTTGCGTATCTGGTACAA

CGTGCACGAAGGCTAATGATTATTACTCCCAATGTTT<u>ATAA</u>

In certain embodiments, the vector comprises a (1) a first polynucleotide, where the first polynucleotide encodes for a termite cellulase or termite-associated symbiont cellulase, or domain, fragment, variant, or derivative thereof; and (2) one or more additional polynucleotides, where the one or more additional polynucleotides encodes for a termite cellulase or termite-associated symbiont cellulase, or domain, fragment, variant, or derivative thereof.

In certain additional embodiments, the vector comprises a first polynucleotide encoding for a termite cellulase or termite-associated symbiont cellulase and one or more additional polynucleotides encoding for the *S. cerevisiae* alpha mating factor signal sequence or any other signal sequence.

In certain additional embodiments, the vector comprises a first polynucleotide encoding for a termite cellulase or termite-associated symbiont cellulase and one or more additional polynucleotides encoding for the CBM domain. In some embodiments, the CBM domain is the CBM domain of *T. reesei* cbh1 or *T. reesei* cbh2.

In further embodiments, the first and one or more additional polynucleotides are in the same orientation, or the one or more additional polynucleotides is in the reverse orientation of the first polynucleotide. In additional embodiments, the first polynucleotide is either 5' (i.e. upstream) or 3' (i.e. downstream) to the one or more additional polynucleotides. In certain other embodiments, the first polynucleotide and/or the one or more additional polynucleotides are encoded by codon-optimized polynucleotides, for example, polynucleotides codon-optimized for *S. cerevisiae*. In additional embodiments, the first polynucleotide is a codon-optimized termite cellulase or termite-associated symbiont cellulase and the one or more additional polynucleotides encodes for a codon-optimized CBM from *T. reesei* Cbh1 or Cbh2.

In particular embodiments, the vector of the present invention is a pMU451 plasmid containing a termite cellulase or termite-associated symbiont cellulase encoding sequence. A diagram of pMU451 is found in FIG. 1.

However, any other plasmid or vector may be used as long as they are can be maintained in a host cell and are useful for gene expression. Selection of the appropriate vector and promoter is well within the level of ordinary skill in the art.

Heterologous Expression of Termite Cellulases and Termite-Associated Symbiont Cellulases in Host Cells and Uses Thereof In order to address the limitations of the previous systems, the present invention provides termite cellulase or termite-associated symbiont cellulase polynucleotides and polypeptides, or domains, variants, or derivatives thereof, that can be effectively and efficiently utilized in a consolidated bioprocessing system. One aspect of the invention, is thus related to the efficient production of cellulases, especially termite and termite-associated symbiont cellulases in a host organism. The present invention therefore relates to host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector comprising a sequence encoding a termite cellulase and/or a termite-associate symbiont cellulase. In certain aspects, the present invention relates to host cells containing the above-described polynucleotide constructs. In some embodiments, the host cell comprises a polynucleotide that encodes a termite or termite-associated symbiont cellulase or a fragment, variant or derivative thereof. In some embodiments, the polynucleotide is codon-optimized for expression in a heterologous system. The host cell can be a higher eukaryotic cell, such as a mammalian cell, or a lower eukaryotic cell, such as a yeast cell, e.g., *Saccharomyces cerevisiae*. The selection of an appropriate host is deemed to be within the scope of those skilled in the art from the teachings herein.

Appropriate hosts include yeast. In certain aspects of the invention the yeast is *Saccharomyces cerevisiae, Kluveromyces lactus, Kluveromyces marxianus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus* or *Schwanniomyces occidentalis*.

Introduction of the construct into a host yeast cell, e.g., *Saccharomyces cerevisiae*, can be effected by lithium acetate transformation, spheroplast transformation, or transformation by electroporation, as described in Current Protocols in Molecular Biology, 13.7.1-13.7.10.

Introduction of the construct in other host cells can be effected by calcium phosphate transfection, DEAF-Dextran mediated transfection, or electroporation. (Davis, L., et al., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Following creation of a suitable host cell and growth of the host cell to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Yeast cells, e.g., *Saccharomyces cerevisiae*, employed in expression of proteins can be manipulated as follows. Termite cellulase or termite-associated symbiont cellulase polypeptides are generally secreted by cells and therefore can be easily recovered from supernatant using methods known to those of skill in the art. Proteins can also be recovered and purified from recombinant yeast cell cultures by methods including spheroplast preparation and lysis, cell disruption using glass beads, and cell disruption using liquid nitrogen for example.

Various mammalian cell culture systems can also be employed to express recombinant protein. Expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences.

Additional methods include ammonium sulfate or ethanol precipitation, acid extraction, anion or cation exchange chromatography, phosphocellulose chromatography, hydrophobic interaction chromatography, affinity chromatography, hydroxylapatite chromatography, gel filtration, and lectin chromatography. Protein refolding steps can be used, as necessary, in completing configuration of the mature protein. Finally, high performance liquid chromatography (HPLC) can be employed for final purification steps.

The host cells of the present invention can express cellulases in a secreted and/or a tethered form. For example, in some embodiments, the termite cellulase or termite-associated symbiont cellulase polypeptide of the present invention can be in a secreted or a tethered form. As used herein, a protein is "tethered" to an organism's cell surface if at least one terminus of the protein is bound, covalently and/or electrostatically for example, to the cell membrane or cell wall. It will be appreciated that a tethered protein may include one or more enzymatic regions that may be joined to one or more other types of regions at the nucleic acid and/or protein levels (e.g., a promoter, a terminator, an anchoring domain, a linker, a signaling region, etc.). While the one or more enzymatic regions may not be directly bound to the cell membrane or cell wall (e.g., such as when binding occurs via an anchoring domain), the protein is nonetheless considered a "tethered enzyme" according to the present specification.

Tethering can, for example, be accomplished by incorporation of an anchoring domain into a recombinant protein that is heterologously expressed by a cell, or by prenylation, fatty acyl linkage, glycosyl phosphatidyl inositol anchors or other suitable molecular anchors which may anchor the tethered protein to the cell membrane or cell wall of the host cell. A tethered protein can be tethered at its amino terminal end or optionally at its carboxy terminal end.

As used herein, "secreted" means released into the extracellular milieu, for example into the media. Although tethered proteins may have secretion signals as part of their immature amino acid sequence, they are maintained as attached to the cell surface, and do not fall within the scope of secreted proteins as used herein.

The termite cellulase or termite-associated symbiont cellulase polypeptides of the present invention may be in the form of the secreted protein, including the mature form, or may be a part of a larger protein, such as a fusion protein. It is often advantageous to include an additional amino acid sequence which contains secretory or leader sequences, prosequences, sequences which aid in purification, such as multiple histidine residues, or an additional sequence for stability during recombinant production.

Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (see for example EP 546049; WO 9324631). The secretion signal DNA or facilitator may be located between the expression-controlling DNA and the instant gene or gene fragment, and in the same reading frame with the latter.

The host cells of the present invention can express one or more termite or termite-associated symbiont cellulase polypeptides. The host cells of the present invention can also express, in addition to the termite or termite-associated symbiont cellulase, cellulases from other organisms. For example, the host cells of the present invention can express, in addition to the termite or termite-associated symbiont cellulase the *Schizochytrium aggregatum* Cbh1 protein. In some embodiments, the host cell expresses at least one endogluconase, at least one exogluconase and at least one β-glucosidase, wherein at least one of the endogluconase, exogluconase or β-glucosidase is a termite or termite-associated symbiont cellulase. In some embodiments, the host cell expresses at least two endogluconases, at least two exogluconases, or at least two β-glucosidases. In some embodiments, the host cell expresses at least one cellulase that has both endogluconase and exogluconase activity and at least one additional cellulase that has β-glucosidase activity.

The transformed host cells or cell cultures, as described above, can be examined for endoglucanase, cellobiohydrolase and/or β-glucosidase protein content. Protein content can be determined by analyzing the host (e.g., yeast) cell supernatants. In certain embodiments, the high molecular weight material is recovered from the yeast cell supernatant either by acetone precipitation or by buffering the samples with disposable de-salting cartridges. The analysis methods include the traditional Lowry method or protein assay method according to BioRad's manufacturer's protocol. Using these methods, the protein content of saccharolytic enzymes can be estimated.

The transformed host cells or cell cultures, as described above, can be further analyzed for hydrolysis of cellulose (e.g., by a sugar detection assay), for a particular type of cellulase activity (e.g., by measuring the individual endoglucanase, cellobiohydrolase or β-glucosidase activity) or for total cellulase activity. Endoglucanase activity can be determined, for example, by measuring an increase of reducing ends in an endogluconase specific CMC substrate. Cellobiohydrolase activity can be measured, for example, by using insoluble cellulosic substrates such as the amorphous substrate phosphoric acid swollen cellulose (PASC) or microcrystalline cellulose (Avicel) and determining the extent of the substrate's hydrolysis. β-glucosidase activity can be measured by a variety of assays, e.g., using cellobiose.

A total cellulase activity, which includes the activity of endoglucanase, cellobiohydrolase and β-glucosidase, will hydrolyze crystalline cellulose synergistically. Total cellulase activity can thus be measured using insoluble substrates including pure cellulosic substrates such as Whatman No. 1 filter paper, cotton linter, microcrystalline cellulose, bacterial cellulose, algal cellulose, and cellulose-containing substrates such as dyed cellulose, alpha-cellulose or pretreated lignocellulose.

One aspect of the invention is thus related to the efficient production of cellulases, especially termite and termite-associated symbiont cellulases, to aid in the digestion of cellulose and generation of ethanol. A cellulase can be any enzyme involved in cellulase digestion, metabolism and/or hydrolysis, including an endogluconase, exogluconase, or β-glucosidase.

It will be appreciated that suitable lignocellulosic material may be any feedstock that contains soluble and/or insoluble cellulose, where the insoluble cellulose may be in a crystalline or non-crystalline form. In various embodiments, the lignocellulosic biomass comprises, for example, wood, corn, corn cobs, corn stover, corn fiber, sawdust, bark, leaves, agricultural and forestry residues, grasses such as switchgrass, cord grass, rye grass or reed canary grass, miscanthus, ruminant digestion products, municipal wastes, paper mill effluent, newspaper, cardboard, miscanthus, sugar-processing residues, sugarcane bagasse, agricultural wastes, rice straw, rice hulls, barley straw, cereal straw, wheat straw, canola straw, oat straw, oat hulls, stover, soybean stover, forestry wastes, recycled wood pulp fiber, paper sludge, sawdust, hardwood, softwood or combinations thereof.

In certain embodiments of the present invention, a host cell comprising a vector which encodes and expresses a termite cellulase or termite-associated symbiont cellulase that is utilized for consolidated bioprocessing is co-cultured with additional host cells expressing one or more additional endoglucanases, cellobiohydrolases and/or β-glucosidases. In other embodiments of the invention, a host cell transformed with a termite cellulase or termite-associated symbiont cellulase is transformed with and/or expresses one or more other heterologous endoglucanases, exogluconases or β-glucosidases. The endogluconase, exogluconase and/or β-glucosidase can be any suitable endogluconase, exogluconase and β-glucosidase derived from, for example, a termite, fungal or bacterial source.

Specific activity of cellulases can also be detected by methods known to one of ordinary skill in the art, such as by the Avicel assay (described supra) that would be normalized by protein (cellulase) concentration measured for the sample. To accurately measure protein concentration a termite or termite-associated symbiont cellulase can be expressed with a tag, for example a His-tag or HA-tag and purified by standard methods using, for example, antibodies against the tag, a standard nickel resin purification technique or similar approach.

In additional embodiments, the transformed host cells or cell cultures are assayed for ethanol production. Ethanol production can be measured by techniques known to one or ordinary skill in the art e.g. by a standard HPLC refractive index method.

EXAMPLES

Materials and Methods

Media and Strain Cultivation

TOP10 cells (Invitrogen) were used for plasmid transformation and propagation. Cells were grown in LB medium (5 g/L yeast extract, 5 g/L NaCl, 10 g/L tryptone) supplemented with ampicillin (100 mg/L). Also, 15 g/L agar was added when solid media was desired.

Yeast strains were routinely grown in YPD (10 g/L yeast extract, 20 g/L peptone, 20 g/L glucose), or YNB+glucose (6.7 g/L Yeast Nitrogen Base without amino acids, and supplemented with appropriate amino acids for strain, 20 g/L glucose). 15 g/L agar was added for solid media.

Yeast strain MO375 was used as a host strain in several experiments. MO375 was derived from Y294 (MO013) in which His3 and Trp1 auxotrophies were rescued by transformation with *S. cerevisiae* His3 and Trp1 PCR products. Y294 (ATCC 201160) has the following genotype: a leu2-3,112 ura3-52 his3 trp1-289.

Molecular Methods

Standard protocols were followed for DNA manipulations (Sambrook et al. 1989). PCR was performed using Phusion polymerase (New England Biolabs) for cloning, and Taq polymerase (New England Biolabs) for screening transformants, and in some cases Advantage Polymerase (Clontech) for PCR of genes for correcting auxotrophies. Manufacturers guidelines were followed as supplied. Restriction enzymes were purchased from New England Biolabs and digests were set up according to the supplied guidelines. Ligations were performed using the Quick ligation kit (New England Biolabs) as specified by the manufacturer. Gel purification was performed using either Qiagen or Zymo research kits, PCR product and digest purifications were performed using Zymo research kits, and Qiagen midi and miniprep kits were used for purification of plasmid DNA.

Yeast Transformation

Yeast were transformed using LiOAc chemical transformation. Specifically, yeast were grown in 2 mls of YPD at 30° C. overnight. The following morning, 50 mls of YPD were inoculated with 0.5 mls of the overnight culture and then grown at 30° C. with shaking for 4-5 hours. Cells were then spun down at top speed in a clinical centrifuge for about 5 minutes. The supernatant was removed and the cells were resuspended in water and spun down again. Next, the cells were resuspended in 1 ml of 100 mM LiOAc and transferred to a microfuge tube. Cells were spun at top speed for 15 seconds and then suspended in 150 µl transformation mix (15 µl H$_2$O, 15 µl 1 M LiOAc, 20 µl DNA carrier (Ambion catalog number AM9680) and 100 µl 50% PEG 3350). Miniprep DNA (1 µl) and 150 µl of the transformation mix containing yeast cells were mixed in a microfuge tube, incubated at 30° C. for 30 minutes and then heatshocked for 15 minutes in a 42° C. water bath. After the heatshock, cells were spun down for 15 seconds, the transformation mix was removed by pipette, and 50 µl of sterile water was added. Cells were gently resuspended and plated on selective media and grown for 2-3 days at 30° C.

Alternatively, yeast were transformed by electrotransformation. A protocol for electrotransformation of yeast was developed based on Cho K M et al., "Delta-integration of endo/exo-glucanase and beta-glucosidase genes into the yeast chromosomes for direct conversion of cellulose to ethanol," *Enzyme Microb Technol* 25:23-30 (1999) and on Ausubel et al., Current protocols in molecular biology. USA: John Wiley and Sons, Inc. (1994). Yeast cells for transformation were prepared by growing to saturation in 5 mL YPD cultures. 4 mL of the culture was sampled, washed 2× with cold distilled water, and resuspended in 640 µL cold distilled water. 80 µL of 100 mM Tris-HCl, 10 mM EDTA, pH 7.5 (10×TE buffer—filter sterilized) and 80 µL of 1M lithium acetate, pH 7.5 (10× liAc—filter sterilized) were added and the cell suspension was incubated at 30° C. for 45 min. with gentle shaking. 20 µL of 1M DTT was added and incubation continued for 15 min. The cells were then centrifuged, washed once with cold distilled water, and once with electroporation buffer (1M sorbitol, 20 mM HEPES), and finally resuspended in 267 µL electroporation buffer.

For electroporation, 100 ng of plasmid DNA (pRDH105) was combined with ~100 ng of His3 PCR product and added to 50 µL of the cell suspension in a sterile 1.5 mL microcentrifuge tube. A control strain was built by using 100 ng each of the Ura3 and His 3 PCR products. The mixture was then transferred to a 0.2 cm electroporation cuvette, and a pulse of 1.4 kV (200Ω, 25 µF) was applied to the sample using the Biorad Gene Pulser device. 1 mL of cold 1M sorbitol adjusted to was placed in the cuvette and the cells were spread on Yeast nitrogen base media (Difco) with glucose, and not supplemented with amino acids.

Cellulase Assay Reagents

Avicel substrate mix was prepared by combining 0.6 g Avicel (2%), 500 µl 3 M sodium acetate pH 5.0 (50 mM), 1.2 ml 0.5% sodium azide (0.02%) and 30 µl BGL (Novozyme-188, Sigma) and adding dH$_2$0 to a total volume of 30 mls.

Carboxymethylcellulose (CMC) mix was prepared by a mixing 1.14 g CMC per 100 mL citrate buffer (50 mM pH 5.5) and autoclaving for 20-25 minutes. The CMC/citrate buffer mixture was agitated to ensure that all CMC was dissolved. 1 ml of 0.5% of sodium azide was added to the 44 mls of CMC/citrate buffer mixture to prepare 45 mls of the final CMC mix.

DNS 1% was prepared by mixing 10 g 3,5-dinitrosalicylic acid, 0.5 g sodium sulfite, 10 g sodium hydroxide and water to 1 liter. DNS was calibrated with glucose, using glucose samples with concentration of 0, 1, 2, 3, 4, 5, 6, 7, 8, 9, and 10 g/L, and the slope (S) was calculated such that S=0.1 at 565 nm.

Calculations of the percent Avicel or CMC converted after about 24 and/or 48 hours were performed using the following equation:

$$Y = \frac{(OD(T = 24 \text{ or } 48) - OD(T = 0)) \times 100\%}{S \times A} = \frac{\Delta OD \times 100}{0.1 \times 10} = \Delta OD \times 100$$

wherein Y=% of Avicel or CMC converted at 24 or 48 hrs; S=DNS/glucose calibration slope at 565 nm; and A=Avicel or CMC concentration at T=0.

Example 1

Cloning of Codon-Optimized Termite Cellulase Genes and their Expression in *Saccharomyces cerevisiae*

Cellulase genes from various termite sources (as indicated in Table 5 below) were codon-optimized for expression in the yeast *Saccharomyces cerevisiae* and *K. lactis*.

TABLE 5

Termite and Termite-Associated Cellulase Symbiont Cellulase Constructs and Strains

| Yeast strain | Expression construct | Family | Organism | NCBI ref | Activity |
|---|---|---|---|---|---|
| M0443 | pMU456 | Protozoa | *Holomastigotoides mirabile* | AB071011 | endo |
| M0444 | pMU457 | Protozoa | *Reticulitermes speratus* symbiont | AB274534 | endo |
| M0446 | pMU465 | Protozoa | *Coptotermes lacteus* symbiont | AB089801 | endo |
| M0447 | pMU466 | Protozoa | *Reticulitermes speratus* symbiont | AB045179 | endo |
| M0449 | pMU471 | Metazoa | *Coptotermes formosanus* | AB058671 | endo |
| M0450 | pMU472 | Metazoa | *Nasutitermes takasagoensis* | AB013272 | endo |
| M0451 | pMU473 | Metazoa | *Coptotermes acinaciformis* | AF336120 | endo |
| M0452 | pMU490 | Protozoa | *Cryptocercus punctulatus* symbiont | AB274702 | endo |
| M0453 | pMU491 | Protozoa | *Mastotermes darwiniensis* symbiont | AB274656 | endo |
| M0454 | pMU492 | Protozoa | *Pseudotrichonympha grassii* | AB071864 | exo |
| M0455 | pMU493 | Protozoa | *Reticulitermes flavipes* gut symbiont | DQ014511 | endo |
| M0460 | pMU499 | Metazoa | *Mastotermes darwinensis* | AJ511343 | endo |
| M0461 | pMU500 | Metazoa | *Reticulitermes speratus* | AB019095 | endo |
| M0462 | pMU501 | Protozoa | *Hodotermopsis sjoestedti* symbiont | AB274582 | endo |
| M0463 | pMU502 | Metazoa | *Reticulitermes flavipes* | AY572862 | endo |
| M0464 | pMU503 | Metazoa | *Nasutitermes walkeri* | AB013273 | endo |
| M0465 | pMU504 | Metazoa | *Panesthia cribrata* | AF220597 | endo |
| M0480 | pMU468 | Protozoa | *Neotermes koshunensis* symbiont | AB274614 | endo |

For metazoan genes, the native signal sequence was replaced with *S. cerevisiae* alpha mating factor pre signal sequence with the following amino acid sequence: MRFPSIFTAVLFAASSALA (SEQ ID NO: 43). For protozoan genes, native signal sequences could not be detected; therefore, the *S. cerevisiae* alpha mating factor pre signal sequence was attached to the 5' end of the gene. When necessary to optimize the protein sequence after signal peptidase cleavage, codons encoding several N-terminal amino acids of the cellulase were removed.

The codon optimized sequences used in the following experiments are shown in Table 3 above. The synthetic sequences were then cloned into the episomal yeast expression vector (pMU451) under control of ENO1 promoter and terminator into PacI/AscI sites (see FIG. 1), and the resulting expression constructs are listed in Table 5

These constructs were then utilized to transform *S. cerevisiae* strain MO375 host strain. The resulting yeast strains, which are listed in Table 5, were tested for cellulase activity according to the procedures described in the following examples.

Example 2

Avicel Conversion Assay

An Avicel conversion assay was used to determine the activity of *S. cerevisiae* containing termite cellulases and termite-associated symbiotic protist cellulases. In these experiments, the strains to be tested were inoculated in 600 µl of YPD in a deep 96-well plate and grown with shaking at 30° C. for three days. Then, cells were spun at maximum speed for 10 minutes. Avicel substrate mix (300 µl) was added to wells of a new deep 96-well plate, and shaking was repeated throughout addition to prevent Avicel from settling. Then 300 µl of yeast supernatant (or buffer for negative control) was added to the wells containing the Avicel substrate. The yeast supernatant and substrate were mixed by pipetting and then 100 µl was transferred to a 96-well PCR plate for a sample at T=0. The deep 96-well plate containing yeast supernatant and substrate was incubated at 35° C. with shaking at 800 rpm. The 96-well PCR plate containing the T=0 samples was spun at 2000 rpm for 2 minutes. The supernatant (50 µl) was transferred to a new 96-well PCR plate that contained 100 µl of DNS mix in each well. The PCR plate containing the supernatant and DNS mix was heated at 99° C. for five minutes and then cooled to 4° C. in a PCR machine. After cooling to 4° C., 50 µl was transferred to a micro titer plate and the absorbance at 565 nm was measured using a plate reader. Samples were removed from the deep 96-well plate containing yeast supernatant and substrate that was incubated at 35° C. with shaking at 800 rpm at approximately 24 and 48 hours and the samples were processed to determine absorbance according to the same procedures as described for the samples obtained at T=0.

Each strain was tested four times, and the % Avicel conversion was calculated. Strain MO423, containing *T. reesei* EG1 was used as a positive control. Strain MO419, which was created by transforming MO375 with empty pMU451 vector, was assayed as a negative control. As shown in FIG. 2, many of the cellulases tested demonstrated activity on Avicel.

Example 3

Carboxymethyl-Cellulose Conversion Assay

A Congo Red carboxymethyl-cellulose (CMC) assay was used to test the activity of *S. cerevisiae* containing termite cellulase or termite-associated symbiotic protist genes. In these experiments, yeast colonies were patched on yeast nitrogen base (YNB) plates with CMC. (Plates were made by mixing 0.5 g CMC, 10 g Agar, 10 g glucose and water to 450 mls, autoclaving the mixture, and then adding 50 mls YNB with amino acids.) Plates were grown for two days at 30° C. and then washed with 1 M tris pH 7.5. Colonies were then stained for 20 minutes in Congo Red (0.1% in $H_2O$) and washed several times with 1 M NaCl. The photograph of FIG. 4 was taken shortly after destaining to avoid increases in background over timer. Strain MO423, containing *T. reesei* EG1 was used as a positive control, and MO247, a strain expressing *T. emersonii* CBH1 in a vector similar to pMU451 with fur1 gene knocked-out to make the episomal plasmid stable, was used as a reference of activity of an exogluconase in the Congo Red assay.

Cellulase activity on CMC was then quantitated in several of the strains using a CMC conversion assay. In this assay, yeast strains to be tested were inoculated in 10 mls media in 50 ml tubes and grown with shaking for 3 days. Tubes were then spun at max speed for 10 minutes to obtain yeast supernatant. Assays were performed in 96-well plates, and four replicates were performed for each strain tested.

Yeast supernatant (50 μl) (or buffer for negative control), was added to wells of a deep well 96-well plate containing CMC mix (450 μl) and mixed by pipetting. A 50 μl aliquot was then removed and transferred to a well of a 90-well PCR plate containing 100 μl DNS 1%. The deep well 96-well plate was incubated at 35° C. at 800 rpm for approximately 24 hours. The PCR plate was heated to 99° C. for 5 minutes and then cooled to 4° C. in a PCR machine. The 50 μl samples in the PCR plates were transferred to a microtiter plate and the absorbance of each sample was read at 565 nm. After the deep well 96-well plates had incubated for 24 hours, samples were transferred to a plate containing DNS 1%, heated and cooled in a PCR machine and transferred to a microtiter plate for absorbance reading as described. The percentage of CMC converted was calculated for all samples. As in the Avicel assay, MO419 was used as an empty vector, negative control. The results shown in FIG. 4 demonstrate that each of the strains tested showed increased activity as compared to yeast expressing *T. reesei* EG1 (positive control).

In addition, strain MO446 was tested in the CMC assay (data not shown) and did not show any activity on CMC. MO446 expresses a protist *Coptotermes lacteus* symbiont cellulase (gene accession #AB089801) that has been annotated as an endo-beta-1,4,glucanase. However, the lack of activity on CMC, in addition to the significant activity on Avicel (demonstrated in Example 2 and FIG. 2) indicate that AB089801 may in fact be an exogluconase.

Example 4

Yeast-Made Termite Endoglucanase Significantly Increases Avicel Conversion by Yeast-Made Fungal CBHs To determine if the addition of termite endoglucanase to fungal CBHs has a positive effect on Avicel conversion, an Avicel assay was performed with a yeast-made fungal CBH mix (*Talaromyces emersonii* CBH1+CBD (*T. reesei* CBH1) and *Chrysosporium lucknowense* CBH2b), as well as the fungal CBH mix combined with yeast-made *Coptotermes formosanus* endoglucanase (CfEG) (FIG. 4).

Table 6 below describes the samples that were used in this experiment:

TABLE 1

Enzymes used in experiment with termite EG added to fungal CBHs

| Enzyme | Production strain | Expression vector | Sample preparation | Protein mg/l |
|---|---|---|---|---|
| *Talaromyces emersonii* CBH1 + *T. reesei* CBH1 CBD (TeCBH1 + CBD) | M0759 | pMU624 (2u) | 1 l fermenter | 290 |
| *Chrysosporium lucknowense* CBH2b (ClCBH2b) | M0969 | pMU784 (2u) | 1 l fermenter | 800 |
| *Coptotermes formosanus* endoglucanase (CfEG) | M0968 | pMU471 (2u) pMU663 (delta) | 100 ml shake flask | 90 |
| Negative control | M0509 | none | 1 l fermenter | n/a |

All strains used are derivatives from the industrial *S. cerevisiae* strain MO509. TrCBH1+CBD and ClCBH2b are expressed from episomal 2μ vectors (pMU624 and pMU784) with a pMU451 backbone that has been described above. In the CfEG-producing M0968 strain, endoglucanase (EG) was first introduced on the 2μ vector pMU471 (pMU451 backbone). Later, the CfEG copy number was increased by transformation with the delta integration expression vector pMU663 (pMU562 backbone). In all expression vectors, the coding gene was inserted into PacI/AscI sites of the pMU451 or pMU562 backbones between the ENO1 promoter and terminator. Strains M0759, M0969 and M0509 were grown in 1 liter (L) fermenters in YPD-based media plus 50 g/L glucose with 24 hrs batch cultivation followed by a stepped feed of 50% glucose with vitamins and trace elements for another 24 hrs. M0968 was grown in 100 milliliters (ml) YPD in a 500 ml shake flask for 3 days. Supernatants of the strains were used in the assay as an enzyme source. Protein concentration was measured by HPLC. To make the CBH mix for the Avicel assay, CBH1 and CBH2 samples were mixed in a 4:1 ratio. For the negative control (Neg Cont) 300 μl of the M0509 strain supernatant was used in the assay. In the "CBH" sample, 200 μl of the M0509 supernatant was added to 100 μl of the CBH mix. In the "CBH+EG" sample, 200 μl of the M0968 supernatant was added to 100 μl of the CBH mix.

FIG. 5 shows that the addition of yeast-made CfEG significantly increased Avicel conversion by yeast-made fungal CBHs. Yeast-made endoglucanase may be synergistically acting with yeast-made fungal CBHs. The CfEG sample alone will be tested to quantitatively evaluate and confirm this synergistic effect. The results discussed above indicate that the cellulytic properties of yeast-expressing fungal CBHs can be significantly improved by integration of a termite CfEG.

Example 5

Ethanol Production from Avicel by Co-Culture of Cellulytic Yeast Strains Including Strain Producing Termite Endoglucanase (CfEG)

To evaluate the improved performance of yeast strains each expressing a different cellulase (TeCBH1+CBD, ClCBH2b, CfEG, and *Saccharomycopsis fibuligera* BGL1 (SfBGL)), ethanol production from 10% Avicel was measured in a SSF shake flask.

Each of the strains referred to above has a MO013 background (the Y294 yeast strain: genotype: α leu2-3,112 ura3-52 his3 trp1-289; ATCC No. 201160) with cellulases expressed on an episomal 2μ plasmid (pMU451 backbone with coding gene inserted into PacI/AscI sites). The Fur1 gene was knocked out in these strains to stabilize the plasmid. Four strains each expressing one cellulase (M0595—TeCBH1+CBD; M0563—ClCBH2; M0592—CfEG; M0566—SfBGL1) were pre-grown separately in YPD in shake flasks for 3 days, mixed in equal proportion, and transferred (10% inoculation volume) into several nitrogen purged pressure bottles with YP+10% of Avicel and different concentrations of external cellulases (Zoomerase, Novozyme). The total volume was 30 ml. The bottles were incubated at 35° C. with shaking for 160 hrs and the samples were taken during this time for ethanol concentration measurement (by HPLC). The experiment was also performed with the control non-cellulytic MO249 strain (FIG. 6). FIG. 6 clearly demonstrates that co-culture of cellulytic yeast strains performs significantly better compared to the parental non-cellulytic strain at all concentrations of external enzymes used due to the efficient contribution of endogenously produced cellulases.

The above-described results demonstrate that the four cellulases (TeCBH1+CBD, ClCBH2b, CfEG, and *Saccharomy-* copsis fibuligera BGL1 (SfBGL)) can be functionally expressed in yeast. In combination, these four cellulases provide a significant level of cellulase activity. In fact, a two-fold less amount of enzyme is required (as compared to the empty control strain) when a co-culture of cells expressing these four cellulases is utilized, to achieve the same amount of ethanol production. Thus, the co-culturing of these particular cellulase expressing cells, including the expression of termite EG, significantly improves ethanol production from Avicel.

In order to make the contribution of yeast-made enzymes even more quantitative, a theoretical ethanol yield at 160 hrs of SSF was plotted against external cellulase loads (FIG. 7). FIG. 7 demonstrates that co-cultured cellulytic yeast strains save more than 50% of external enzymes. This demonstrates the feasibility of a yeast-based CBP concept.

Example 6

Quantitative Analysis of Termite Endoglucanase and Other Cellulases Produced by Yeast During Fermentation To investigate the ability of yeast to produce and accumulate cellulases during high cell density fermentation, the strain M0712 expressing four cellulases (SfBGL, CfEG, ClCBH2b, and TeCBH1+CBD) was cultivated in a 3 L bioreactor.

The M0712 strain is a derivative of the robust M0509 where all four cellulases are expressed from delta integration constructs with the zeocin marker (coding cellulase genes inserted into PacI/AscI sites of pMU562 backbone). YPD-based rich media with additional vitamins, trace elements, and 6.7 g/L of yeast nitrogen base was used for batch culture with 50 g/L glucose. After cultivation in batch phase for 24 hours, a stepped feed of 50% glucose with vitamins and trace elements was carried out for another 36 hours. At several time points, reactor samples were taken and the dry cell weight was measured. Additionally, protein concentration for each cellulase was measured by HPLC (FIG. 8). A cell density of ~90 g/L DCW was achieved in the run, as well as a total cellulase concentration of ~1.4 g/L (not including SfBGLI expression).

FIG. 8 demonstrates that yeast were able to accumulate termite endoglucanase to about 900 mg/l or 10 mg/g cells. This data means that yeast were able to produce CfEG up to 2% of TCP (total cell protein) which is a significant level of heterologous protein production in S. cerevisiae.

Example 7

Synergy Between EGs and CBH1

An Avicel assay was performed (as described in Example 4) using T. emersonii CBH1 (with no CBD) mixed with different termite endoglucanases (EGs) as well as with T. reesei EG1. The yeast strains utilized in this experiment were created by expressing the cellulases from the pMU451 vector (described above) in an M0375 background strain. All yeast strains were grown in 10 ml YPD in 50 ml conical tubes for 3 days at 30° C. and 250 rpm. The Avicel assay was performed using supernatants from the different strains, both singly and combined. For single strains, 300 µl of supernatant was used; for the combined samples, 150 µl of each strain was mixed together for the assay (See FIG. 9).

FIG. 9 demonstrates that combination of Coptotermes formosanus EG (CfEG) with T. emersonii CBH1 (TeCBH1) provides the highest Avicel conversion. Moreover, there is synergy between TeCBH1 and CfEG, with the degree of synergy about 2 at both the 24 and 48 hour time points. The degree of synergy was calculated as the synergistic activity on Avicel of the TeCBH1/CfEG mix divided by the sum of activities of the individual components (after the negative control value was deducted). In the combination experiments, the two-fold dilution of the single enzyme samples was also factored into the calculations.

These examples illustrate possible embodiments of the present invention. While the invention has been particularly shown and described with reference to some embodiments thereof, it will be understood by those skilled in the art that they have been presented by way of example only, and not limitation, and various changes in form and details can be made therein without departing from the spirit and scope of the invention. Thus, the breadth and scope of the present invention should not be limited by any of the above-described exemplary embodiments, but should be defined only in accordance with the following claims and their equivalents.

All documents cited herein, including journal articles or abstracts, published or corresponding U.S. or foreign patent applications, issued or foreign patents, or any other documents, are each entirely incorporated by reference herein, including all data, tables, figures, and text presented in the cited documents.

What is claimed is:

1. An isolated polynucleotide comprising a nucleic acid which encodes the mature endoglucanase of SEQ ID NO:36, wherein said nucleic acid is codon-optimized for expression in a yeast strain wherein at least one nucleotide within a sequence of 4, 5, 6, 7, 8, 9, or 10 consecutive A, T, C or G nucleotides is replaced with a different nucleotide, wherein the nucleotide replacement does not alter the amino acid sequence encoded by the polynucleotide and wherein the nucleotide replacement creates a codon that is the second most frequently used codon to encode an amino acid in the yeast strain.

2. The polynucleotide of claim 1, wherein the yeast is selected from the group consisting of Saccharomyces cerevisiae, Kluveromyces lactus, Kluyveromyces marxianus, Schizzosaccharomyces pombe, Candida albicans, Pichia pastoris, Pichia stipitis, Yarrowia lipolytica, Hansenula polymorpha, Phaffia rhodozyma, Candida utilis, Arxula adeninivorans, Debaryomyces hansenii, Debaryomyces polymorphus, Schizosaccharomyces pombe and Schwanniomyces occidentalis.

3. An isolated polynucleotide comprising a nucleic acid which encodes the mature endoglucanase of SEQ ID NO:36, wherein said nucleic acid is codon-optimized for expression in a s east strain, wherein at least one restriction enzyme site within the polynucleotide is removed by replacing at least one nucleotide within the restriction enzyme site with a different nucleotide, wherein the nucleotide replacement does not alter the amino acid sequence encoded by the polynucleotide and wherein the nucleotide replacement creates a codon that is the second most frequently used codon to encode an amino acid in the yeast strain.

4. An isolated polynucleotide comprising a nucleic acid which encodes the mature endoglucanase of SEQ ID NO:36, wherein said nucleic acid is codon-optimized for expression in a yeast strain, wherein one or more direct repeats, inverted repeats and mirror repeats with lengths of 10 bases or longer within said polynucleotide is altered by replacing at least one nucleotide within the repeat with a different nucleotide, wherein the nucleotide replacement does not alter the amino acid sequence encoded by the polynucleotide and wherein the nucleotide replacement creates a codon that is the second most frequently used codon to encode an amino acid in the yeast strain.

5. The polynucleotide of claim 1, wherein said polynucleotide is operably associated with a heterologous nucleic acid.

6. An isolated polynucleotide comprising a nucleic acid, wherein the nucleic acid comprises the a nucleic acid coding sequence of SEQ ID NO:16.

7. A vector comprising a first polynucleotide, wherein said first polynucleotide is the polynucleotide of claim 1.

8. A host cell comprising a polynucleotide encoding the mature endoglucanase of SEQ ID NO:36 wherein the host cell is a yeast cell, wherein the polynucleotide is codon-optimized for expression in yeast and wherein the endoglucanase is expressed, wherein the host cell is co-cultured with one or more additional host cells, wherein each of the one or more additional host cells expresses one or more endoglucanases, cellobiohydrolases and/or β-glucosidases.

9. A host cell comprising the polynucleotide of claim 1.

10. The host cell of claim 8, wherein the host cell in the co-culture has the ability to saccharify crystalline cellulose.

11. A host cell comprising a polynucleotide encoding the mature endoglucanase of SEQ ID NO: 6, wherein the host cell is a yeast cell, wherein the polynucleotide is codon-optimized for expression in yeast and wherein the endoglucanase is expressed, and wherein the host cell further comprises a polynucleotide encoding a cellulase.

12. The host cell of claim 1, wherein the cellulose is a cellobiohydrolase, a β-glucosidase, or a combination thereof.

13. The host cell of claim 12, wherein the cellulase is a *T. emersonii* cellobiohydrolase I.

14. The host cell of claim 8, wherein polynucleotide encoding the endoglucanase comprises the sequence of SEQ ID NO:16.

15. A host cell comprising the polynucleotide of claim 6.

16. The polynucleotide of claim 3, wherein said polynucleotide is operably associated with a heterologous nucleic acid.

17. A vector comprising a first polynucleotide, wherein said first polynucleotide is the polynucleotide of claim 3.

18. A host cell comprising the polynucleotide of claim 3.

19. The host cell of claim 11, wherein the host cell has the ability to saccharify crystalline cellulose.

20. The host cell of claim 11, wherein polynucleotide encoding the endoglucanase comprises the coding sequence of SEQ ID NO:16.

\* \* \* \* \*

```
                       SEQUENCE LISTING

<160> NUMBER OF SEQ ID NOS: 46

<210> SEQ ID NO 1
<211> LENGTH: 1022
<212> TYPE: DNA
<213> ORGANISM: Artificial
<220> FEATURE:
<223> OTHER INFORMATION: Synthetic Holomastigotoides mirabile
      oligonucleotide

<400> SEQUENCE: 1
ttaattaaaa  tgagatttcc  atctattttc  actgctgttt  tgttcgcagc  ctcaagtgct      60
ttagcagaga  aacatcctaa  gttcgtatgg  caacagtgta  caaagggtgg  atgctccgac     120
gtgtctggtt  atttggtgca  cgacagacat  ataggggacg  tttgggacag  agagaatacc     180
gattacccag  aattagatta  cgacgccaac  gtaggtgtca  ctgtgtcagc  agacggaaag     240
```

| | | |
|---|---|---|
| actttatcac aaagattagt ttccaaattg tgggacgata agaaagcagt aggatctaga | 300 | |
| gtgtacatag tggacaccac tgacaagaaa tatcagttat ttcaatttgt tggtaaggag | 360 | |
| tttacataca ctgtggacat gtcacaaatt ccttgcggtg tcaacgccgc tttgtacact | 420 | |
| gtcgaaatgc cagcagaggg aaaatctcct ggtggtgtag aatacggtta tggttactgc | 480 | |
| gacgcaaact gtgtggacgg tggatgttgc atggagttcg atatccaaga agcctcctct | 540 | |
| aaggcaatag tgtacacaac tcactcatgt caatctcaga ccggaggttg cgacacaagt | 600 | |
| ggttgtggtt acaacccata tagagattca aatgaccacg ccttttgggg tcaaactatt | 660 | |
| aatgtcaacc aacctgtgac tatagtgaca cagttcgttg gatcaggtgg ttctttaact | 720 | |
| gaagtcaaga gattgtacgt ccaaggaggt aaagtgaccc cagcagccaa aagtttatcc | 780 | |
| gattcatatt gcaatgttaa cgactatcgt tctttgaaaa caataggagc ttcattccaa | 840 | |
| agaggacatg tagtcgtgtt ctcattatgg gacagtgatg gaatgtcctg gatggatggt | 900 | |
| ggaaacgccg gtccttgtac gagttacaac gttgcaaccg ttgaatcatc tcagccaaat | 960 | |
| ttgaaagtaa catggtccaa cgtcaagttt ggtgatatcg acagtactta ctaaggcgcg | 1020 | |
| cc | 1022 | |

<210> SEQ ID NO 2
<211> LENGTH: 986
<212> TYPE: DNA
<213> ORGANISM: Artificial
<220> FEATURE:
<223> OTHER INFORMATION: Synthetic Coptotermes lacteus symbiont
      oligonucleotide

<400> SEQUENCE: 2

| | | |
|---|---|---|
| ttaattaaaa tgagatttcc ttccatattc accgctgttt tgttcgcagc ctcaagtgct | 60 | |
| ttagcagaat gtactaaggg tggatgtact aacaagaatg gatacatagt tcatgataag | 120 | |
| cacgtcggtg acatccagaa tagagacact ttggaccctc cagacttaga ttatgaaaag | 180 | |
| gacgtgggag taaccgtgtc cggtggaacc cttagtcaaa gattagtctc aacttggaac | 240 | |
| ggtaagaaag tcgtgggaag tagattgtat attgtggacg aagccgacga gaaatatcaa | 300 | |
| ttattcacat ttgtcggtaa ggagttcacc tataccgttg atatgtccca gatccaatgt | 360 | |
| ggaatcaatg ccgcattata cacagtggaa atgcctgccg ctggaaagac ccctggaggt | 420 | |
| gttaagtatg gatatggata ttgtgatgcc aactgcgtgg atggagattg ttgtatggag | 480 | |
| ttcgatatcc aagaagcttc taacaaggca atcgtttaca ccacccattc ctgtcaaagt | 540 | |
| caaacttcag gttgcgatac ctcaggatgc ggttacaacc cttacagaga cagtggtgac | 600 | |
| aaggcattct gggaacaac tataaacgta accagcctg tgacaattgt aacacagttt | 660 | |
| atcggttctg gtagttcctt aactgaagtc aaaagattgt gcgtgcaagg tggaaagacc | 720 | |
| ttccctccag ccaaatcatt aaccgacagt tattgtaatg ccaacgacta tagaagtttg | 780 | |
| agaactatgg gtgcatccat ggctagagga cacgttgttg tgttttcttt gtgggattct | 840 | |
| aatggtatga gttggatgga tggaggtaac gccggtcctt gtacctcata taatattgaa | 900 | |
| tctttggaat ccagtcagcc aaacttaaag gtcacatggt caaacgtgaa atacggagag | 960 | |
| atcgattctc cttattaagg cgcgcc | 986 | |

<210> SEQ ID NO 3
<211> LENGTH: 1151
<212> TYPE: DNA
<213> ORGANISM: Artificial
<220> FEATURE:

<223> OTHER INFORMATION: Synthetic Cryptocercus punctulatus symbiont
oligonucleotide

<400> SEQUENCE: 3

```
ttaattaaaa tgagatttcc atctattttc actgctgtgt tgtttgccgc ttcaagtgct      60
ttagcatcta gaatatccgt gtcatggttg agtacatccg gttccaaaat aaccgatgga     120
ggtcaaactg tcagattaac aggagtgaat tggtttggtt atgaaacctc agaggaagtg     180
tttcacggtt tgtgggccgc tggtttgcac gacttggtac agggtgtctc ccaaaagaaa     240
ttcaacactt ttagagtgcc tatttccgca tctgttttgc aagactggaa ggccggaaag     300
ccaaacccaa aaccaaacat caatttgaac gtgaatgctg acttagaggg tttgaacaat     360
caacaaatat tcgacttatt cttagccgac tgtaagaagt acaaaatcta cgtgttcatc     420
gacgtgcatg gtgttacaga tggatcatat atggacaact tatggtacac ctctgctcac     480
cctgccgaat ggatatacag tgcattggag tggttcgccg atcactacaa gggagatcag     540
actattatag gtattgacat aaagaacgag ccacacggta gatgcgaaca agccgaagca     600
gctaagtggt ccgatagtaa agacaataat aactggaagt acttcattga cagccgcca     660
gctagaatct taggtaagaa tcctaacttg ttaatattgg ttgaaggaat tgagtgttac     720
aacaacaact ggggttggtg gggtggaaac ttaatcccag ttaatgacta tcctataaac     780
ttgggttctg gacagaagca attagtctat tccccacacg aatacggtcc ttctgtgaat     840
gatcagtcat ggttcaaatc tggtttcaat tatgattcct tgtacgccga tcattggcaa     900
aagatgtgga tgttcattat cgaaaagaac atcgcccta tattgatcgg agagtggggt     960
ggtcacgttg tagaacctaa tactacctgg atgaaggctt tggtccaatt aatatccaaa    1020
tatggattgt cacaaacttt ctggtgctta aaccctgata gtggtgacac tggaggtttg    1080
ttagaaaacg attggataac ttgggataca gccaaattgg atataattaa aggtgtgtta    1140
taaggcgcgc c                                                         1151
```

<210> SEQ ID NO 4
<211> LENGTH: 1163
<212> TYPE: DNA
<213> ORGANISM: Artificial
<220> FEATURE:
<223> OTHER INFORMATION: Synthetic Mastotermes darwiniensis symbiont
oligonucleotide

<400> SEQUENCE: 4

```
ttaattaaaa tgagatttcc atctattttc actgctgttt tgttcgcagc ctcaagtgct      60
ttagcagcct attacatctc cgcttctggt aatgagttgg tggacccaac cggaaaacaa     120
ttaagaatca ccggtataaa ctggtttgga ttcgagactt cacagtctgc ttttcacggt     180
ttgtggaacg ccaacttaca caaggtcgtg caacaggttg cggagcacgg ttttaattgc     240
ttcagatgtc caatctcctg tgacttgatc cacaaatgga tgagaggaga taagacacca     300
ttacagtgga ttaacactga gccagacgca aatcctgata tgaaaggtat ctcttcaaga     360
ggaatatggg atatgtttat ggccgactgc aagaaagccg gtattaaggt gtttatcgat     420
attcatggta tccaaccaga ttcttataca ttgcctttat ggggagatac agaatacttg     480
atttccgcct tagagtggtt cgcaaacgag ttcaagaatg acgatacttt cattgccatc     540
gacgtcaaga acgaaccaca tcagcaaggt cagggatgcg gtactggtgc aaatgacgcc     600
gtgtgggaat cttcaacacg ttctaacaat tggccttatg ttgcgggatt ggcgggtaaa     660
agaatattag ctaagaatcc aggattatta atcttggtcg aaggaaatca atgctacaaa     720
```

```
ggtgatagtt cctggtgggg aggtaactta gctggtgtca agatatccc tgtggacgtt      780 ggaaacccaa agaagttagt gtattcccct cacgaatacg gtccttctgt gaatgatcaa     840
gcctggttcc atccaactat taactatgac cagttgtatt cccagcattg cacaaacat     900 tggttgtata tccacgaaga gggtattgct ccattattga taggagaatg gggtggaaag    960
ttatccggga ccaatacaca gtggatgaag ttattcgtta acttaatcgc acagtacggt   1020
ttaagtcaca ctttctggtg cttgaaccca aactccggag ataccggtgg attgttaaag   1080
gataattgga aagactggga tgaggagaaa tatgctttca ttaagccttg tttgggtggt   1140
tccttgttta agtaaggcgc gcc                                           1163

<210> SEQ ID NO 5
<211> LENGTH: 959
<212> TYPE: DNA
<213> ORGANISM: Artificial
<220> FEATURE:
<223> OTHER INFORMATION: Synthetic Neotermes koshunensis symbiont
      oligonucleotide

<400> SEQUENCE: 5
ttaattaaaa tgagatttcc atctattttc actgctgttt tgttcgcagc ctcaagtgct     60
ttagcagccg atcctgactt ggtaagatta catgtcgatg gtaatagaat cgtgatggga    120
aaaccaggtt tggcttcctc taaaacagct atgttgagag gagtgtcatg tagttggcac    180
aactggtggc ctcaatttca ttccgccgct acagttagag gtttgaaatc tgactttcac    240
gcaaatgtcg tgagaacttt cataggtgtt gaaaaggagg gaggtttctt aacaaaccag    300
caaaaggctt atgattgctg ttacgccgta gtcgatgaat gcatcgcaca aggaatatac    360
gttattataa actgggcttc attcgttttg acctaccaaa ctcaagctac ccagttcttc    420
aagaccgttg caaccaaata tcatagttct tcttacgtca tatacgagtt attgaacgaa    480
ccagaagctc cgacatgggc acaaattaaa cctatagtc aagctttaat tcaaacaatc    540
agagctattg acccatctaa tttgatatta gtcccaaccc ctagatggga tcaagagatt    600
ggtgcagctg caaacgaccc tatcacagga gataacaatt tggcttatac tttacacata    660
tacaccggaa cacacccagc tagttataga gatgacgcca gagcagctaa gaagaaaatc    720
ccagtgtggg ccgacgaaaa cggtgcaatg aacgctgatg gaaaaggagc cttgatagaa    780
actggttgga ataccctggat cgccttttac gaagagttac agataccttg gttgggatat    840
ggtacacaag atacttccga aacctgttca atttcaaat ctacagattc ctttaatgac    900
ttgtccgatt ggggaaagtt attgaaggaa accataagaa aataccaata aggcgcgcc    959

<210> SEQ ID NO 6
<211> LENGTH: 938
<212> TYPE: DNA
<213> ORGANISM: Artificial
<220> FEATURE:
<223> OTHER INFORMATION: Synthetic Hodotermopsis sjoestedti symbiont
      oligonucleotide

<400> SEQUENCE: 6
ttaattaaaa tgagattccc ttccattttc actgctgttt tgttcgcagc ctcaagtgct     60
ttagcagccc ctccatttgg aagattatgc gttgaaggaa acaaaatcgt cggtaacaag    120
agagctcctg gagtgttaag aggtgttggt ttgtcctggc ataattggtg gcctcagttt    180
tacaacgctg caaccatcaa tcacttaaag aacgactttc atgccaatgt cattagagct    240
gctataggag tggagaaaga gaatggttac tttgacaatc agcaaaacgc ctatgatttg    300
```

```
ttatacgcag ctgtggacgc agccttgtcc gctggaatat atgttatcgt ggattggcag    360
gccttccaaa tccacgaatc agatgcaaaa caattcttta ctacagttgt gaataagtac    420
aaaggtaaga gtaacgttat ctatgagata tttaatgaac ctgaatccgc tggttggtct    480
gaaatcaaga agtattcaat ttccttaatt cagacaatca gagcaattga ttccaacgca    540
ttcatattgg ttccaacccc taattgggat cagtatgttg aacaggctgc agccgaccct    600
attagtgagt acagtaatat cgcctataca attcacatat atgccgcaac acatccttta    660
tcttatttgg ataacgctag aactgccttg aaaactatcg ccttatttgg gaccgagata    720
ggtgcaatgg aggcatccgg tgatgggca atagaccaat ccaagtacca acagtggatc    780
gatttctatg agcagaatgg aatctcatac ttatgctggg ctgtacagtc taaagaagag    840
actgacagta tattgaaacc aagtgaagat tggaatgatt tgacagcatg gggaaaattg    900
tgtaagtcaa caattactgc acaccagtaa ggcgcgcc                            938

<210> SEQ ID NO 7
<211> LENGTH: 830
<212> TYPE: DNA
<213> ORGANISM: Artificial
<220> FEATURE:
<223> OTHER INFORMATION: Synthetic Reticulitermes speratus symbiont
      oligonucleotide

<400> SEQUENCE: 7
ttaattaaaa tgagatttcc atctattttc actgctgttt tgttcgcagc ctcaagtgct     60
ttagcagcct tggtacatat ggaattagag aataactcca ctagattgag agtgaaggga    120
aataagatcg tggtcggaaa ctctgataaa ggtttgagat taagaggagt gaatttgtcc    180
tggaacaact ggtggcacca attctacaac gctgacaccg ttagacactt aaagaacgac    240
tttcacgtca atgtgataag agcagccatt ggtgtggaac aggatggtgg atgggaatca    300
aacaagcaaa gaagttacga tgacttgtac gctgttatcg acgcatgtat cgctaataac    360
gtctatgtga ttgtcgattg gcagactttc tctatcaagt tgtcagaagc cacagagttc    420
ttcaccaacg ttgcaaacaa ataccatagt tcttcctata tcatctacga cttgttgaac    480
gagcctgatt catctgtgcc aagttggtcc gcaatcaagt cctatgccga atctttgata    540
aagaccatta gagctataga ttcctccaac ttaataattg tgccaactcc aaattgggat    600
cagtacgtga agcaggctgc cgcagatcct attacatctg acagtaactt aatctactca    660
atacacatat acgtcggtac tcaccctatg agttatatgg acgatgctag agaagcctta    720
aagacaatcc ctttaatcgg aggtgaaata ggtgcaatga atgctgatgg tgacggagct    780
ttggatgttt ccaaattcaa ccaatggata gacttcttat aaggcgcgcc               830

<210> SEQ ID NO 8
<211> LENGTH: 695
<212> TYPE: DNA
<213> ORGANISM: Artificial
<220> FEATURE:
<223> OTHER INFORMATION: Synthetic Reticuli termes speratus symbiont
      oligonucleotide

<400> SEQUENCE: 8
ttaattaaaa tgagatttcc atctattttc acagcagttt tgttcgcagc ctcaagtgct     60
ttggccggtg attccggaag aacaaccaga tattgggact gttgcaaagc tcttgtgct    120 tgggaaaaga aagcagccgt aactcaacct gttgacacgt gcggtaagga cggaaccact    180
agattggcta gtaatgatac cgtgaaaagt tcctgtgacg gaggtgatgg atacatgtgt    240
```

```
tatgatcagg caccatgggc tgttaacgat tctgtagcct acggtttcgc cgcagctgca      300
tgttgtggtg gagaaaccgg tgcttgctgt aattgctatg agttgacatt cacatcaggt      360
ccagtgaatg gaaaaaaaat ggtggtccag gtgactaata ccggaggtga tttgggaagt      420
aaccagttcg acttagccat cccaggaggt ggtgtcggaa tatacaatgg ttgtacacaa      480
caatcaggtg ccctgctga cggttgggga tcaagatacg gaggtgtcag ttctagaagt      540
gagtgttccc agttgccatc aggtttacaa gccggatgcc agtggagatt cgactggttc      600
caaaacgcag acaatccttc aattaatttc aaccaagtca cttgtccaag tgaattgatt      660
gcaagaacca actgcaagag aacataaggc gcgcc                                 695
```

<210> SEQ ID NO 9
<211> LENGTH: 1430
<212> TYPE: DNA
<213> ORGANISM: Artificial
<220> FEATURE:
<223> OTHER INFORMATION: Synthetic Pseudotrichonympha grassii
      oligonucleotide

<400> SEQUENCE: 9

```
ttaattaaaa tgagattccc ttctatattc actgctgttt tgtttgcagc cagttctgcc       60
ttagcacagg ctgagaatca cccatccttg tcttggcaaa attgtagatc cggtggatca      120
tgcacccaaa cctccggttc agttgtcttg gattccaaca tgagatttcc ttctatcttt      180
actgctgtct tattcgccgc ttcatcagct ttagcatgga gatggacaca cgattccagt      240
ttaactaatt gttatgatgg aaatgagtgg agttcctcat tatgccctga ccctaaaact      300
tgttctgata actgtttaat cgacggtgcc gattactctg gaacctatgg aattacttcc      360
tctggaaact ccttgaagtt ggtgttcgtc actaacggac cttactctac taacataggt      420
tcaagagtgt acttgttaaa agacgaatct cactaccaaa tatttgactt aaagaacaaa      480
gagtttacat tcactgttga tgattctaat ttggactgcg gattaaacgg agccttgtac      540
tttgtgagta tggatgagga cggtggaact tcaagattct cttccaataa ggcaggagcc      600
aaatacggta ctggatattg tgacgcccaa tgcccacacg atattaagtt cattaacggt      660
gaagcaaacg ttgaaaactg gaaacctcaa accaatgacg aaaatgctgg taacggtaga      720
tacggagcct gctgtacaga gatggatata tgggaggcaa ataagtatgc tactgcctat      780 accctcaca tctgtacagt caacggagaa tatagatgtg atggtagtga atgtggtgac      840
actgattccg gaaatagata tggaggagtg tgcgataagg acggatgcga tttcaactct      900
tatagaatgg gtaacacttc attttggggt ccaggattga tcattgacac aggtaagcca      960
gttactgttg taacccagtt cgtaaccaaa gatggaactg acaacggtca attgtcagag     1020
ataagaagaa agtacgtcca gggaggtaag gttattgaga atacagtagt caacatcgcg     1080
ggtatgtcca gtggtaatag tattacagac gacttttgca acgagcagaa atcagcattc     1140
ggagacacta acgattttga aaagaagggt ggattatccg gtttgggaaa agccttcgat     1200
tatggtatgg tgttagtttt gtctttatgg gatgatcatc aagttaatat gttatggtta     1260
gattccatat accctaccga ccagcctgca tcccagccag gtgtaaagag aggaccatgt     1320
gctacttcat ctggtgcccc aagtgatgtc gaatcacaac accctgacag ttccgtgacc     1380
tttagtgata tcagatttgg tccaatagat tcaacatatt aaggcgcgcc                1430
```

<210> SEQ ID NO 10
<211> LENGTH: 1022
<212> TYPE: DNA
<213> ORGANISM: Artificial
<220> FEATURE:
<223> OTHER INFORMATION: Synthetic Reticulitermes flavipes gut symbiont
      oligonucleotide

<400> SEQUENCE: 10

```
ttaattaaaa tgagattccc ttccattttc actgccgtct tatttgcagc ctcatcagca    60
ttagccgaga acatcctgc ctttcaatgg aagaaagatg gtgtcactca aaatggattc   120
ttggttcatg acagacatgt gggtgataac tggtatagag atcagaaaga tggaaaatcc   180
ggtgctttag acttagacta cgagaatgat gttggtgtta ctgtgtccgg tggtacttta   240
acccagagat tggtgtcaaa ctatagttgg aataacaaga ccgttgtagg gtccagatta   300
tacatcatga ccgccgacga aaagaagtat gagaaattta cttaactgg taaggagttt   360
accttcaccg tcaatttggc ccaaatacca tgtggtgtga acgctgcatt atacacagtg   420
gaaatgcctg ctgacggaat tgacgccact gaccaaaccc agggtgcacc atacggttac   480
ggatattgcg atgcaaactg tgttgatgga ggttgttgtc ctgagtttga tggtattgaa   540
gccacgagta aagcattagt attcactacc cacacgtgct caggtactgg aagtggtaga   600
ggaggttaca ccggttgtga tacatccgga tgtggttaca acccttatcg tgacgacaac   660
aaccattctt tctggaccag ttcagtgaac ttagctcaac ctgtgactat agtgacacag   720
ttccaaacta tggtgatgt taccagaaaa tatattcaaa atggaaaccc aatcgacggt   780
ggaaccttaa accagagtag atgttccgga aagcaaaaca tgacttctac cttctctaga   840
ggtcatgtcg tggttttcag tttgtgggat tccgacggaa tgtcatggtt agatggtggt   900
aatgctggac cttgtacttc ttacaatatt aaagatgtgg aaacaagaac cccaaacttg   960
actgtaacct ggtccgatgt gaaattcgga aacattggat caacaactaa ttaaggcgcg  1020
cc                                                                  1022
```

<210> SEQ ID NO 11
<211> LENGTH: 932
<212> TYPE: DNA
<213> ORGANISM: Artificial
<220> FEATURE:
<223> OTHER INFORMATION: Synthetic Reticulitermes flavipes gut symbiont
      oligonucleotide

<400> SEQUENCE: 11

```
ttaattaaaa tgagatttcc atctattttc actgctgttt tgttcgcagc ctcaagtgct    60
ttagcacaat ggatgcagat cggtggtaag cagaaatatc ctgcctttaa gccaggtgct   120
aagtacggaa gaggttattg tgacggacag tgccctcacg acatgaaggt gtctagtgga   180
agagcaaacg ttgacggatg gaagccacaa gacaacgacg aaaatagtgg aaatggaaaa   240
ttgggtacat gttgctggga gatggatata tgggaaggaa acttagtgtc ccaagcctac   300
accgttcacg ctggttccaa gtccggacaa tatgagtgta ctggaacaca atgcggtgac   360
accgacagtg gtgaaagatt caagggaaca tgcgataaag atggttgtga tttcgcaagt   420
tacagatggg gagctacaga ctattacggt cctggaaaga ccgtgacac caaacagcca   480
atgacagtcg tgacccagtt cattggtgac cctttgactg agataaagag agtttatgta   540
caaggaggaa aagtcataaa caattccaaa acatctaact taggttcagt gtacgattct   600
ttgactgagg ccttctgcga tgacaccaaa caggttacag tgatacaaa tgactttaag   660
gctaaaggag gtatgtctgg attctccaag aacttagaca ccccacaagt tttggtgatg   720
tctttatggg atgaccatac agctaatatg ttatggttag attctactta tcctaccgat   780
agtacaaagc caggtgccgc aagaggtact tgtgccgtca cctccgggga ccctaaagat   840
```

```
gtggaatcca agcaagccaa ctctcaggta gtttacagtg acattaagtt tggtcctatt    900
aattcaacat acaaagcaaa ttaaggcgcg cc                                  932
```

<210> SEQ ID NO 12
<211> LENGTH: 1010
<212> TYPE: DNA
<213> ORGANISM: Artificial
<220> FEATURE:
<223> OTHER INFORMATION: Synthetic Reticulitermes flavipes gut symbiont
      oligonucleotide

<400> SEQUENCE: 12

```
ttaattaaaa tgagatttcc atctattttc actgctgttt tgttcgcagc ctccagtgca     60
ttagcagagt ttacattcac aaccgatgta tccggtttac cttgtgggtt aaacggtgcc    120
ttgtactttg tcgccatgga cgaggacgga ggtaaagcaa agcatccatt atccaaacca    180
ggtgctaagt acgaatggg ttactgtgac gcccaatgtc cacacgatat gaagtttatc     240
gaaggattgg caaactgcga gggttggaag cctcaggata atgacgaaaa ctcaggtaat    300
ggaaaatacg gtacttgttg cgctgaaatg gatatatggg aggccaacag tcaagcaaca    360
gcttatactg tgcatgcctg ttccaagacc ggagcaacca aatggtccgg aaatgactgt    420
ggtgatgatg acaacagata caatggaatt tgcgataagg acggttgcga ttacaactca    480
tggagattag gtaatcagac tttcttcgga cctggtttaa ttgtagatag ttccaaacct    540
gtaacagtcg tgacccaatt cataacttcc aataaccaag attcaggaga attagtcgag    600
gttagaagat tgtacgtcca gaacaacaaa gtcatccaga cactgttac taacatccag    660 ggtataaaga atgctgattc tattaccgat tccttttgcg atgatacaaa gtccgttttc    720
ggtgacacta atgactataa ggccaaggga gcaatggctg attttcaaa gagtatcgat    780 ccaggtgtag tcttagtgag aagtttgtgg gacgatcact ccgttaatat gttatggttg    840
gattcaacct accctacaga cagtaacaaa ccaggagcca gtagaggtcc ttgcgcaatt    900
acttcaggaa aaccatctga tgtagaatcc cagtccgctt ctgcatctgt caagttctcc    960 gatattgat tcggtccaat agattctact tatagtaaat aaggcgcgcc              1010
```

<210> SEQ ID NO 13
<211> LENGTH: 1373
<212> TYPE: DNA
<213> ORGANISM: Artificial
<220> FEATURE:
<223> OTHER INFORMATION: Synthetic Mastotermes darwinensis
      oligonucleotide

<400> SEQUENCE: 13

```
ttaattaaaa tgagattccc aagtatattt actgctgttt tgttcgcagc cagttctgct     60
ttagcagcct atgattacaa tgacgtatta accaaaagtt tgttgttcta cgaagctcaa    120
agatccggta agttaccttc tgatcagaaa gtcacctgga gaaaagattc agcattaaac    180
gataagggac aaaatggtga ggacttaact ggtggatatt atgacgccgg tgattacgtg    240
aagtttggtt ttccaatggc atatactgct accgttttgg cttggggttt agtggaccat    300
cctgccggat acagttctgc gggtgtcttg gatgatggta gaaagctgt gaagtgggtt    360 accgattact taatcaaagc ccacgtatca aagaacgaat tatacggaca ggtcggtgac    420
ggtgacgcag atcacgctta ttggggacgt ccagaggata tgacaatggc aagaccagca    480
tacaaaatag acacttcaag accaggttcc gacttagcgg tgaaaccgc agcggcattg    540 gctgctgcat ctattgtgtt taagtcaaca gattctaatt acgccaacac cttattgacc    600
```

```
cacgcaaaac aattattcga ctttgccaat aactatagag gtaagtatag tgattccata    660
acacaggcat ctaatttcta cagtagttcc gactataaag atgaattggt ttgggcagct    720
gtatggttgt acagagccac taacgatcag acctatttga caactgcaga gaagttatac    780
tcagacttgg gattacagtc ctggaacgga ggtttcacat gggacaccaa aattagtgga    840
gtagaagtgt tattggctaa gattactggt aaacaggcat ataaggacaa agtaaaggga    900
tattgtgatt atatctcagg atctcagcag aaaacaccta aaggattagt ttacatagat    960
aagtggggtt ccttaagaat ggccgcaaac gccgcatata tttgcgctgt agccgcagac   1020
gtcggaatca gttcaacagc ttacagacag ttcgccaaaa cacagattaa ttacatattg   1080
ggtgatgccg gacgttcttt tgtggttggt tacggaaaca acccacctac acacccacat   1140
cacagatcca gttcatgtcc tgacgcccca gcaacatgcg attggaataa ctacaacagt   1200
gctaacccta atccacatgt tttatacggt gcattagttg gtggaccaga ttccaacgat   1260
aattatcaag acttaagatc agattatgtc gccaacgaag tggcaacaga ctacaatgca   1320
gccttccagt cattgttagc attaatcgtg gacttaggtt tgtaaggcgc gcc           1373
```

<210> SEQ ID NO 14
<211> LENGTH: 1430
<212> TYPE: DNA
<213> ORGANISM: Artificial
<220> FEATURE:
<223> OTHER INFORMATION: Synthetic Reticulitermes flavipes oligonucleotide

<400> SEQUENCE: 14

```
ttaattaaaa tgagatttcc aagtatattt actgccgtct tatttgcagc ctcaagtgct     60
ttagccgctt atgactacaa aacagtattg tccaattcct tgttgttcta cgaagctcaa    120
agatccggta agttaccttc tgatcagaaa gtcacttgga gaaaggattc agcattaaac    180
gacaaaggac aaaagggtga ggacttgact ggaatgagat tcccatcaat attcaccgcc    240
gtgttgtttg ctgcatcttc agctttagcc ggttattacg atgccggtga tttcgtcaaa    300
ttcggatttc caatggctta cactgtaact gtcttggcct ggggtgttat tgattacgaa    360
agtgcatact ctgctgccgg agcattggat tcaggtagaa aggcattaaa gtacgggacc    420
gactatttct taaaggccca tacagctgcc aatgagttct atggacaggt aggtcaagga    480
gatgtggacc atgcatattg gggacgtcca gaggatatga ctatgtctcg tcctgcttac    540
aaaatagaca cctccaagcc aggttccgac ttagctgcag agactgcagc tgccttagcc    600
gcaacagcca tcgcatacaa atcagctgat gcaacatatt ccataacctt gataactcat    660
gcaaagcagt tattcgactt tgctaacaac tatagaggaa aatatagtga ttccattacc    720
gatgccaaga acttttatgc ctcaggagat tataaagacg aattagtctg ggccgctgca    780
tggttataca gagctacaaa tgacaacaca tatttgacca aggctgaatc cttatacaat    840
gagttcggat tgggaaactg gaatggtgcc ttcaattggg ataacaaaat cagtggagta    900
caggtcttat tggccaagtt aacatcaaaa caggcataca aggataaggt tcagggttac    960
gtggattact tgatctcctc ccaaaaaaag accccctaagg gattagttta cattgatcaa   1020
tggggaacct tgacacacgc tgctaatagt gccttaatcg cgttgcaggc tgccgactta   1080
ggtattaacg cagctaccta tagagcctac gcaaagaagc aaatcgacta tgctttgggt   1140
gatggtggac gttcttatgt ggtgggtttt ggtactaacc cacctgtaag accacatcac   1200
agaagttcca gttgtcctga cgccccagca gtctgcgatt ggaacaccta caattcagct   1260
```

```
ggtccaaacg cccacgtgtt aactggtgcc ttagttggtg gacctgattc taatgattcc    1320
tatactgatg ctagatcaga ctacatttct aacgaggttg caactgatta caacgccgga    1380
tttcagagtg ctgtcgctgg attattaaag gctggagtgt aaggcgcgcc                1430
```

<210> SEQ ID NO 15  
<211> LENGTH: 1373  
<212> TYPE: DNA  
<213> ORGANISM: Artificial  
<220> FEATURE:  
<223> OTHER INFORMATION: Synthetic Reticulitermes speratus oligonucleotide

<400> SEQUENCE: 15

```
ttaattaaaa tgagattccc aagtatattt actgccgtct tatttgcagc ctccagtgca      60
ttagccgctt atgactacaa aacagtattg tccaattcct tgttgttcta cgaagctcaa    120
agatccggta agttaccttc tgaccagaaa gtgacctgga gaaggattc agcattaaac     180 gacaaaggac aaaagggtga ggacttaacc ggtggatatt acgacgccgg agactttgtg    240
aaatttggtt ttccaatggc ttacacagtt accgtattgg catggggtgt tattgattac    300
gaatccgcct actctgccgc aggagcttta gattcaggta gaaaggcctt gaaatatggg    360
accgactatt tcttaaaggc acatacagca gctaacgagt tttacggaca ggtgggtcaa    420
ggtgacgttg accacgcata ctggggacgt cctgaagata tgaccatgag cagaccagca    480
tacaaaatag acacttctaa gcctggttcc gacttagctg cagagactgc agctgcatta    540
gcagccacag ctattgcata caaatctgcc gatgcaacat attccaacaa tttgataaca    600
catgcaaaac aattattcga ctttgccaac aattacagag gaaaatattc cgatagtatt    660
accgatgcca gaactttta tgcttctggt gattacaaag acgaattggt atgggccgct    720
gcatggttgt acagagcaac caatgacaac acatatttga ctaaggcaga atccttatac    780
aatgaatttg gttttgggaaa cttcaatggt gccttcaatt gggataacaa agtctccgga    840
gtccaggtgt tattggccaa gttaacctca aaacaagtgt ataaggataa ggtacagtct    900
tacgtggact atttgatctc ctcacaaaaa aagacaccaa aaggtttagt gtacatcgat    960
caatggggta ctttaagaca cgcagctaat tctgctttga tcgctttgca ggcagctgac   1020
ttaggaatta acgctgctac ttacagagcc tacgcaaaga agcaaatcga ctatgctttg   1080
ggtgatggtg aagatcccta tgttattgga tttgggacca accctccagt aagaccacat   1140
cacagaagtt catcttgccc agatgcacca gctgtctgcg attggaacac ctataactcc   1200
gctggtccaa acgcccacgt gttaaccggt gcattggttg gaggacctga tagtaatgat   1260
agttataccg atgctcgttc tgactacata tccaacgaag tggcaactga ttacaatgcg   1320
ggtttccaat ccgctgtcgc tggattattg aaggcgggtg tctaaggcgc gcc            1373
```

<210> SEQ ID NO 16  
<211> LENGTH: 1373  
<212> TYPE: DNA  
<213> ORGANISM: Artificial  
<220> FEATURE:  
<223> OTHER INFORMATION: Synthetic Coptotermes formosanus oligonucleotide

<400> SEQUENCE: 16

```
ttaattaaaa tgagattccc ttccattttc actgctgttt tgttcgcagc ctcaagtgct     60
ttagcagcct atgactacaa gacagtattg aagaactcct tgttgttcta cgaagctcaa    120
agaagtggaa aattgcctgc agaccagaag gtgacctgga gaaagattc cgcattaaac    180
```

```
gacaagggac agaagggaga ggacttaact ggaggttatt acgacgccgg agactttgtg      240
aagttcggtt ttccaatggc atacacagtt accgtgttgg cctggggttt agtcgattat      300
gaatctgctt acagtactgc gggtgccttg gatgatggta gaaaggcctt gaaatggggt      360
acagattatt tcttgaaagc acataccgct gccaatgagt tttacggaca ggtgggtcag      420
ggagatgtgg atcatgctta ctggggacgt cctgaggaca tgactatgtc tagaccagct      480
tacaagatcg atacatcaaa acctggtagt gacttagctg cagaaacagc agccgcttta      540
gcagcaaccg caatagctta caagtcagcc gattctacct acagtaacaa cttaattact      600
catgcaaagc agttgttcga ttttgcaaac aattatagag gaaagtactc tgatagtatt      660
accgatgcca agaatttcta tgcatccggt gattataagg acgaattagt atgggctgca      720
gcctggttgt atagagctac aaatgataac acttacttaa ccaaagccga atcattgtat      780
aatgaatttg gtttaggatc ttggaacggt gcattcaatt gggataacaa gatatccgga      840
gttcaggtct tattagccaa attgacatcc aaacaagcat acaaagataa agttcagggt      900
tatgttgatt acttagtctc ctctcaaaag aaaactccaa agggattggt ctatattgac      960
caatggggaa ccttaagaca cgcagctaat agtgccttga tcgctttaca ggccgctgat     1020
ttgggtataa acgctgctag ttatagacaa tacgcaaaga agcaaattga ttatgcctta     1080
ggtgacggag tcgttcttta cgtggtcgga ttcggaacta ccctccagt aagacctcat      1140 catagatcca gttcctgtcc tgacgcacca gccgcttgcg actggaatac ttacaactct     1200
gccggaccaa atgcccacgt cttgaccgga gccttagtag gtggaccaga ttccaacgat     1260
agttacacag attcacgttc tgattatatc agtaacgaag tcgctactga ttacaatgcc     1320
ggtttccaat ctgcagttgc tggtttgttg aaagccggag ataaggcgc gcc            1373
```

<210> SEQ ID NO 17
<211> LENGTH: 1373
<212> TYPE: DNA
<213> ORGANISM: Artificial
<220> FEATURE:
<223> OTHER INFORMATION: Synthetic Coptotermes acinaciformis
      oligonucleotide

<400> SEQUENCE: 17

```
ttaattaaaa tgagattccc tagtattttc actgccgtct tatttgcagc cagttctgct       60
ttagccgcat atgattatac cacagttttg aaaagttcct tattgttcta cgaagctcaa      120
agatccggta agttgccagc cgaccagaag gtcacttgga gaaagattc agcattagac       180 gataaaggaa ataatggaga ggacttaaca ggaggttatt atgacgctgg tgattttgtg      240
aagtttggtt ttccttttagc atacaccgct actgttttag cctggggttt ggtggactat     300
gaagcgggtt actcatccgc tggagccaca gatgacggta gaaaggcagt gaaatgggca     360
accgactatt tgttgaaggc acatactgcc gctaccgagt tatacggaca ggtcggggac     420
ggtgacgccg atcacgcata ttggggacgt cctgaagata tgactatggc tagaccagca     480
tacaagatcg acgctagcag accaggatct gacttagcgg gtgaaaccgc tgccgcttta     540
gccgctgcat ccatagtttt caaaggtgta gattcttcat attctgacaa cttgttagct     600
cacgctaaac agttatttga tttcgctgac aattatagag gaaatacag tgattccata      660 acacaagctt caaactttta cgcctccgga gattacaaag acgagttagt ctgggctgcc     720
acttggttgt acagagcaac caacgataat acatatttga ccaaagcaga atccttgtac     780
aacgagttcg gattaggaaa ctggaacgga gccttaatt gggacaacaa ggtgtccggt      840
gttcaggtgt tgttagccaa attgacctcc aagcaggctt ataaagacac cgttcaagga     900
```

```
tacgtcgatt atttgattaa caatcagcaa aagaccccaa agggtttgtt atacatagac    960
caatggggga ccttgagaca cgcagctaat gctgccttaa taatcttaca ggctgctgat   1020
ttgggtattt ctgccgacag ttatagacaa ttcgcaaaga agcaaataga ttacgcttta   1080
ggtgacggag gtagatcata tgtagttggt tttggagaca atcctccaac acatcctcat   1140
caccgttctt cctcatgccc tgacgcccca gcagtatgcg attggaatac tttcaattca   1200
cctgatccaa actttcatgt cttaaccgga gctttagtgg gaggtcctga tcagaacgat   1260
aactacgttg atgatcgttc tgactacgtg tccaacgagg ttgcaaccga ctataatgca   1320
ggattccaaa gtgctgtggc cgctttagtt actttaggag tttaaggcgc gcc         1373
```

<210> SEQ ID NO 18
<211> LENGTH: 1373
<212> TYPE: DNA
<213> ORGANISM: Artificial
<220> FEATURE:
<223> OTHER INFORMATION: Synthetic Nasutitermes walkeri oligonucleotide

<400> SEQUENCE: 18

```
ttaattaaaa tgagatttcc atctattttc actgccgtct tatttgcagc ctcaagtgct     60
ttagcagcct atgattacaa acaagtattg agagattcct tattgttcta cgaagctcag    120
agaagcggta gattaccagc agaccagaag gtcacctgga gaaaagattc cgccttgaat    180
gatcagggag agcaaggtca agacttaacc ggaggttatt ttgacgccgg tgattttgtg    240
aagtttggat tcccaatggc ttatacagca accgttttgg cctggggttt aatcgacttt    300
gaagccggtt actcttctgc tggtgccttg gacgatggta gaaaagcagt aaagtgggct    360
actgattact ttataaaagc ccatacttct caaaacgagt tttacggaca gtcggtcag    420 ggtgacgtag atcacgcata ttggggacgt cctgaagata tgacaatggc tagaccagcc    480
tacaagattg ataccagcag accaggtagt gacttagcag gagaaactgc tgcagctttg    540
gctgccgcat ccatcgtttt caagaatgta gatggtacat attccaacaa cttacttact    600
catgctagac agttgtttga tttcgccaac aattacagag aaaatactc tgatagtatt    660 accgatgcaa gaaactttta cgctagtgcc gactatagag atgagttagt ctgggcagct    720
gcctggttgt acagagcaac caacgacaat tcttacttga acactgctga atcattatac    780
aacgagtttg gattgcaaaa ttggggtgga gggttaaact gggattctaa agtgagtggt    840
gttcaagttt tgttagccaa gttgaccaac aaacaagagt ataaggacac tattcaatca    900
tacgtgaatt acttaatcaa taaccaacag aaaactccaa agggattgtt atacattgac    960 atgtgggga ccttgagaca cgcagctaac gcagcccttta taatgttaga agctgccgac   1020
ttaggtttat ccgcttcatc ttatagacag ttcgcccaaa cacaaataga ctacgcattg   1080
ggggacggtg gacgttcttt tgtctgtggt ttcggttcta atcctccaac tagacctcat   1140
catagatcca gttcatgccc gcctgctcca gctacctgtg attggaatac attcaattct   1200
cctgacccaa actacaatgt tttatccggt gccttggttg gtggtcctga ccagaatgat   1260
aactacgtgg acgatagaag tgattatgtc cataatgagg tagcaactga ctacaatgcc   1320
ggtttccaat cagccttagc cgctttagtc gccttaggtt actaaggcgc gcc          1373
```

<210> SEQ ID NO 19
<211> LENGTH: 1373
<212> TYPE: DNA
<213> ORGANISM: Artificial
<220> FEATURE:
<223> OTHER INFORMATION: Synthetic Nasutitermes takasagoensis oligonucleotide

<400> SEQUENCE: 19

| ttaattaaaa tgagatttcc atctattttc actgccgtct tatttgcagc ctccagtgca | 60 |
| ttagcagcct atgattataa acaagttttg agagattcct tattgttcta cgaagctcag | 120 |
| agaagcggta gattaccagc agaccagaag gtcacttgga gaaaagattc agccttgaat | 180 |
| gatcagggag atcaaggtca agacttaacc ggaggttatt ttgacgccgg tgattttgtg | 240 |
| aaatttggtt tcccaatggc atatactgct accgtcttgg cctggggttt aatcgatttt | 300 |
| gaggcaggat acagttccgc tggtgccttg gatgacggta gaaaagcagt aaagtgggca | 360 |
| actgattact ttataaaggc ccacacttca cagaatgagt tttacggaca agtcggtcag | 420 |
| ggtgacgctg atcacgcttt ctggggacgt cctgaagata tgaccatggc tagaccagcc | 480 |
| tacaagattg acaccagcag accaggtagt gacttagcgg gtgaaaccgc agcggcattg | 540 |
| gcagctgcca gtatcgtgtt tagaaatgtt gatggtacat actctaacaa cttacttact | 600 |
| catgccagac aattatttga ctttgcaaat aactacagag aaaatactc agattccata | 660 |
| accgacgcta gaaactttta cgccagtgca gattaccgtg acgaattggt ttgggctgcc | 720 |
| gcatggttgt acagagctac aaatgacaac acttacttga ataccgcaga atccttgtat | 780 |
| gatgaatttg gattgcagaa ctggggtgga gggttaaact gggattcaaa ggtgtctggt | 840 |
| gtccaggtct tgttagcaaa attgaccaac aaacaggctt acaaagatac tgtgcagtct | 900 |
| tacgtgaatt acctgattaa taaccagcaa aagaccccaa aaggattgtt atacattgat | 960 |
| atgtggggta cattgagaca cgccgcaaat gctgcattca tcatgttgga agctgccgag | 1020 |
| ttgggtttat ccgcatcatc ttacagacag tttgctcaaa ctcagatcga ctacgctttg | 1080 |
| ggtgacggtg aagaagtttt cgtctgtggt tttggttcaa accctcctac aagaccacat | 1140 |
| catcgttctt ccagttgccc gcctgcccca gcaacttgtg actggaatac attcaactca | 1200 |
| cctgacccaa attaccacgt gttatctgga gctttggtag aggaccaga tcaaaacgat | 1260 |
| aattatgtgg atgatagatc cgactacgtc cataacgaag tggcaaccga ctacaacgcc | 1320 |
| ggatttcaga gtgctttggc agccttagtt gctttgggtt attaaggcgc gcc | 1373 |

<210> SEQ ID NO 20
<211> LENGTH: 1370
<212> TYPE: DNA
<213> ORGANISM: Artificial
<220> FEATURE:
<223> OTHER INFORMATION: Synthetic Panesthia cribrata oligonucleotide

<400> SEQUENCE: 20

| ttaattaaaa tgagatttcc atctattttc actgctgttt tgttcgcagc ctcaagtgct | 60 |
| ttagccgcaa cttatgatta ctcccaattg atccagtatt ccttattgtt ctacgaggct | 120 |
| cagagaagtg gaaaattgcc agccgatcag aaggtgacct ggagaaaaga ttccgcatta | 180 |
| aatgacaagg gacaaaatgg tgaggactta actggaggat attacgatgc cggtgattat | 240 |
| gtcaaatttg gatacccaat ggcctttaca gcaaccttgt tagcctggag tttgattgac | 300 |
| tatgaacaag gttatgcaaa ggctaattcc gtcgaggacg cgagaaaggc agtgaaatgg | 360 |
| gccactgact atttcttaaa agcccatgta tcagaacacg agttctacgg acaggtggga | 420 |
| gagggaaact tggatcataa ttcatgggga cgtcctgagg acatgactat ggaaagacca | 480 |
| gcatataaga ttgatgagca aaaccctgga accgaattag ctgccgaaac tgctgcagcc | 540 |
| ttagccgctg cctccatcgt gttcaaatct gttgacccta gttactccaa tacattactt | 600 |

```
actcacgcta aacaattgta tgactttggt gataaactttta gaggaaaata cagtgaatcc    660
ataaacgacg cccaacagtt ctatagatca acgaatttg aggacgaatt ggtttggggt      720
gccttatggt tgtacaaggc tactatggat gagagtttct taacaaaagc ccaacagtac     780
tatgacgatt ttggaattgc cgagtataat ccttggttca gttgggacca gaaatgtact     840
tcctcacagt tgttattggc acaaattacc caggaacaac aatacataga caaaatcact     900
gcttattgtg accatatgat ttcaggacag caaagaactc caaagggttt agtgtacatt     960
gacacttggg gttcttttgag aatggccgca aacgctgcct acttatgttt ggaagcagct   1020
tcagccggtt taaaacctac agagtacaga gcattcgcaa cagaacaaat aggatacgca   1080
ttgggtgata caggaaaatc tttcgtggtt ggatttggtg ttaacccacc ttcccatgaa    1140
agtcacagat catcttcctg cccagacgct ccagccccctt gtgattgggt aacatatggt   1200
agtgtcgatc caaaccctca tgtgttatac ggagcaattg ttggtggacc aggtcctaac   1260
gatgaatatg atgaccagag atacgattat gtacacaatg aagtcgctga tgactacaac   1320
gctggttatc aaggatgcct ggccgctttg aacgagttgt aaggcgcgcc              1370
```

<210> SEQ ID NO 21
<211> LENGTH: 326
<212> TYPE: PRT
<213> ORGANISM: Holomastigotoides mirabile

<400> SEQUENCE: 21

Met Leu Val Ala Leu Ala Val Ser Val Phe Cys Glu Lys His Pro Lys
1               5                   10                  15

Phe Val Trp Gln Gln Cys Thr Lys Gly Gly Cys Ser Asp Val Ser Gly
            20                  25                  30

Tyr Leu Val His Asp Arg His Ile Gly Asp Val Trp Asp Arg Glu Asn
        35                  40                  45

Thr Asp Tyr Pro Glu Leu Asp Tyr Asp Ala Asn Val Gly Val Thr Val
    50                  55                  60

Ser Ala Asp Gly Lys Thr Leu Ser Gln Arg Leu Val Ser Lys Leu Trp
65                  70                  75                  80

Asp Asp Lys Lys Ala Val Gly Ser Arg Val Tyr Ile Val Asp Thr Thr
                85                  90                  95

Asp Lys Lys Tyr Gln Leu Phe Gln Phe Val Gly Lys Glu Phe Thr Tyr
            100                 105                 110

Thr Val Asp Met Ser Gln Ile Pro Cys Gly Val Asn Ala Ala Leu Tyr
        115                 120                 125

Thr Val Glu Met Pro Ala Glu Gly Lys Ser Pro Gly Gly Val Glu Tyr
    130                 135                 140

Gly Tyr Gly Tyr Cys Asp Ala Asn Cys Val Asp Gly Gly Cys Cys Met
145                 150                 155                 160

Glu Phe Asp Ile Gln Glu Ala Ser Ser Lys Ala Ile Val Tyr Thr Thr
                165                 170                 175

His Ser Cys Gln Ser Gln Thr Gly Gly Cys Asp Thr Ser Gly Cys Gly
            180                 185                 190

Tyr Asn Pro Tyr Arg Asp Ser Asn Asp His Ala Phe Trp Gly Gln Thr
        195                 200                 205

Ile Asn Val Asn Gln Pro Val Thr Ile Val Thr Gln Phe Val Gly Ser
    210                 215                 220

Gly Gly Ser Leu Thr Glu Val Lys Arg Leu Tyr Val Gln Gly Gly Lys
225                 230                 235                 240

Val Thr Pro Ala Ala Lys Ser Leu Ser Asp Ser Tyr Cys Asn Val Asn

```
                245                 250                 255
Asp Tyr Arg Ser Leu Lys Thr Ile Gly Ala Ser Phe Gln Arg Gly His
            260                 265                 270

Val Val Val Phe Ser Leu Trp Asp Ser Asp Gly Met Ser Trp Met Asp
            275                 280                 285

Gly Gly Asn Ala Gly Pro Cys Thr Ser Tyr Asn Val Ala Thr Val Glu
            290                 295                 300

Ser Ser Gln Pro Asn Leu Lys Val Thr Trp Ser Asn Val Lys Phe Gly
305                 310                 315                 320

Asp Ile Asp Ser Thr Tyr
                325

<210> SEQ ID NO 22
<211> LENGTH: 303
<212> TYPE: PRT
<213> ORGANISM: Coptotermes lacteus symbiont

<400> SEQUENCE: 22

Glu Cys Thr Lys Gly Gly Cys Thr Asn Lys Asn Gly Tyr Ile Val His
1               5                   10                  15

Asp Lys His Val Gly Asp Ile Gln Asn Arg Asp Thr Leu Asp Pro Pro
                20                  25                  30

Asp Leu Asp Tyr Glu Lys Asp Val Gly Val Thr Val Ser Gly Gly Thr
            35                  40                  45

Leu Ser Gln Arg Leu Val Ser Thr Trp Asn Gly Lys Lys Val Val Gly
        50                  55                  60

Ser Arg Leu Tyr Ile Val Asp Glu Ala Asp Glu Lys Tyr Gln Leu Phe
65                  70                  75                  80

Thr Phe Val Gly Lys Glu Phe Tyr Thr Val Asp Met Ser Gln Ile
                85                  90                  95

Gln Cys Gly Ile Asn Ala Ala Leu Tyr Thr Val Glu Met Pro Ala Ala
            100                 105                 110

Gly Lys Thr Pro Gly Gly Val Lys Tyr Gly Tyr Gly Tyr Cys Asp Ala
        115                 120                 125

Asn Cys Val Asp Gly Asp Cys Cys Met Glu Phe Asp Ile Gln Glu Ala
    130                 135                 140

Ser Asn Lys Ala Ile Val Tyr Thr Thr His Ser Cys Gln Ser Gln Thr
145                 150                 155                 160

Ser Gly Cys Asp Thr Ser Gly Cys Gly Tyr Asn Pro Tyr Arg Asp Ser
                165                 170                 175

Gly Asp Lys Ala Phe Trp Gly Thr Thr Ile Asn Val Asn Gln Pro Val
            180                 185                 190

Thr Ile Val Thr Gln Phe Ile Gly Ser Gly Ser Leu Thr Glu Val
        195                 200                 205

Lys Arg Leu Cys Val Gln Gly Gly Lys Thr Phe Pro Pro Ala Lys Ser
    210                 215                 220

Leu Thr Asp Ser Tyr Cys Asn Ala Asn Asp Tyr Arg Ser Leu Arg Thr
225                 230                 235                 240

Met Gly Ala Ser Met Ala Arg Gly His Val Val Phe Ser Leu Trp
                245                 250                 255

Asp Ser Asn Gly Met Ser Trp Met Asp Gly Gly Asn Ala Gly Pro Cys
            260                 265                 270

Thr Ser Tyr Asn Ile Glu Ser Leu Glu Ser Ser Gln Pro Asn Leu Lys
        275                 280                 285

Val Thr Trp Ser Asn Val Lys Tyr Gly Glu Ile Asp Ser Pro Tyr
```

<210> SEQ ID NO 23
<211> LENGTH: 364
<212> TYPE: PRT
<213> ORGANISM: Cryptocercus punctulatus symbiont

<400> SEQUENCE: 23

Met Leu Leu Phe Leu Leu Ser Arg Ile Ser Val Ser Trp Leu Ser Thr
1               5                   10                  15

Ser Gly Ser Lys Ile Thr Asp Gly Gly Gln Thr Val Arg Leu Thr Gly
            20                  25                  30

Val Asn Trp Phe Gly Tyr Glu Thr Ser Glu Glu Val Phe His Gly Leu
        35                  40                  45

Trp Ala Ala Gly Leu His Asp Leu Val Gln Gly Val Ser Gln Lys Lys
    50                  55                  60

Phe Asn Thr Phe Arg Val Pro Ile Ser Ala Ser Val Leu Gln Asp Trp
65                  70                  75                  80

Lys Ala Gly Lys Pro Asn Pro Lys Pro Asn Ile Asn Leu Asn Val Asn
                85                  90                  95

Ala Asp Leu Glu Gly Leu Asn Asn Gln Gln Ile Phe Asp Leu Phe Leu
            100                 105                 110

Ala Asp Cys Lys Lys Tyr Lys Ile Tyr Val Phe Ile Asp Val His Gly
        115                 120                 125

Val Thr Asp Gly Ser Tyr Met Asp Asn Leu Trp Tyr Thr Ser Ala His
    130                 135                 140

Pro Ala Glu Trp Ile Tyr Ser Ala Leu Glu Trp Phe Ala Asp His Tyr
145                 150                 155                 160

Lys Gly Asp Gln Thr Ile Ile Gly Ile Asp Ile Lys Asn Glu Pro His
                165                 170                 175

Gly Arg Cys Glu Gln Ala Glu Ala Ala Lys Trp Ser Asp Ser Lys Asp
            180                 185                 190

Asn Asn Asn Trp Lys Tyr Phe Ile Glu Thr Ala Ala Ala Arg Ile Leu
        195                 200                 205

Gly Lys Asn Pro Asn Leu Leu Ile Leu Val Glu Gly Ile Glu Cys Tyr
    210                 215                 220

Asn Asn Asn Trp Gly Trp Trp Gly Gly Asn Leu Ile Pro Val Asn Asp
225                 230                 235                 240

Tyr Pro Ile Asn Leu Gly Ser Gly Gln Lys Gln Leu Val Tyr Ser Pro
                245                 250                 255

His Glu Tyr Gly Pro Ser Val Asn Asp Gln Ser Trp Phe Lys Ser Gly
            260                 265                 270

Phe Asn Tyr Asp Ser Leu Tyr Ala Asp His Trp Gln Lys Met Trp Met
        275                 280                 285

Phe Ile Ile Glu Lys Asn Ile Ala Pro Ile Leu Ile Gly Glu Trp Gly
    290                 295                 300

Gly His Val Val Glu Pro Asn Thr Thr Trp Met Lys Ala Leu Val Gln
305                 310                 315                 320

Leu Ile Ser Lys Tyr Gly Leu Ser Gln Thr Phe Trp Cys Leu Asn Pro
                325                 330                 335

Asp Ser Gly Asp Thr Gly Gly Leu Leu Glu Asn Asp Trp Ile Thr Trp
            340                 345                 350

Asp Thr Ala Lys Leu Asp Ile Ile Lys Gly Val Leu
        355                 360

<210> SEQ ID NO 24
<211> LENGTH: 372
<212> TYPE: PRT
<213> ORGANISM: Mastotermes darwiniensis symbiont

<400> SEQUENCE: 24

```
Met Leu Val Leu Leu Ala Ser Phe Gly Val Ala Tyr Tyr Ile Ser Ala
1               5                   10                  15

Ser Gly Asn Glu Leu Val Asp Pro Thr Gly Lys Gln Leu Arg Ile Thr
            20                  25                  30

Gly Ile Asn Trp Phe Gly Phe Glu Thr Ser Gln Ser Ala Phe His Gly
        35                  40                  45

Leu Trp Asn Ala Asn Leu His Lys Val Val Gln Gln Val Ala Glu His
    50                  55                  60

Gly Phe Asn Cys Phe Arg Cys Pro Ile Ser Cys Asp Leu Ile His Lys
65                  70                  75                  80

Trp Met Arg Gly Asp Lys Thr Pro Leu Gln Trp Ile Asn Thr Glu Pro
                85                  90                  95

Asp Ala Asn Pro Asp Met Lys Gly Ile Ser Ser Arg Gly Ile Trp Asp
            100                 105                 110

Met Phe Met Ala Asp Cys Lys Lys Ala Gly Ile Lys Val Phe Ile Asp
        115                 120                 125

Ile His Gly Ile Gln Pro Asp Ser Tyr Thr Leu Pro Leu Trp Gly Asp
    130                 135                 140

Thr Glu Tyr Leu Ile Ser Ala Leu Glu Trp Phe Ala Asn Glu Phe Lys
145                 150                 155                 160

Asn Asp Asp Thr Phe Ile Ala Ile Asp Val Lys Asn Glu Pro His Gln
                165                 170                 175

Gln Gly Gln Gly Cys Gly Thr Gly Ala Asn Asp Ala Val Trp Glu Ser
            180                 185                 190

Ser Thr Arg Ser Asn Asn Trp Pro Tyr Val Ala Gly Leu Ala Gly Lys
        195                 200                 205

Arg Ile Leu Ala Lys Asn Pro Gly Leu Leu Ile Leu Val Glu Gly Asn
    210                 215                 220

Gln Cys Tyr Lys Gly Asp Ser Ser Trp Trp Gly Gly Asn Leu Ala Gly
225                 230                 235                 240

Val Lys Asp Ile Pro Val Asp Val Gly Asn Pro Lys Lys Leu Val Tyr
                245                 250                 255

Ser Pro His Glu Tyr Gly Pro Ser Val Asn Asp Gln Ala Trp Phe His
            260                 265                 270

Pro Thr Ile Asn Tyr Asp Gln Leu Tyr Ser Gln His Trp His Lys His
        275                 280                 285

Trp Leu Tyr Ile His Glu Glu Gly Ile Ala Pro Leu Leu Ile Gly Glu
    290                 295                 300

Trp Gly Gly Lys Leu Ser Gly Thr Asn Thr Gln Trp Met Lys Leu Phe
305                 310                 315                 320

Val Asn Leu Ile Ala Gln Tyr Gly Leu Ser His Thr Phe Trp Cys Leu
                325                 330                 335

Asn Pro Asn Ser Gly Asp Thr Gly Gly Leu Leu Lys Asp Asn Trp Lys
            340                 345                 350

Asp Trp Asp Glu Glu Lys Tyr Ala Phe Ile Lys Pro Cys Leu Gly Gly
        355                 360                 365

Ser Leu Phe Lys
    370
```

<210> SEQ ID NO 25
<211> LENGTH: 306
<212> TYPE: PRT
<213> ORGANISM: Neotermes koshunensis symbiont

<400> SEQUENCE: 25

```
Met Leu Gly Leu Leu Leu Ser Pro Ser Leu Ser Glu Ala Asp Pro Asp
1               5                   10                  15

Leu Val Arg Leu His Val Asp Gly Asn Arg Ile Val Met Gly Lys Pro
            20                  25                  30

Gly Leu Ala Ser Ser Lys Thr Ala Met Leu Arg Gly Val Ser Cys Ser
        35                  40                  45

Trp His Asn Trp Trp Pro Gln Phe His Ser Ala Ala Thr Val Arg Gly
    50                  55                  60

Leu Lys Ser Asp Phe His Ala Asn Val Val Arg Thr Phe Ile Gly Val
65                  70                  75                  80

Glu Lys Glu Gly Gly Phe Leu Thr Asn Gln Gln Lys Ala Tyr Asp Cys
                85                  90                  95

Cys Tyr Ala Val Val Asp Glu Cys Ile Ala Gln Gly Ile Tyr Val Ile
            100                 105                 110

Ile Asn Trp Ala Ser Phe Val Leu Thr Tyr Gln Thr Gln Ala Thr Gln
        115                 120                 125

Phe Phe Lys Thr Val Ala Thr Lys Tyr His Ser Ser Ser Tyr Val Ile
    130                 135                 140

Tyr Glu Leu Leu Asn Glu Pro Glu Ala Ala Thr Trp Ala Gln Ile Lys
145                 150                 155                 160

Pro Tyr Ser Gln Ala Leu Ile Gln Thr Ile Arg Ala Ile Asp Pro Ser
                165                 170                 175

Asn Leu Ile Leu Val Pro Thr Pro Arg Trp Asp Gln Glu Ile Gly Ala
            180                 185                 190

Ala Ala Asn Asp Pro Ile Thr Gly Asp Asn Asn Leu Ala Tyr Thr Leu
        195                 200                 205

His Ile Tyr Thr Gly Thr His Pro Ala Ser Tyr Arg Asp Asp Ala Arg
    210                 215                 220

Ala Ala Lys Lys Lys Ile Pro Val Trp Ala Asp Glu Asn Gly Ala Met
225                 230                 235                 240

Asn Ala Asp Gly Lys Gly Ala Leu Asp Arg Thr Gly Trp Asn Thr Trp
                245                 250                 255

Ile Ala Phe Tyr Glu Glu Leu Gln Ile Pro Trp Leu Gly Tyr Gly Thr
            260                 265                 270

Gln Asp Thr Ser Glu Thr Cys Ser Ile Phe Lys Ser Thr Asp Ser Phe
        275                 280                 285

Asn Asp Leu Ser Asp Trp Gly Lys Leu Leu Lys Glu Thr Ile Arg Lys
    290                 295                 300

Tyr Gln
305
```

<210> SEQ ID NO 26
<211> LENGTH: 300
<212> TYPE: PRT
<213> ORGANISM: Hodotermopsis sjoestedti symbiont

<400> SEQUENCE: 26

```
Met Leu Val Leu Leu Leu His Phe Ile Asn Ser Lys Ala Pro Pro
1               5                   10                  15

Phe Gly Arg Leu Cys Val Glu Gly Asn Lys Ile Val Gly Asn Lys Arg
            20                  25                  30
```

```
Ala Pro Gly Val Leu Arg Gly Val Gly Leu Ser Trp His Asn Trp Trp
            35                  40                  45

Pro Gln Phe Tyr Asn Ala Ala Thr Ile Asn His Leu Lys Asn Asp Phe
 50                  55                  60

His Ala Asn Val Ile Arg Ala Ala Ile Gly Val Glu Lys Glu Asn Gly
 65                  70                  75                  80

Tyr Phe Asp Asn Gln Gln Asn Ala Tyr Asp Leu Leu Tyr Ala Ala Val
                    85                  90                  95

Asp Ala Ala Leu Ser Ala Gly Ile Tyr Val Ile Val Asp Trp Gln Ala
                100                 105                 110

Phe Gln Ile His Glu Ser Asp Ala Lys Gln Phe Phe Thr Thr Val Val
                115                 120                 125

Asn Lys Tyr Lys Gly Lys Ser Asn Val Ile Tyr Glu Ile Phe Asn Glu
            130                 135                 140

Pro Glu Ser Ala Gly Trp Ser Glu Ile Lys Lys Tyr Ser Ile Ser Leu
145                 150                 155                 160

Ile Gln Thr Ile Arg Ala Ile Asp Ser Asn Ala Phe Ile Leu Val Pro
                165                 170                 175

Thr Pro Asn Trp Asp Gln Tyr Val Glu Gln Ala Ala Asp Pro Ile
                180                 185                 190

Ser Glu Tyr Ser Asn Ile Ala Tyr Thr Ile His Ile Tyr Ala Ala Thr
                195                 200                 205

His Pro Leu Ser Tyr Leu Asp Asn Ala Arg Thr Ala Leu Lys Thr Ile
                210                 215                 220

Ala Leu Phe Gly Thr Glu Ile Gly Ala Met Glu Ala Ser Gly Asp Gly
225                 230                 235                 240

Ala Ile Asp Gln Ser Lys Tyr Gln Gln Trp Ile Asp Phe Tyr Glu Gln
                245                 250                 255

Asn Gly Ile Ser Tyr Leu Cys Trp Ala Val Gln Ser Lys Glu Glu Thr
                260                 265                 270

Asp Ser Ile Leu Lys Pro Ser Glu Asp Trp Asn Asp Leu Thr Ala Trp
                275                 280                 285

Gly Lys Leu Cys Lys Ser Thr Ile Thr Ala His Gln
                290                 295                 300

<210> SEQ ID NO 27
<211> LENGTH: 263
<212> TYPE: PRT
<213> ORGANISM: Reticulitermes speratus symbiont

<400> SEQUENCE: 27

Met Arg Lys Ala Met Phe Val Gly Leu Phe Leu Ile Ala Leu Val His
  1               5                  10                  15

Met Glu Leu Glu Asn Asn Ser Thr Arg Leu Arg Val Lys Gly Asn Lys
                 20                  25                  30

Ile Val Val Gly Asn Ser Asp Lys Gly Leu Arg Leu Arg Gly Val Asn
             35                  40                  45

Leu Ser Trp Asn Asn Trp Trp His Gln Phe Tyr Asn Ala Asp Thr Val
 50                  55                  60

Arg His Leu Lys Asn Asp Phe His Val Asn Val Ile Arg Ala Ala Ile
 65                  70                  75                  80

Gly Val Glu Gln Asp Gly Gly Trp Glu Ser Asn Lys Gln Arg Ser Tyr
                 85                  90                  95

Asp Asp Leu Tyr Ala Val Ile Asp Ala Cys Ile Ala Asn Asn Val Tyr
                100                 105                 110
```

```
Val Ile Val Asp Trp Gln Thr Phe Ser Ile Lys Leu Ser Glu Ala Thr
        115                 120                 125

Glu Phe Phe Thr Asn Val Ala Asn Lys Tyr His Ser Ser Ser Tyr Ile
130                 135                 140

Ile Tyr Asp Leu Leu Asn Glu Pro Asp Ser Ser Val Pro Ser Trp Ser
145                 150                 155                 160

Ala Ile Lys Ser Tyr Ala Glu Ser Leu Ile Lys Thr Ile Arg Ala Ile
                165                 170                 175

Asp Ser Ser Asn Leu Ile Ile Val Pro Thr Pro Asn Trp Asp Gln Tyr
            180                 185                 190

Val Lys Gln Ala Ala Asp Pro Ile Thr Ser Asp Ser Asn Leu Ile
        195                 200                 205

Tyr Ser Ile His Ile Tyr Val Gly Thr His Pro Met Ser Tyr Met Asp
    210                 215                 220

Asp Ala Arg Glu Ala Leu Lys Thr Ile Pro Leu Ile Gly Gly Glu Ile
225                 230                 235                 240

Gly Ala Met Asn Ala Asp Gly Asp Gly Ala Leu Asp Val Ser Lys Phe
                245                 250                 255

Asn Gln Trp Ile Asp Phe Leu
            260

<210> SEQ ID NO 28
<211> LENGTH: 220
<212> TYPE: PRT
<213> ORGANISM: Reticulitermes speratus symbiont

<400> SEQUENCE: 28

Met Leu Leu Leu Phe Ser Leu Cys Leu Ile Ser Trp Leu Val Gly Asp
1               5                   10                  15

Ser Gly Arg Thr Thr Arg Tyr Trp Asp Cys Cys Lys Ala Ser Cys Ala
            20                  25                  30

Trp Glu Lys Lys Ala Ala Val Thr Gln Pro Val Asp Thr Cys Gly Lys
        35                  40                  45

Asp Gly Thr Thr Arg Leu Ala Ser Asn Asp Thr Val Lys Ser Ser Cys
    50                  55                  60

Asp Gly Gly Asp Gly Tyr Met Cys Tyr Asp Gln Ala Pro Trp Ala Val
65                  70                  75                  80

Asn Asp Ser Val Ala Tyr Gly Phe Ala Ala Ala Cys Cys Gly Gly
                85                  90                  95

Glu Thr Gly Ala Cys Cys Asn Cys Tyr Glu Leu Thr Phe Thr Ser Gly
            100                 105                 110

Pro Val Asn Gly Lys Lys Met Val Val Gln Val Thr Asn Thr Gly Gly
        115                 120                 125

Asp Leu Gly Ser Asn Gln Phe Asp Leu Ala Ile Pro Gly Gly Gly Val
    130                 135                 140

Gly Ile Tyr Asn Gly Cys Thr Gln Gln Ser Gly Ala Pro Ala Asp Gly
145                 150                 155                 160

Trp Gly Ser Arg Tyr Gly Gly Val Ser Ser Arg Ser Glu Cys Ser Gln
                165                 170                 175

Leu Pro Ser Gly Leu Gln Ala Gly Cys Gln Trp Arg Phe Asp Trp Phe
            180                 185                 190

Gln Asn Ala Asp Asn Pro Ser Ile Asn Phe Asn Gln Val Thr Cys Pro
        195                 200                 205

Ser Glu Leu Ile Ala Arg Thr Asn Cys Lys Arg Thr
    210                 215                 220
```

<210> SEQ ID NO 29
<211> LENGTH: 450
<212> TYPE: PRT
<213> ORGANISM: Pseudotrichonympha grassii

<400> SEQUENCE: 29

```
Met Phe Val Phe Val Leu Leu Trp Leu Thr Gln Ser Leu Gly Thr Gly
1               5                   10                  15

Thr Asn Gln Ala Glu Asn His Pro Ser Leu Ser Trp Gln Asn Cys Arg
            20                  25                  30

Ser Gly Gly Ser Cys Thr Gln Thr Ser Gly Ser Val Val Leu Asp Ser
        35                  40                  45

Asn Trp Arg Trp Thr His Asp Ser Ser Leu Thr Asn Cys Tyr Asp Gly
    50                  55                  60

Asn Glu Trp Ser Ser Ser Leu Cys Pro Asp Pro Lys Thr Cys Ser Asp
65                  70                  75                  80

Asn Cys Leu Ile Asp Gly Ala Asp Tyr Ser Gly Thr Tyr Gly Ile Thr
                85                  90                  95

Ser Ser Gly Asn Ser Leu Lys Leu Val Phe Val Thr Asn Gly Pro Tyr
            100                 105                 110

Ser Thr Asn Ile Gly Ser Arg Val Tyr Leu Leu Lys Asp Glu Ser His
        115                 120                 125

Tyr Gln Ile Phe Asp Leu Lys Asn Lys Glu Phe Thr Phe Thr Val Asp
    130                 135                 140

Asp Ser Asn Leu Asp Cys Gly Leu Asn Gly Ala Leu Tyr Phe Val Ser
145                 150                 155                 160

Met Asp Glu Asp Gly Gly Thr Ser Arg Phe Ser Ser Asn Lys Ala Gly
                165                 170                 175

Ala Lys Tyr Gly Thr Gly Tyr Cys Asp Ala Gln Cys Pro His Asp Ile
            180                 185                 190

Lys Phe Ile Asn Gly Glu Ala Asn Val Glu Asn Trp Lys Pro Gln Thr
        195                 200                 205

Asn Asp Glu Asn Ala Gly Asn Gly Arg Tyr Gly Ala Cys Cys Thr Glu
    210                 215                 220

Met Asp Ile Trp Glu Ala Asn Lys Tyr Ala Thr Ala Tyr Thr Pro His
225                 230                 235                 240

Ile Cys Thr Val Asn Gly Glu Tyr Arg Cys Asp Gly Ser Glu Cys Gly
                245                 250                 255

Asp Thr Asp Ser Gly Asn Arg Tyr Gly Gly Val Cys Asp Lys Asp Gly
            260                 265                 270

Cys Asp Phe Asn Ser Tyr Arg Met Gly Asn Thr Ser Phe Trp Gly Pro
        275                 280                 285

Gly Leu Ile Ile Asp Thr Gly Lys Pro Val Thr Val Thr Gln Phe
    290                 295                 300

Val Thr Lys Asp Gly Thr Asp Asn Gly Gln Leu Ser Glu Ile Arg Arg
305                 310                 315                 320

Lys Tyr Val Gln Gly Gly Lys Val Ile Glu Asn Thr Val Asn Ile
                325                 330                 335

Ala Gly Met Ser Ser Gly Asn Ser Ile Thr Asp Asp Phe Cys Asn Glu
            340                 345                 350

Gln Lys Ser Ala Phe Gly Asp Thr Asn Asp Phe Glu Lys Lys Gly Gly
        355                 360                 365

Leu Ser Gly Leu Gly Lys Ala Phe Asp Tyr Gly Met Val Leu Val Leu
    370                 375                 380
```

```
Ser Leu Trp Asp Asp His Gln Val Asn Met Leu Trp Leu Asp Ser Ile
385                 390                 395                 400

Tyr Pro Thr Asp Gln Pro Ala Ser Gln Pro Gly Val Lys Arg Gly Pro
            405                 410                 415

Cys Ala Thr Ser Ser Gly Ala Pro Ser Asp Val Glu Ser Gln His Pro
            420                 425                 430

Asp Ser Ser Val Thr Phe Ser Asp Ile Arg Phe Gly Pro Ile Asp Ser
            435                 440                 445

Thr Tyr
    450

<210> SEQ ID NO 30
<211> LENGTH: 328
<212> TYPE: PRT
<213> ORGANISM: Reticulitermes flavipes gut symbiont

<400> SEQUENCE: 30

Met Leu Thr Val Leu Phe Leu Leu Ser Leu Gly Trp Cys Glu Lys His
1               5                   10                  15

Pro Ala Phe Gln Trp Lys Lys Asp Gly Val Thr Gln Asn Gly Phe Leu
            20                  25                  30

Val His Asp Arg His Val Gly Asp Asn Trp Tyr Arg Asp Gln Lys Asp
        35                  40                  45

Gly Lys Ser Gly Ala Leu Asp Leu Asp Tyr Glu Asn Asp Val Gly Val
    50                  55                  60

Thr Val Ser Gly Gly Thr Leu Thr Gln Arg Leu Val Ser Asn Tyr Ser
65                  70                  75                  80

Trp Asn Asn Lys Thr Val Val Gly Ser Arg Leu Tyr Ile Met Thr Ala
                85                  90                  95

Asp Glu Lys Lys Tyr Glu Lys Phe Asn Leu Thr Gly Lys Glu Phe Thr
            100                 105                 110

Phe Thr Val Asn Leu Ala Gln Ile Pro Cys Gly Val Asn Ala Ala Leu
        115                 120                 125

Tyr Thr Val Glu Met Pro Ala Asp Gly Ile Asp Ala Thr Asp Gln Thr
    130                 135                 140

Gln Gly Ala Pro Tyr Gly Tyr Gly Tyr Cys Asp Ala Asn Cys Val Asp
145                 150                 155                 160

Gly Gly Cys Cys Pro Glu Phe Asp Gly Ile Glu Ala Thr Ser Lys Ala
                165                 170                 175

Leu Val Phe Thr Thr His Thr Cys Ser Gly Thr Gly Ser Gly Arg Gly
            180                 185                 190

Gly Tyr Thr Gly Cys Asp Thr Ser Gly Cys Gly Tyr Asn Pro Tyr Arg
        195                 200                 205

Asp Asp Asn Asn His Ser Phe Trp Thr Ser Val Asn Leu Ala Gln
    210                 215                 220

Pro Val Thr Ile Val Thr Gln Phe Gln Thr Asn Gly Asp Val Thr Arg
225                 230                 235                 240

Lys Tyr Ile Gln Asn Gly Asn Pro Ile Asp Gly Gly Thr Leu Asn Gln
                245                 250                 255

Ser Arg Cys Ser Gly Lys Gln Asn Met Thr Ser Thr Phe Ser Arg Gly
            260                 265                 270

His Val Val Val Phe Ser Leu Trp Asp Ser Asp Gly Met Ser Trp Leu
        275                 280                 285

Asp Gly Gly Asn Ala Gly Pro Cys Thr Ser Tyr Asn Ile Lys Asp Val
    290                 295                 300
```

```
Glu Thr Arg Thr Pro Asn Leu Thr Val Thr Trp Ser Asp Val Lys Phe
305                 310                 315                 320

Gly Asn Ile Gly Ser Thr Thr Asn
                325
```

<210> SEQ ID NO 31
<211> LENGTH: 292
<212> TYPE: PRT
<213> ORGANISM: Reticulitermes flavipes gut symbiont

<400> SEQUENCE: 31

```
Met Val Leu Cys Ile Leu Leu Gln Trp Met Gln Ile Gly Gly Lys Gln
1               5                   10                  15

Lys Tyr Pro Ala Phe Lys Pro Gly Ala Lys Tyr Gly Arg Gly Tyr Cys
                20                  25                  30

Asp Gly Gln Cys Pro His Asp Met Lys Val Ser Ser Gly Arg Ala Asn
            35                  40                  45

Val Asp Gly Trp Lys Pro Gln Asp Asn Asp Glu Asn Ser Gly Asn Gly
        50                  55                  60

Lys Leu Gly Thr Cys Cys Trp Glu Met Asp Ile Trp Glu Gly Asn Leu
65                  70                  75                  80

Val Ser Gln Ala Tyr Thr Val His Ala Gly Ser Lys Ser Gly Gln Tyr
                85                  90                  95

Glu Cys Thr Gly Thr Gln Cys Gly Asp Thr Asp Ser Gly Glu Arg Phe
                100                 105                 110

Lys Gly Thr Cys Asp Lys Asp Gly Cys Asp Phe Ala Ser Tyr Arg Trp
            115                 120                 125

Gly Ala Thr Asp Tyr Tyr Gly Pro Gly Lys Thr Val Asp Thr Lys Gln
        130                 135                 140

Pro Met Thr Val Val Thr Gln Phe Ile Gly Asp Pro Leu Thr Glu Ile
145                 150                 155                 160

Lys Arg Val Tyr Val Gln Gly Gly Lys Val Ile Asn Asn Ser Lys Thr
                165                 170                 175

Ser Asn Leu Gly Ser Val Tyr Asp Ser Leu Thr Glu Ala Phe Cys Asp
            180                 185                 190

Asp Thr Lys Gln Val Thr Gly Asp Thr Asn Asp Phe Lys Ala Lys Gly
        195                 200                 205

Gly Met Ser Gly Phe Ser Lys Asn Leu Asp Thr Pro Gln Val Leu Val
    210                 215                 220

Met Ser Leu Trp Asp Asp His Thr Ala Asn Met Leu Trp Leu Asp Ser
225                 230                 235                 240

Thr Tyr Pro Thr Asp Ser Thr Lys Pro Gly Ala Ala Arg Gly Thr Cys
                245                 250                 255

Ala Val Thr Ser Gly Asp Pro Lys Asp Val Glu Ser Lys Gln Ala Asn
            260                 265                 270

Ser Gln Val Val Tyr Ser Asp Ile Lys Phe Gly Pro Ile Asn Ser Thr
        275                 280                 285

Tyr Lys Ala Asn
    290
```

<210> SEQ ID NO 32
<211> LENGTH: 318
<212> TYPE: PRT
<213> ORGANISM: Reticulitermes flavipes gut symbiont

<400> SEQUENCE: 32

```
Met Phe Lys Leu Lys Asn Lys Glu Phe Thr Phe Thr Thr Asp Val Ser
1               5                   10                  15

Gly Leu Pro Cys Gly Leu Asn Gly Ala Leu Tyr Phe Val Ala Met Asp
            20                  25                  30

Glu Asp Gly Gly Lys Ala Lys His Pro Leu Ser Lys Pro Gly Ala Lys
        35                  40                  45

Tyr Gly Met Gly Tyr Cys Asp Ala Gln Cys Pro His Asp Met Lys Phe
    50                  55                  60

Ile Glu Gly Leu Ala Asn Cys Glu Gly Trp Lys Pro Gln Asp Asn Asp
65                  70                  75                  80

Glu Asn Ser Gly Asn Gly Lys Tyr Gly Thr Cys Cys Ala Glu Met Asp
                85                  90                  95

Ile Trp Glu Ala Asn Ser Gln Ala Thr Ala Tyr Thr Val His Ala Cys
                100                 105                 110

Ser Lys Thr Gly Ala Thr Lys Trp Ser Gly Asn Asp Cys Gly Asp Asp
            115                 120                 125

Asp Asn Arg Tyr Asn Gly Ile Cys Asp Lys Asp Gly Cys Asp Tyr Asn
        130                 135                 140

Ser Trp Arg Leu Gly Asn Gln Thr Phe Phe Gly Pro Gly Leu Ile Val
145                 150                 155                 160

Asp Ser Ser Lys Pro Val Thr Val Val Thr Gln Phe Ile Thr Ser Asn
                165                 170                 175

Asn Gln Asp Ser Gly Glu Leu Val Glu Val Arg Arg Leu Tyr Val Gln
                180                 185                 190

Asn Asn Lys Val Ile Gln Asn Thr Val Thr Asn Ile Gln Gly Ile Lys
            195                 200                 205

Asn Ala Asp Ser Ile Thr Asp Ser Phe Cys Asp Thr Lys Ser Val
210                 215                 220

Phe Gly Asp Thr Asn Asp Tyr Lys Ala Lys Gly Ala Met Ala Gly Phe
225                 230                 235                 240

Ser Lys Ser Ile Asp Pro Gly Val Val Leu Val Arg Ser Leu Trp Asp
                245                 250                 255

Asp His Ser Val Asn Met Leu Trp Leu Asp Ser Thr Tyr Pro Thr Asp
                260                 265                 270

Ser Asn Lys Pro Gly Ala Ser Arg Gly Pro Cys Ala Ile Thr Ser Gly
            275                 280                 285

Lys Pro Ser Asp Val Glu Ser Gln Ser Ala Ser Ala Ser Val Lys Phe
        290                 295                 300

Ser Asp Ile Arg Phe Gly Pro Ile Asp Ser Thr Tyr Ser Lys
305                 310                 315

<210> SEQ ID NO 33
<211> LENGTH: 448
<212> TYPE: PRT
<213> ORGANISM: Mastotermes darwinensis

<400> SEQUENCE: 33

Met Arg Val Leu Leu Cys Leu Leu Ser Ala Phe Ala Leu Cys Gln Gly
1               5                   10                  15

Ala Tyr Asp Tyr Asn Asp Val Leu Thr Lys Ser Leu Leu Phe Tyr Glu
            20                  25                  30

Ala Gln Arg Ser Gly Lys Leu Pro Ser Asp Gln Lys Val Thr Trp Arg
        35                  40                  45

Lys Asp Ser Ala Leu Asn Asp Lys Gly Gln Asn Gly Glu Asp Leu Thr
    50                  55                  60
```

```
Gly Gly Tyr Tyr Asp Ala Gly Asp Tyr Val Lys Phe Gly Phe Pro Met
 65                  70                  75                  80

Ala Tyr Thr Ala Thr Val Leu Ala Trp Gly Leu Val Asp His Pro Ala
                 85                  90                  95

Gly Tyr Ser Ser Ala Gly Val Leu Asp Asp Gly Arg Lys Ala Val Lys
            100                 105                 110

Trp Val Thr Asp Tyr Leu Ile Lys Ala His Val Ser Lys Asn Glu Leu
        115                 120                 125

Tyr Gly Gln Val Gly Asp Gly Asp Ala Asp His Ala Tyr Trp Gly Arg
    130                 135                 140

Pro Glu Asp Met Thr Met Ala Arg Pro Ala Tyr Lys Ile Asp Thr Ser
145                 150                 155                 160

Arg Pro Gly Ser Asp Leu Ala Gly Glu Thr Ala Ala Ala Leu Ala Ala
                165                 170                 175

Ala Ser Ile Val Phe Lys Ser Thr Asp Ser Asn Tyr Ala Asn Thr Leu
            180                 185                 190

Leu Thr His Ala Lys Gln Leu Phe Asp Phe Ala Asn Asn Tyr Arg Gly
        195                 200                 205

Lys Tyr Ser Asp Ser Ile Thr Gln Ala Ser Asn Phe Tyr Ser Ser Ser
    210                 215                 220

Asp Tyr Lys Asp Glu Leu Val Trp Ala Ala Val Trp Leu Tyr Arg Ala
225                 230                 235                 240

Thr Asn Asp Gln Thr Tyr Leu Thr Thr Ala Glu Lys Leu Tyr Ser Asp
                245                 250                 255

Leu Gly Leu Gln Ser Trp Asn Gly Gly Phe Thr Trp Asp Thr Lys Ile
            260                 265                 270

Ser Gly Val Glu Val Leu Leu Ala Lys Ile Thr Gly Lys Gln Ala Tyr
        275                 280                 285

Lys Asp Lys Val Lys Gly Tyr Cys Asp Tyr Ile Ser Gly Ser Gln Gln
    290                 295                 300

Lys Thr Pro Lys Gly Leu Val Tyr Ile Asp Lys Trp Gly Ser Leu Arg
305                 310                 315                 320

Met Ala Ala Asn Ala Ala Tyr Ile Cys Ala Val Ala Ala Asp Val Gly
                325                 330                 335

Ile Ser Ser Thr Ala Tyr Arg Gln Phe Ala Lys Thr Gln Ile Asn Tyr
            340                 345                 350

Ile Leu Gly Asp Ala Gly Arg Ser Phe Val Val Gly Tyr Gly Asn Asn
        355                 360                 365

Pro Pro Thr His Pro His Arg Ser Ser Cys Pro Asp Ala Pro
    370                 375                 380         Pro
                                                        385...

Ala Thr Cys Asp Trp Asn Asn Tyr Asn Ser Ala Asn Pro Asn Pro His
385                 390                 395                 400

Val Leu Tyr Gly Ala Leu Val Gly Gly Pro Asp Ser Asn Asp Asn Tyr
                405                 410                 415

Gln Asp Leu Arg Ser Asp Tyr Val Ala Asn Glu Val Ala Thr Asp Tyr
            420                 425                 430

Asn Ala Ala Phe Gln Ser Leu Leu Ala Leu Ile Val Asp Leu Gly Leu
        435                 440                 445

<210> SEQ ID NO 34
<211> LENGTH: 448
<212> TYPE: PRT
<213> ORGANISM: Reticulitermes flavipes

<400> SEQUENCE: 34
```

-continued

```
Met Lys Val Phe Val Cys Leu Leu Ser Ala Leu Ala Leu Cys Gln Ala
 1               5                  10                  15

Ala Tyr Asp Tyr Lys Thr Val Leu Ser Asn Ser Leu Leu Phe Tyr Glu
            20                  25                  30

Ala Gln Arg Ser Gly Lys Leu Pro Ser Asp Gln Lys Val Thr Trp Arg
        35                  40                  45

Lys Asp Ser Ala Leu Asn Asp Lys Gly Gln Lys Gly Glu Asp Leu Thr
    50                  55                  60

Gly Gly Tyr Tyr Asp Ala Gly Asp Phe Val Lys Phe Gly Phe Pro Met
 65                  70                  75                  80

Ala Tyr Thr Val Thr Val Leu Ala Trp Gly Val Ile Asp Tyr Glu Ser
                85                  90                  95

Ala Tyr Ser Ala Ala Gly Ala Leu Asp Ser Gly Arg Lys Ala Leu Lys
            100                 105                 110

Tyr Gly Thr Asp Tyr Phe Leu Lys Ala His Thr Ala Ala Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ala Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255

Phe Gly Leu Gly Asn Trp Asn Gly Ala Phe Asn Trp Asp Asn Lys Ile
            260                 265                 270

Ser Gly Val Gln Val Leu Leu Ala Lys Leu Thr Ser Lys Gln Ala Tyr
        275                 280                 285

Lys Asp Lys Val Gln Gly Tyr Val Asp Tyr Leu Ile Ser Gln Lys
    290                 295                 300

Lys Thr Pro Lys Gly Leu Val Tyr Ile Asp Gln Trp Gly Thr Leu Arg
305                 310                 315                 320

His Ala Ala Asn Ser Ala Leu Ile Ala Leu Gln Ala Ala Asp Leu Gly
                325                 330                 335

Ile Asn Ala Ala Thr Tyr Arg Ala Tyr Ala Lys Lys Gln Ile Asp Tyr
            340                 345                 350

Ala Leu Gly Asp Gly Gly Arg Ser Tyr Val Val Gly Phe Gly Thr Asn
        355                 360                 365

Pro Pro Val Arg Pro His His Arg Ser Ser Cys Pro Asp Ala Pro
370                 375                 380

Ala Val Cys Asp Trp Asn Thr Tyr Asn Ser Ala Gly Pro Asn Ala His
385                 390                 395                 400

Val Leu Thr Gly Ala Leu Val Gly Gly Pro Asp Ser Asn Asp Ser Tyr
                405                 410                 415

Thr Asp Ala Arg Ser Asp Tyr Ile Ser Asn Glu Val Ala Thr Asp Tyr
            420                 425                 430
```

```
Asn Ala Gly Phe Gln Ser Ala Val Ala Gly Leu Leu Lys Ala Gly Val
            435                 440                 445

<210> SEQ ID NO 35
<211> LENGTH: 448
<212> TYPE: PRT
<213> ORGANISM: Reticulitermes speratus

<400> SEQUENCE: 35

Met Lys Val Phe Val Cys Leu Leu Ser Ala Leu Ala Leu Cys Gln Ala
1               5                   10                  15

Ala Tyr Asp Tyr Lys Thr Val Leu Ser Asn Ser Leu Leu Phe Tyr Glu
            20                  25                  30

Ala Gln Arg Ser Gly Lys Leu Pro Ser Asp Gln Lys Val Thr Trp Arg
        35                  40                  45

Lys Asp Ser Ala Leu Asn Asp Lys Gly Gln Lys Gly Glu Asp Leu Thr
    50                  55                  60

Gly Gly Tyr Tyr Asp Ala Gly Asp Phe Val Lys Phe Gly Phe Pro Met
65                  70                  75                  80

Ala Tyr Thr Val Thr Val Leu Ala Trp Gly Val Ile Asp Tyr Glu Ser
                85                  90                  95

Ala Tyr Ser Ala Ala Gly Ala Leu Asp Ser Gly Arg Lys Ala Leu Lys
            100                 105                 110

Tyr Gly Thr Asp Tyr Phe Leu Lys Ala His Thr Ala Ala Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ala Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255

Phe Gly Leu Gly Asn Phe Asn Gly Ala Phe Asn Trp Asp Asn Lys Val
            260                 265                 270

Ser Gly Val Gln Val Leu Leu Ala Lys Leu Thr Ser Lys Gln Val Tyr
        275                 280                 285

Lys Asp Lys Val Gln Ser Tyr Val Asp Tyr Leu Ile Ser Ser Gln Lys
    290                 295                 300

Lys Thr Pro Lys Gly Leu Val Tyr Ile Asp Gln Trp Gly Thr Leu Arg
305                 310                 315                 320

His Ala Ala Asn Ser Ala Leu Ile Ala Leu Gln Ala Ala Asp Leu Gly
                325                 330                 335

Ile Asn Ala Ala Thr Tyr Arg Ala Tyr Ala Lys Lys Gln Ile Asp Tyr
            340                 345                 350

Ala Leu Gly Asp Gly Gly Arg Ser Tyr Val Ile Gly Phe Gly Thr Asn
        355                 360                 365
```

```
Pro Pro Val Arg Pro His His Arg Ser Ser Ser Cys Pro Asp Ala Pro
    370                 375                 380

Ala Val Cys Asp Trp Asn Thr Tyr Asn Ser Ala Gly Pro Asn Ala His
385                 390                 395                 400

Val Leu Thr Gly Ala Leu Val Gly Gly Pro Ser Asn Asp Ser Tyr
                405                 410                 415

Thr Asp Ala Arg Ser Asp Tyr Ile Ser Asn Glu Val Ala Thr Asp Tyr
            420                 425                 430

Asn Ala Gly Phe Gln Ser Ala Val Ala Gly Leu Leu Lys Ala Gly Val
            435                 440                 445

<210> SEQ ID NO 36
<211> LENGTH: 448
<212> TYPE: PRT
<213> ORGANISM: Coptotermes formosanus

<400> SEQUENCE: 36

Met Arg Val Phe Val Cys Leu Leu Ser Ala Leu Ala Leu Cys Gln Ala
1               5                   10                  15

Ala Tyr Asp Tyr Lys Thr Val Leu Lys Asn Ser Leu Leu Phe Tyr Glu
            20                  25                  30

Ala Gln Arg Ser Gly Lys Leu Pro Ala Asp Gln Lys Val Thr Trp Arg
        35                  40                  45

Lys Asp Ser Ala Leu Asn Asp Lys Gly Gln Lys Gly Glu Asp Leu Thr
50                  55                  60

Gly Gly Tyr Tyr Asp Ala Gly Asp Phe Val Lys Phe Gly Phe Pro Met
65                  70                  75                  80

Ala Tyr Thr Val Thr Val Leu Ala Trp Gly Leu Val Asp Tyr Glu Ser
            85                  90                  95

Ala Tyr Ser Thr Ala Gly Ala Leu Asp Asp Gly Arg Lys Ala Leu Lys
        100                 105                 110

Trp Gly Thr Asp Tyr Phe Leu Lys Ala His Thr Ala Ala Asn Glu Phe
    115                 120                 125

Tyr Gly Gln Val Gly Gln Gly Asp Val Asp His Ala Tyr Trp Gly Arg
    130                 135                 140

Pro Glu Asp Met Thr Met Ser Arg Pro Ala Tyr Lys Ile Asp Thr Ser
145                 150                 155                 160

Lys Pro Gly Ser Asp Leu Ala Ala Glu Thr Ala Ala Ala Leu Ala Ala
                165                 170                 175

Thr Ala Ile Ala Tyr Lys Ser Ala Asp Ser Thr Tyr Ser Asn Asn Leu
            180                 185                 190

Ile Thr His Ala Lys Gln Leu Phe Asp Phe Ala Asn Asn Tyr Arg Gly
        195                 200                 205

Lys Tyr Ser Asp Ser Ile Thr Asp Ala Lys Asn Phe Tyr Ala Ser Gly
    210                 215                 220

Asp Tyr Lys Asp Glu Leu Val Trp Ala Ala Ala Trp Leu Tyr Arg Ala
225                 230                 235                 240

Thr Asn Asp Asn Thr Tyr Leu Thr Lys Ala Glu Ser Leu Tyr Asn Glu
                245                 250                 255

Phe Gly Leu Gly Ser Trp Asn Gly Ala Phe Asn Trp Asp Asn Lys Ile
            260                 265                 270

Ser Gly Val Gln Val Leu Leu Ala Lys Leu Thr Ser Lys Gln Ala Tyr
        275                 280                 285

Lys Asp Lys Val Gln Gly Tyr Val Asp Tyr Leu Val Ser Ser Gln Lys
    290                 295                 300
```

```
Lys Thr Pro Lys Gly Leu Val Tyr Ile Asp Gln Trp Gly Thr Leu Arg
305                 310                 315                 320

His Ala Ala Asn Ser Ala Leu Ile Ala Leu Gln Ala Ala Asp Leu Gly
                325                 330                 335

Ile Asn Ala Ala Ser Tyr Arg Gln Tyr Ala Lys Lys Gln Ile Asp Tyr
            340                 345                 350

Ala Leu Gly Asp Gly Gly Arg Ser Tyr Val Val Gly Phe Gly Thr Asn
        355                 360                 365

Pro Pro Val Arg Pro His His Arg Ser Ser Cys Pro Asp Ala Pro
    370                 375                 380

Ala Ala Cys Asp Trp Asn Thr Tyr Asn Ser Ala Gly Pro Asn Ala His
385                 390                 395                 400

Val Leu Thr Gly Ala Leu Val Gly Gly Pro Asp Ser Asn Asp Ser Tyr
                405                 410                 415

Thr Asp Ser Arg Ser Asp Tyr Ile Ser Asn Glu Val Ala Thr Asp Tyr
            420                 425                 430

Asn Ala Gly Phe Gln Ser Ala Val Ala Gly Leu Leu Lys Ala Gly Val
        435                 440                 445

<210> SEQ ID NO 37
<211> LENGTH: 448
<212> TYPE: PRT
<213> ORGANISM: Coptotermes acinaciformis

<400> SEQUENCE: 37

Met Arg Val Phe Val Cys Leu Leu Ser Ala Leu Ala Leu Cys Gln Ala
1               5                   10                  15

Ala Tyr Asp Tyr Thr Thr Val Leu Lys Ser Ser Leu Leu Phe Tyr Glu
            20                  25                  30

Ala Gln Arg Ser Gly Lys Leu Pro Ala Asp Gln Lys Val Thr Trp Arg
        35                  40                  45

Lys Asp Ser Ala Leu Asp Asp Lys Gly Asn Asn Gly Glu Asp Leu Thr
    50                  55                  60

Gly Gly Tyr Tyr Asp Ala Gly Asp Phe Val Lys Phe Gly Phe Pro Leu
65                  70                  75                  80

Ala Tyr Thr Ala Thr Val Leu Ala Trp Gly Leu Val Asp Tyr Glu Ala
                85                  90                  95

Gly Tyr Ser Ser Ala Gly Ala Thr Asp Asp Gly Arg Lys Ala Val Lys
            100                 105                 110

Trp Ala Thr Asp Tyr Leu Leu Lys Ala His Thr Ala Ala Thr Glu Leu
        115                 120                 125

Tyr Gly Gln Val Gly Asp Gly Asp Ala Asp His Ala Tyr Trp Gly Arg
    130                 135                 140

Pro Glu Asp Met Thr Met Ala Arg Pro Ala Tyr Lys Ile Asp Ala Ser
145                 150                 155                 160

Arg Pro Gly Ser Asp Leu Ala Gly Glu Thr Ala Ala Leu Ala Ala
                165                 170                 175

Ala Ser Ile Val Phe Lys Gly Val Asp Ser Ser Tyr Ser Asp Asn Leu
            180                 185                 190

Leu Ala His Ala Lys Gln Leu Phe Asp Phe Ala Asp Asn Tyr Arg Gly
        195                 200                 205

Lys Tyr Ser Asp Ser Ile Thr Gln Ala Ser Asn Phe Tyr Ala Ser Gly
    210                 215                 220

Asp Tyr Lys Asp Glu Leu Val Trp Ala Ala Thr Trp Leu Tyr Arg Ala
225                 230                 235                 240
```

Thr Asn Asp Asn Thr Tyr Leu Thr Lys Ala Glu Ser Leu Tyr Asn Glu
            245                 250                 255

Phe Gly Leu Gly Asn Trp Asn Gly Ala Phe Asn Trp Asp Asn Lys Val
        260                 265                 270

Ser Gly Val Gln Val Leu Leu Ala Lys Leu Thr Ser Lys Gln Ala Tyr
    275                 280                 285

Lys Asp Thr Val Gln Gly Tyr Val Asp Tyr Leu Ile Asn Asn Gln Gln
290                 295                 300

Lys Thr Pro Lys Gly Leu Leu Tyr Ile Asp Gln Trp Gly Thr Leu Arg
305                 310                 315                 320

His Ala Ala Asn Ala Ala Leu Ile Ile Leu Gln Ala Ala Asp Leu Gly
                325                 330                 335

Ile Ser Ala Asp Ser Tyr Arg Gln Phe Ala Lys Lys Gln Ile Asp Tyr
            340                 345                 350

Ala Leu Gly Asp Gly Gly Arg Ser Tyr Val Val Gly Phe Gly Asp Asn
        355                 360                 365

Pro Pro Thr His Pro His His Arg Ser Ser Ser Cys Pro Asp Ala Pro
    370                 375                 380

Ala Val Cys Asp Trp Asn Thr Phe Asn Ser Pro Asp Pro Asn Phe His
385                 390                 395                 400

Val Leu Thr Gly Ala Leu Val Gly Gly Pro Asp Gln Asn Asp Asn Tyr
                405                 410                 415

Val Asp Asp Arg Ser Asp Tyr Val Ser Asn Glu Val Ala Thr Asp Tyr
            420                 425                 430

Asn Ala Gly Phe Gln Ser Ala Val Ala Leu Val Thr Leu Gly Val
        435                 440                 445

<210> SEQ ID NO 38
<211> LENGTH: 448
<212> TYPE: PRT
<213> ORGANISM: Nasutitermes walkeri

<400> SEQUENCE: 38

Met Arg Val Phe Leu Cys Leu Leu Ser Ala Leu Ala Leu Cys Gln Ala
1               5                   10                  15

Ala Tyr Asp Tyr Lys Gln Val Leu Arg Asp Ser Leu Leu Phe Tyr Glu
            20                  25                  30

Ala Gln Arg Ser Gly Arg Leu Pro Ala Asp Gln Lys Val Thr Trp Arg
        35                  40                  45

Lys Asp Ser Ala Leu Asn Asp Gln Gly Glu Gln Gly Gln Asp Leu Thr
    50                  55                  60

Gly Gly Tyr Phe Asp Ala Gly Asp Phe Val Lys Phe Gly Phe Pro Met
65                  70                  75                  80

Ala Tyr Thr Ala Thr Val Leu Ala Trp Gly Leu Ile Asp Phe Glu Ala
                85                  90                  95

Gly Tyr Ser Ser Ala Gly Ala Leu Asp Asp Gly Arg Lys Ala Val Lys
            100                 105                 110

Trp Ala Thr Asp Tyr Phe Ile Lys Ala His Thr Ser Gln Asn Glu Phe
        115                 120                 125

Tyr Gly Gln Val Gly Gln Gly Asp Val Asp His Ala Tyr Trp Gly Arg
    130                 135                 140

Pro Glu Asp Met Thr Met Ala Arg Pro Ala Tyr Lys Ile Asp Thr Ser
145                 150                 155                 160

Arg Pro Gly Ser Asp Leu Ala Gly Glu Thr Ala Ala Ala Leu Ala Ala
                165                 170                 175

```
Ala Ser Ile Val Phe Lys Asn Val Asp Gly Thr Tyr Ser Asn Asn Leu
            180                 185                 190

Leu Thr His Ala Arg Gln Leu Phe Asp Phe Ala Asn Asn Tyr Arg Gly
            195                 200                 205

Lys Tyr Ser Asp Ser Ile Thr Asp Ala Arg Asn Phe Tyr Ala Ser Ala
            210                 215                 220

Asp Tyr Arg Asp Glu Leu Val Trp Ala Ala Trp Leu Tyr Arg Ala
225                 230                 235                 240

Thr Asn Asp Asn Ser Tyr Leu Asn Thr Ala Glu Ser Leu Tyr Asn Glu
            245                 250                 255

Phe Gly Leu Gln Asn Trp Gly Gly Leu Asn Trp Asp Ser Lys Val
            260                 265                 270

Ser Gly Val Gln Val Leu Leu Ala Lys Leu Thr Asn Lys Gln Glu Tyr
            275                 280                 285

Lys Asp Thr Ile Gln Ser Tyr Val Asn Tyr Leu Ile Asn Asn Gln Gln
            290                 295                 300

Lys Thr Pro Lys Gly Leu Leu Tyr Ile Asp Met Trp Gly Thr Leu Arg
305                 310                 315                 320

His Ala Ala Asn Ala Ala Phe Ile Met Leu Glu Ala Ala Asp Leu Gly
            325                 330                 335

Leu Ser Ala Ser Ser Tyr Arg Gln Phe Ala Gln Thr Gln Ile Asp Tyr
            340                 345                 350

Ala Leu Gly Asp Gly Gly Arg Ser Phe Val Cys Gly Phe Gly Ser Asn
            355                 360                 365

Pro Pro Thr Arg Pro His His Arg Ser Ser Ser Cys Pro Pro Ala Pro
370                 375                 380

Ala Thr Cys Asp Trp Asn Thr Phe Asn Ser Pro Asp Pro Asn Tyr Asn
385                 390                 395                 400

Val Leu Ser Gly Ala Leu Val Gly Gly Pro Asp Gln Asn Asp Asn Tyr
            405                 410                 415

Val Asp Asp Arg Ser Asp Tyr Val His Asn Glu Val Ala Thr Asp Tyr
            420                 425                 430

Asn Ala Gly Phe Gln Ser Ala Leu Ala Ala Leu Val Ala Leu Gly Tyr
            435                 440                 445

<210> SEQ ID NO 39
<211> LENGTH: 448
<212> TYPE: PRT
<213> ORGANISM: Nasutitermes takasagoensis

<400> SEQUENCE: 39

Met Arg Val Phe Leu Cys Leu Leu Ser Ala Leu Ala Leu Cys Gln Ala
1               5                   10                  15

Ala Tyr Asp Tyr Lys Gln Val Leu Arg Asp Ser Leu Leu Phe Tyr Glu
            20                  25                  30

Ala Gln Arg Ser Gly Arg Leu Pro Ala Asp Gln Lys Val Thr Trp Arg
        35                  40                  45

Lys Asp Ser Ala Leu Asn Asp Gln Gly Asp Gln Gly Gln Asp Leu Thr
    50                  55                  60

Gly Gly Tyr Phe Asp Ala Gly Asp Phe Val Lys Phe Gly Phe Pro Met
65                  70                  75                  80

Ala Tyr Thr Ala Thr Val Leu Ala Trp Gly Leu Ile Asp Phe Glu Ala
                85                  90                  95

Gly Tyr Ser Ser Ala Gly Ala Leu Asp Asp Gly Arg Lys Ala Val Lys
            100                 105                 110
```

Trp Ala Thr Asp Tyr Phe Ile Lys Ala His Thr Ser Gln Asn Glu Phe
            115                 120                 125

Tyr Gly Gln Val Gly Gln Gly Asp Ala Asp His Ala Phe Trp Gly Arg
        130                 135                 140

Pro Glu Asp Met Thr Met Ala Arg Pro Ala Tyr Lys Ile Asp Thr Ser
145                 150                 155                 160

Arg Pro Gly Ser Asp Leu Ala Gly Glu Thr Ala Ala Leu Ala Ala
                165                 170                 175

Ala Ser Ile Val Phe Arg Asn Val Asp Gly Thr Tyr Ser Asn Asn Leu
                180                 185                 190

Leu Thr His Ala Arg Gln Leu Phe Asp Phe Ala Asn Asn Tyr Arg Gly
            195                 200                 205

Lys Tyr Ser Asp Ser Ile Thr Asp Ala Arg Asn Phe Tyr Ala Ser Ala
        210                 215                 220

Asp Tyr Arg Asp Glu Leu Val Trp Ala Ala Trp Leu Tyr Arg Ala
225                 230                 235                 240

Thr Asn Asp Asn Thr Tyr Leu Asn Thr Ala Glu Ser Leu Tyr Asp Glu
                245                 250                 255

Phe Gly Leu Gln Asn Trp Gly Gly Leu Asn Trp Asp Ser Lys Val
            260                 265                 270

Ser Gly Val Gln Val Leu Leu Ala Lys Leu Thr Asn Lys Gln Ala Tyr
        275                 280                 285

Lys Asp Thr Val Gln Ser Tyr Val Asn Tyr Leu Ile Asn Asn Gln Gln
    290                 295                 300

Lys Thr Pro Lys Gly Leu Leu Tyr Ile Asp Met Trp Gly Thr Leu Arg
305                 310                 315                 320

His Ala Asn Ala Ala Phe Ile Met Leu Glu Ala Ala Glu Leu Gly
                325                 330                 335

Leu Ser Ala Ser Ser Tyr Arg Gln Phe Ala Gln Thr Gln Ile Asp Tyr
            340                 345                 350

Ala Leu Gly Asp Gly Gly Arg Ser Phe Val Cys Gly Phe Gly Ser Asn
        355                 360                 365

Pro Pro Thr Arg Pro His His Arg Ser Ser Ser Cys Pro Pro Ala Pro
370                 375                 380

Ala Thr Cys Asp Trp Asn Thr Phe Asn Ser Pro Asp Pro Asn Tyr His
385                 390                 395                 400

Val Leu Ser Gly Ala Leu Val Gly Gly Pro Asp Gln Asn Asp Asn Tyr
                405                 410                 415

Val Asp Asp Arg Ser Asp Tyr Val His Asn Glu Val Ala Thr Asp Tyr
            420                 425                 430

Asn Ala Gly Phe Gln Ser Ala Leu Ala Ala Leu Val Ala Leu Gly Tyr
        435                 440                 445

<210> SEQ ID NO 40
<211> LENGTH: 447
<212> TYPE: PRT
<213> ORGANISM: Panesthia cribrata

<400> SEQUENCE: 40

Met Lys Ile Ile Leu Leu Phe Leu Gly Gly Leu Ala Leu Cys Gln Gly
1               5                   10                  15

Ala Thr Tyr Asp Tyr Ser Gln Leu Ile Gln Tyr Ser Leu Leu Phe Tyr
                20                  25                  30

Glu Ala Gln Arg Ser Gly Lys Leu Pro Ala Asp Gln Lys Val Thr Trp
            35                  40                  45

```
Arg Lys Asp Ser Ala Leu Asn Asp Lys Gly Gln Asn Gly Glu Asp Leu
     50                  55                  60

Thr Gly Gly Tyr Tyr Asp Ala Gly Asp Tyr Val Lys Phe Gly Tyr Pro
 65                  70                  75                  80

Met Ala Phe Thr Ala Thr Leu Leu Ala Trp Ser Leu Ile Asp Tyr Glu
                 85                  90                  95

Gln Gly Tyr Ala Lys Ala Asn Ser Val Glu Asp Ala Arg Lys Ala Val
                100                 105                 110

Lys Trp Ala Thr Asp Tyr Phe Leu Lys Ala His Val Ser Glu His Glu
                115                 120                 125

Phe Tyr Gly Gln Val Gly Glu Gly Asn Leu Asp His Asn Ser Trp Gly
                130                 135                 140

Arg Pro Glu Asp Met Thr Met Glu Arg Pro Ala Tyr Lys Ile Asp Glu
145                 150                 155                 160

Gln Asn Pro Gly Thr Glu Leu Ala Ala Glu Thr Ala Ala Ala Leu Ala
                165                 170                 175

Ala Ala Ser Ile Val Phe Lys Ser Val Asp Pro Ser Tyr Ser Asn Thr
                180                 185                 190

Leu Leu Thr His Ala Lys Gln Leu Tyr Asp Phe Gly Asp Asn Phe Arg
                195                 200                 205

Gly Lys Tyr Ser Glu Ser Ile Asn Asp Ala Gln Gln Phe Tyr Arg Ser
                210                 215                 220

Asn Glu Phe Glu Asp Glu Leu Val Trp Gly Ala Leu Trp Leu Tyr Lys
225                 230                 235                 240

Ala Thr Met Asp Glu Ser Phe Leu Thr Lys Ala Gln Gln Tyr Tyr Asp
                245                 250                 255

Asp Phe Gly Ile Ala Glu Tyr Asn Pro Trp Phe Ser Trp Asp Gln Lys
                260                 265                 270

Cys Thr Ser Ser Gln Leu Leu Leu Ala Gln Ile Thr Gln Glu Gln Gln
                275                 280                 285

Tyr Ile Asp Lys Ile Thr Ala Tyr Cys Asp His Met Ile Ser Gly Gln
                290                 295                 300

Gln Arg Thr Pro Lys Gly Leu Val Tyr Ile Asp Thr Trp Gly Ser Leu
305                 310                 315                 320

Arg Met Ala Ala Asn Ala Ala Tyr Leu Cys Leu Glu Ala Ala Ser Ala
                325                 330                 335

Gly Leu Lys Pro Thr Glu Tyr Arg Ala Phe Ala Thr Glu Gln Ile Gly
                340                 345                 350

Tyr Ala Leu Gly Asp Thr Gly Lys Ser Phe Val Val Gly Phe Gly Val
                355                 360                 365

Asn Pro Pro Ser His Glu Ser His Arg Ser Ser Cys Pro Asp Ala
                370                 375                 380

Pro Ala Pro Cys Asp Trp Val Thr Tyr Gly Ser Val Asp Pro Asn Pro
385                 390                 395                 400

His Val Leu Tyr Gly Ala Ile Val Gly Gly Pro Gly Pro Asn Asp Glu
                405                 410                 415

Tyr Asp Asp Gln Arg Tyr Asp Tyr Val His Asn Glu Val Ala Asp Asp
                420                 425                 430

Tyr Asn Ala Gly Tyr Gln Gly Cys Leu Ala Ala Leu Asn Glu Leu
                435                 440                 445

<210> SEQ ID NO 41
<211> LENGTH: 33
<212> TYPE: PRT
```

<213> ORGANISM: T. reesei

<400> SEQUENCE: 41

His Tyr Gly Gln Cys Gly Gly Ile Gly Tyr Ser Gly Pro Thr Val Cys
1               5                   10                  15

Ala Ser Gly Thr Thr Cys Gln Val Leu Asn Pro Tyr Tyr Ser Gln Cys
            20                  25                  30

Leu

<210> SEQ ID NO 42
<211> LENGTH: 32
<212> TYPE: PRT
<213> ORGANISM: T. reesei

<400> SEQUENCE: 42

Val Tyr Ser Asn Asp Tyr Tyr Ser Gln Cys Leu Pro Gly Ala Ala Ser
1               5                   10                  15

Ser Ser Ser Ser Thr Arg Ala Ala Ser Thr Thr Ser Arg Val Ser Pro
            20                  25                  30

<210> SEQ ID NO 43
<211> LENGTH: 19
<212> TYPE: PRT
<213> ORGANISM: S. cerevisiae

<400> SEQUENCE: 43

Met Arg Phe Pro Ser Ile Phe Thr Ala Val Leu Phe Ala Ala Ser Ser
1               5                   10                  15

Ala Leu Ala

<210> SEQ ID NO 44
<211> LENGTH: 546
<212> TYPE: PRT
<213> ORGANISM: Schizochytrium aggregatum

<400> SEQUENCE: 44

Met Ser Ala Ile Thr Leu Ala Leu Gly Ala Leu Ala Leu Ser Ser Val
1               5                   10                  15

Val Asn Ala Gln Gln Ala Gly Thr Leu Thr Pro Glu Lys His Pro Ala
            20                  25                  30

Phe Ser Val Ser Thr Cys Ser Ala Gly Gly Thr Cys Thr Ser Lys Thr
        35                  40                  45

Gln Ser Ile Val Leu Asp Gly Asn Trp Arg Trp Leu His Ser Thr Ser
    50                  55                  60

Gly Ser Thr Asn Cys Tyr Thr Gly Asn Thr Phe Asp Lys Thr Leu Cys
65                  70                  75                  80

Pro Asp Gly Val Thr Cys Ala Ala Asn Cys Ala Leu Asp Gly Ala Asp
                85                  90                  95

Tyr Thr Gly Thr Tyr Gly Ile Lys Ala Ser Gly Asn Ser Leu Ser Leu
            100                 105                 110

Gln Leu Lys Thr Gly Ser Asn Val Gly Ser Arg Val Tyr Leu Met Asp
        115                 120                 125

Glu Gln Asp Lys Asn Tyr Gln Leu Phe Asn Leu Lys Asn Gln Glu Phe
    130                 135                 140

Thr Phe Asp Val Asp Val Ser Lys Ile Gly Cys Gly Leu Asn Gly Ala
145                 150                 155                 160

Leu Tyr Phe Val Ser Met Pro Ala Asp Gly Gly Leu Ser Thr Thr Asn
                165                 170                 175

```
Lys Ala Gly Thr Lys Phe Gly Thr Gly Tyr Cys Asp Ala Gln Cys Pro
            180                 185                 190
Lys Asp Ile Lys Phe Ile Lys Gly Lys Ala Asn Ser Asp Gly Trp Thr
        195                 200                 205
Ala Ser Ser Asn Asn Ala Asn Thr Gly Phe Gly Thr Thr Gly Ser Cys
    210                 215                 220
Cys Asn Glu Met Asp Ile Trp Glu Ala Asn Gly Ile Ser Asn Ala Val
225                 230                 235                 240
Thr Pro His Ser Cys Ser Pro Gly Asn Ala Ala Cys Thr Ser Asp Thr
                245                 250                 255
Thr Cys Gly Ser Gly Asp Gly Asn Arg Tyr Lys Gly Tyr Cys Asp Lys
            260                 265                 270
Asp Gly Cys Asp Phe Asn Pro Phe Arg Met Gly Asn Gln Thr Phe Tyr
        275                 280                 285
Gly Pro Gly Lys Thr Ile Asp Thr Thr Lys Pro Leu Thr Val Val Thr
    290                 295                 300
Gln Phe Ile Thr Ser Asp Asn Thr Ala Ser Gly Asp Leu Val Glu Ile
305                 310                 315                 320
Arg Arg Lys Tyr Val Gln Gly Gly Lys Val Phe Asp Gln Pro Thr Ser
                325                 330                 335
Asn Val Ala Gly Val Ser Gly Asn Ser Ile Thr Asp Thr Phe Cys Lys
            340                 345                 350
Asn Gln Lys Ser Val Phe Gly Asp Thr Asn Asp Phe Ala Ala Lys Gly
        355                 360                 365
Gly Leu Lys Ala Met Gly Asp Ala Phe Ala Asp Gly Met Val Leu Val
    370                 375                 380
Met Ser Leu Trp Asp Asp Tyr Asp Val Asn Met His Trp Leu Asn Ser
385                 390                 395                 400
Pro Tyr Pro Thr Asp Ala Asp Pro Thr Lys Pro Gly Val Ala Arg Gly
                405                 410                 415
Thr Cys Ser Ile Thr Ser Gly Lys Pro Ala Asp Val Glu Ser Gln Thr
            420                 425                 430
Pro Gly Ala Thr Val Val Tyr Ser Asn Ile Lys Thr Gly Pro Ile Gly
        435                 440                 445
Ser Thr Phe Ser Gly Ala Gln Gln Pro Gly Pro Gly Ser Gly Ser
    450                 455                 460
Ser Ser Ser Ser Ser Ala Gly Gly Ser Ser Thr Ser Arg Ser Ser
465                 470                 475                 480
Ser Thr Thr Ser Arg Ala Thr Thr Thr Ser Val Gly Thr Thr Thr Thr
                485                 490                 495
Thr Thr Ser Ser Arg Thr Thr Thr Thr Ser Ala Ala Gly Gly Val Val
            500                 505                 510
Gln Lys Tyr Gly Gln Cys Gly Gly Leu Thr Tyr Thr Gly Pro Thr Thr
        515                 520                 525
Cys Val Ser Gly Thr Thr Cys Thr Lys Ala Asn Asp Tyr Tyr Ser Gln
    530                 535                 540
Cys Leu
545

<210> SEQ ID NO 45
<211> LENGTH: 1638
<212> TYPE: DNA
<213> ORGANISM: Schizochytrium aggregatum

<400> SEQUENCE: 45
```

```
atgtctgcca ttaccctcgc cctgggtgct cttgccctca gctctgttgt caacgctcag    60
caggctggaa cccttactcc tgaaaaacac cctgctttt ctgtgtctac ttgctctgcc    120
ggcggcactt gcacgtccaa gacccagagc attgtgctcg atggcaactg gcgctggctc    180
cactctactt ccggctccac caactgctac acaggtaaca ccttcgacaa gactttgtgc    240
cctgatggag tgacttgcgc cgcaaactgc gccctcgatg gtgctgacta caccggcact    300
tacggtatca aggcatccgg caactctctg agccttcagc tcaagactgg cagcaacgtt    360
ggctccagag tctacctcat ggacgagcag gacaagaact accagctctt caacctgaag    420
aaccaggagt ttacgttcga cgtcgacgtc agcaagatcg gatgtggtct caacggcgct    480
ctgtacttcg tgtccatgcc cgcagatggt ggactttcta ccactaacaa ggccggcacc    540
aagttcggaa caggatattg tgatgctcag tgtcctaaag acatcaagtt tatcaagggc    600
aaggcaaaca gcgatggctg gacagcatct tccaacaacg caaacaccgg tttcggtacg    660
accggctcct gctgcaacga gatggatatc tgggaggcaa acgggatctc caacgctgtg    720
actcctcact cctgcagtcc cggcaacgcc gcttgcactt ctgacacaac ttgtggctct    780
ggcgacggta accgctacaa aggctactgt gacaaggacg gttgcgattt caaccccttc    840
aggatgggca accagacctt ctacggcccc ggcaagacta tcgacaccac caagcctctc    900
actgtggtca cccaattcat tacctctgac aacactgcta gtggcgatct tgttgagatc    960
cgtcgcaagt acgtccaggg cggcaaggtc ttcgatcagc ccacatccaa cgttgctggc    1020
gttagcggca actcgatcac cgacaccttc tgcaaaaacc agaagtccgt cttcggtgac    1080
actaacgact tcgctgcgaa gggtggcttg aaggctatgg gcgacgcctt cgctgatggc    1140
atggtccttg tcatgtctct gtgggatgat tacgatgtca acatgcactg gctcaactct    1200
ccttacccaa ctgacgccga cccaacaaag cctggtgttg cccgtggaac ttgctctatc    1260
acctctggta agcccgccga cgtcgagagc cagactcctg gtgccaccgt tgtctactcg    1320
aacatcaaga ctggtcccat tggctccacc ttctctggcg cccaacagcc cggtggcccc    1380
ggcagtggtt cttcatcttc cagctcagcg ggaggctcaa gcaccacctc caggtcttct    1440
tctaccacct ccagggctac caccacgagt gtcgggacca ctaccaccac cactagctctc    1500 cgcacgacca caaccagcgc tgctggcggc gtcgtccaga agtacggaca gtgcggtggc    1560
ctgacataca ctggtcctac tacttgtgtg agcggaacca cttgcaccaa ggccaacgac    1620
tactactcgc agtgcttg                                                  1638
```

<210> SEQ ID NO 46
<211> LENGTH: 1641
<212> TYPE: DNA
<213> ORGANISM: Artificial
<220> FEATURE:
<223> OTHER INFORMATION: Synthetic Schizochytrium aggregatum oligonucleotide

<400> SEQUENCE: 46

```
atgagatttc catctatttt cactgctgtt ttgttcgcag cctcatcgag tctagctcaa    60
caggccggta ctctaacgcc tgagaaacat cccgccttct ccgttagtac atgttccgct    120
ggaggcacgt gcactagtaa gacacaaagc atagtcttag atggcaactg gagatggctt    180
cacagcacat ccggttcaac gaactgttat actggcaata cattcgacaa gacgctttgt    240
cccgatggtg tcacttgtgc cgctaattgt gctttggacg gtgcagacta taccggaacg    300
tatggcataa aggcttcagg aaattcctta tccctacagc ttaaaactgg aagtaatgtg    360
ggttctagag tttacttgat ggacgagcaa gataagaatt atcaattatt caacttgaag    420
```

```
aatcaggagt tcactttga tgtagacgtg tcaaagatcg gctgtggttt aaacggcgcc    480
ttgtacttcg tgtccatgcc agcagacgga ggtttgtcca caactaacaa agctggtacg    540
aagttcggca cgggatattg tgacgcccaa tgcccaaaag atattaagtt catcaaagga    600
aaggcaaatt ctgatggctg dacagcttcc tcaaataatg ccaacacagg attcggcaca    660
accggtagtt gttgcaatga aatggatata tgggaagcaa acggaattag taatgctgtt    720
acacctcatt catgttctcc tggaaatgcc gcatgtacgt ccgatacgac ttgcggtagt    780
ggtgacggaa acagatacaa aggctattgc gataaggatg gatgcgactt taatccattc    840
agaatgggaa atcaaacttt ctacggcccc ggaaagacga tagatactac gaagccacta    900
acggtggtga cacagttcat aacgtcagac aatacagctt ctggcgactt agttgaaatt    960
agaagaaagt atgtgcaagg aggtaaagtg tttgatcagc ccaccagcaa cgtagccggt   1020
gtcagtggca attcaattac agacactttt tgcaagaacc agaaatctgt gtttggagat   1080
acgaatgact tcgcagctaa gggcggatta aaagcaatgg gagatgcatt tgctgatggt   1140
atggtcctag taatgtcctt atgggacgat tacgacgtca atatgcattg gcttaattca   1200
ccttatccaa ccgatgccga ccctacaaag ccaggtgttg ctagaggtac atgcagtatc   1260
actagtggaa agcccgctga tgtggagagc caaacccctg gtgctacagt tgtatactca   1320
aacattaaga ctggtccaat tggctctacg ttcagtggag cccagcaacc tggaggcccc   1380
ggatctggtt cctcaagtag ttcatccgca ggcggttcat ccactacgtc aaggtccagt   1440
agcactacct ctagagctac aactaccagc gtcggaacaa ccactacgac aacctctagt   1500
aggacgacca ctacaagcgc cgcaggcggt gtagttcaga aatatggcca gtgtggaggt   1560
ctaacttaca caggaccaac gacttgcgta tctggtacaa cgtgcacgaa ggctaatgat   1620
tattactccc aatgtttata a                                             1641
```